(12) United States Patent
Blaszczak et al.

(10) Patent No.: US 8,129,518 B2
(45) Date of Patent: Mar. 6, 2012

(54) SYNTHETIC POLYSACCHARIDE ANTIGENS FOR IMMUNOLOGICAL INTERVENTION IN DISEASE

(75) Inventors: Larry Chris Blaszczak, Indianapolis, IN (US); John Astor Cleveland, Jr., Zionsville, IN (US); Kathleen Ann Taylor, Fishers, IN (US); Neil Thomas Blackburn, Newark, DE (US); Angelika Regina Kraft, Indianapolis, IN (US); Charles Ellis Cohen, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/571,486

(22) PCT Filed: Sep. 15, 2004

(86) PCT No.: PCT/US2004/026737
§ 371 (c)(1),
(2), (4) Date: Mar. 8, 2006

(87) PCT Pub. No.: WO2005/035588
PCT Pub. Date: Apr. 21, 2005

(65) Prior Publication Data
US 2007/0041986 A1    Feb. 22, 2007

(51) Int. Cl.
*C08B 37/00* (2006.01)
*A61K 31/715* (2006.01)

(52) U.S. Cl. .................................. 536/53; 424/279.1
(58) Field of Classification Search .................. 536/53; 424/279.1
See application file for complete search history.

(56) References Cited

U.S. PATENT DOCUMENTS

| | | | |
|---|---|---|---|
| 4,186,194 A | | 1/1980 | Adam et al. |
| 5,834,435 A | * | 11/1998 | Slesarev .......................... 514/19 |
| 2001/0034325 A1 | * | 10/2001 | Slesarev ............................ 514/8 |
| 2004/0258779 A1 | * | 12/2004 | Pinegrin et al. ............... 424/757 |

FOREIGN PATENT DOCUMENTS

| | | |
|---|---|---|
| WO | WO 99/60155 | 11/1999 |
| WO | WO 01/79242 | 10/2001 |
| WO | WO 02/085929 | 10/2002 |
| WO | WO 03/075953 | 9/2003 |

OTHER PUBLICATIONS

Chetty et al. Infection and Immunity, 1982, 38(3), p. 1010-1019.*
Xu et al. J. Immunology, 2001, 167, p. 6975-6982.*
Inamura S. et al. (2001) Synthetic study of peptidoglycan partial structures. Synthesis of tetrasaccharide and octasaccharide fragments, Tetrahedron Letters 42, 7613-7618.
Inamura et al. (2006) Synthesis of peptidoglycan fragments and evaluation of their biological activity, Org. Biomol. Chem. 4, 232-242.
International Search Report for corresponding PCT/US2004/026737.
Heijenoort et al., "Membrane Intermediates in the Peptidoglycan Metabolism of *Escherichia coli*: Possible roles of PBP 1b and PBP 3", *Journal of Bacteriology*, vol. 174, No. 11, 1992, pp. 3549-3557.
Inamura, et al., "Synthetic study of peptidoglycan partial structures. Synthesis of tetrasaccharide and octasaccharide fragments," *Tetrahedron Letters*, vol. 42, 2001; pp. 7613-7616.
Jezek, et al., "Synthesis of tetrasaccharide containing glycopeptides related to bacterial cell wall starting from free tetrasacharide by the pentafluorophenyl ester method, " *Collection of Czechoslovak Chemical Communications*, vol. 55, 1990, pp. 1326-1335.
Rosenthal, Raoul and Roman Dziarski, "Isolation of Peptidoglycan and Soluble Peptidoglycan Fragments", Methods in Enzymology, Academic Press, Inc., 235:253-285 (1994).
Claims as allowed in related Chinese application No. CN 200480030122.X (Decision of Grant mailed Jun. 19, 2009).

* cited by examiner

*Primary Examiner* — Shaojia Anna Jiang
*Assistant Examiner* — Jonathan S Lau
(74) *Attorney, Agent, or Firm* — Sam K. Tahmassebi; TechLaw LLP

(57) ABSTRACT

Provided are synthetic polysaccharide antigens (SPAs) with anti-inflammatory or inflammatory immunomodulatory properties, depending on their structure. Also provided are compositions comprising these SPAs, and methods of using these SPAs and compositions to either prevent or treat inflammatory pathologies, or diseases or conditions susceptible to treatment with inflammatory immunomodulators, by using appropriate SPAs.

4 Claims, 8 Drawing Sheets

SYNTHETIC POLYSACCHARIDE ANTIGENS FOR IMMUNOLOGICAL INTERVENTION IN DISEASE

BACKGROUND OF THE INVENTION

1. Field of the Invention

The present invention relates to the field of immunology, and more particularly to immunomodulation. The present invention provides novel compounds and methods for immunological intervention in disease states by employing synthetic polysaccharide antigens (SPAs) possessing immunomodulatory properties. These SPAs can be used in humans and other animals to provide protection against and/or treatment of inflammatory pathologies, or to induce a controlled inflammatory response to treat disease states or conditions in which an inflammatory response is therapeutically beneficial, for example in antiviral therapy, anticancer therapy, or as a vaccine adjuvant.

2. Description of Related Art

Microbial antigens are the most powerful immunomodulators known. Among the most common examples are lipopolysaccharide (LPS) from Gram negative bacteria, and bacterial cell wall glycopeptides, also known as murein or peptidoglycan (PG), from both Gram negative and Gram positive bacteria. Bacterial PG is well established as a potent inflammatory agent (Wahl et al. (1986) *J. Exp. Med.* 165: 884).

Many microbial antigens, including PG, are thought to exert their pro-inflammatory effects by activating one of the mammalian cell surface receptors known as Toll-like receptors (TLRs). Activation of a TLR triggers an intracellular signaling pathway that leads to the induction of the transcription factor NF-κB, which in turn induces expression of genes encoding inflammatory mediators (chemokines and certain cytokines). PG itself is thought to activate through TLR2 (Takeuchi et al. (1999) *Immunity* 11:443).

Recently, cDNA array technology has brought even higher resolution to our understanding of pro-inflammatory mediator induction by PG (Wang et al. (2000) *J. Biol. Chem.* 275: 20260). The most highly activated genes are those expressing chemokines (IL-8 and MIP-1β), and the second most highly activated genes are those expressing cytokines (TNF-α, IL1, and IL6). Regardless of mechanistic detail, the downstream effect of bacterial PG on the host is a potent inflammatory response. In fact, PG has long been used for induction of arthritis in animal models (Cromartie et al. (1977) *J. Exp. Med.* 146:1585). Partially purified PG from the bacterium *Streptococcus pyogenes* is now commercially available for such purpose (Lee Laboratories, Atlanta, Ga.).

Low molecular weight fragments of PG, known collectively as muropeptides, also exhibit inflammatory effects in animals, and these effects are dependent on muropeptide structure (Tuomanen et al. (1993) *J. Clin. Invest.* 92:297). Even the very smallest fragments of PG, designated muramyl dipeptide (MDP), and glucosaminyl MDP (GMDP), as well as their derivatives, exhibit inflammatory effects in animals (Kohashi et al. (1980) *Infect. Immun.* 29:70). While the high molecular weight PG induces pro-inflammatory responses through cell surface located TLR2, low molecular weight fragments of PG induce their pro-inflammatory activities through intracellular receptors known as Nod1 and Nod2 (Girardin et al., published on the web on Jul. 18, 2003 in *J. Biol. Chem.* as manuscript M307198200).

Kasper and Tzianabos have demonstrated that certain polysaccharides purified from the surface of bacterial cells exhibit protective effects in vivo when tested in models of inflammation such as the formation of intraabdominal abscesses, intraabdominal sepsis, and post-surgical adhesions (U.S. Pat. Nos. 5,679,654 and 5,700,787; PCT International Publications WO 96/07427, WO 00/59515, and WO 02/45708). These investigators have demonstrated that when purified from whole capsule, certain polysaccharides derived from *Bacteroides fragilis, Staphylococcus aureus*, and *Streptococcus pneumoniae* have unique characteristics that set them apart from many polysaccharide antigens. The former molecules are high molecular weight, helical, and zwitterionic in nature (Wang et al. (2000) *Proc. Natl. Acad. Sci. USA* 97:13478-13481, and references 5-9 therein). Most bacterial polysaccharides are neutral or negatively charged, and are considered to be T cell-independent antigens (Abbas et al. (2000) *Cellular and Molecular Immunobiology*, W.B. Saunders, Philadelphia). Kasper and Tzianabos suggest that the zwitterionic nature of these polysaccharides plays a role in their interaction with CD4+ T cells (Tzianabos et al. (1993) *Science* 262: 416-419; Tzianabos et al. (2001) *Proc. Natl. Acad. Sci. USA* 98:9365-9370). More recent work by this group suggests that some of these molecules may interact with antigen presenting cells (APCs) via their zwitterionic characteristics and further, that stimulation of CD4+ T cells by these polysaccharide antigens is dependent on MHC II-bearing APCs (Kalka-Moll et al. (2002) *J. Immunol.* 169: 6149-6153). It has yet to be determined precisely how these interactions between zwitterionic polysaccharides and APCs may stimulate CD4+ T cells. These investigators have shown that zwitterionic polysaccharides activate CD4+ T cells in vitro as evidenced by the stimulation of proliferation and the production of the cytokines IL2, INFγ, and IL10, and that the protection is adoptively transferred by polysaccharide-stimulated T cells in vivo (PCT International Publication WO 00/59515; Kalka-Moll et al. (2000) *J. Immunol.* 164:719-724; Tzianabos et al. (2000) *J. Biol. Chem.* 275:6733-6738). In earlier studies by this group, stimulation of CD4+ cells did not necessarily depend on the presence of APCs, and the mitogenic properties of these molecules on T cells derived from rat and mouse species was different: rat splenocytes proliferated in response to CP1 treatment, while mouse splenocytes did not (Tzianabos et al. (1995) *J. Clin. Invest.* 96:2727-2731; Brubaker et al. (1999) *J. Immunol.* 162:2235-2242).

Overall, however, their observations led this group to hypothesize that the activation of CD4+ T cells by these polysaccharides leads to the production of cytokines such as IL2 or IL10 that protect against inflammatory responses (PCT International Publication WO 00/59515; Kalka-Moll et al. (2000) *J. Immunol.* 164:719-724; Tzianabos et al. (2000) *J. Biol. Chem.* 275:6733-6738; Tzianabos et al. (1999) *J. Immunol.* 163: 893-897). It remains unclear, however, exactly how these molecules activate T cells or how they exert their protective effects. Further confounding an understanding of these polysaccharides, this group has reported other studies indicating that the same zwitterionic polysaccharides can induce the formation of abscesses in the same in vivo model where protective effects of these molecules have been observed (Tzianabos et al. (1993) *Science* 262: 416-419; Tzianabos et al. (1994) *Infect. Immun.* 62:3590-3593). Therefore, from this body of literature, it is difficult to ascertain the mechanism whereby these zwitterionic polysaccharides act as suppressive modulators of the immune system in vivo.

Another group of investigators has described immunomodulatory effects of the exopolysaccharide (capsule-like) of *Paenibacillus jamilae*, a gram positive *bacillus* isolated from olive mill wastewaters (Ruiz-Bravo et al. (2001) *Clin. Diag. Lab. Immunol.* 8:706-710). Although the authors do not disclose the structural features of this polysaccharide, their results are similar to the work of Kasper and Tzianabos, summarized above. The molecule, referred to as CP-7, stimulates the proliferation of lymphocytes in culture, as well as significant expression of IFNγ and GMCSF. Further, this group reports that this compound renders mice resistant to

*Listeria monocytogenes* infection. The investigators suggest that the mechanism may be through the stimulation of an inflammatory Th1 response.

From the body of research discussed above, one can conclude that a poly-saccharide antigen may induce a pro-inflammatory or anti-inflammatory response depending on structural features which are not presently fully understood.

In view of the confusing and sometimes contradictory effects reported in the literature for various immunomodulatory polysaccharides, there exists a need in the art for an understanding of the structural bases underlying immunomodulation by polysaccharides, pro-inflammatory as well as anti-inflammatory. There exists as well as a need for additional therapeutic molecules, both pro-inflammatory and anti-inflammatory, that modulate the immune response in a safe and effective manner. Such insight and additional molecules will facilitate the development of even more effective immunotherapeutic strategies for disease prevention and treatment.

SUMMARY OF THE INVENTION

Accordingly, the present invention provides linear, non-crosslinked, immunomodulatory polymeric compounds of Formula I:

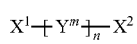

Formula I wherein:

the subscript n, representing the number of momomeric units of formula $Y^m$ in the polymer, is a single integer in the range from 2 to 375;

the superscript m, representing the position of a particular monomeric unit $Y^m$ in the polymer, sequentially from left to right, is a series of integers from 1 to n;

$X^1$ is H or a terminal group;
$X^2$ is OH or a terminal group;
each monomeric unit of formula $Y^m$ is independently:
(a) a group of Formula IIa when $Y^m$ is not $Y^n$, or

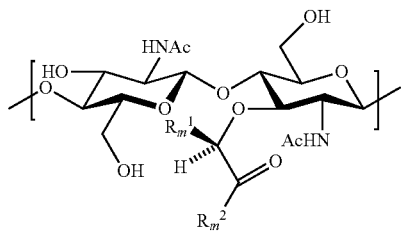

Formula IIa each of $R_1^1, R_2^1, \ldots, R_{n-1}^1$ and $R_n^1$ is independently H or lower alkyl;

each of $R_1^2, R_2^2, \ldots, R_{n-1}^2$ and $R_n^2$ is independently —OH, —NH$_2$, an amino acid residue, or a peptide comprising 2 to 10 amino acid residues, wherein:

(b) a group of Formula IIb when $Y^m$ is $Y^n$

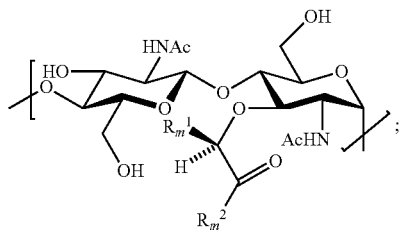

Formula IIb (c) each amino acid residue is independently in the D or L configuration;

(d) each amino acid residue is unsubstituted or substituted with one or more groups selected from halo, alkyl, hydroxy, alkoxy, phenoxy, CF$_3$, amino, alkylamino, dialkylamino, —C(O)Oalkyl and —NO$_2$; and (e) the amino acid residues are independently joined at the α or γ carboxyl groups, and at the α or ε amino groups, or any combination thereof;

or a pharmaceutically acceptable salt thereof, provided the linear polymer is not:

(a) a homopolymer of the following formula, wherein n is 75 to 375:

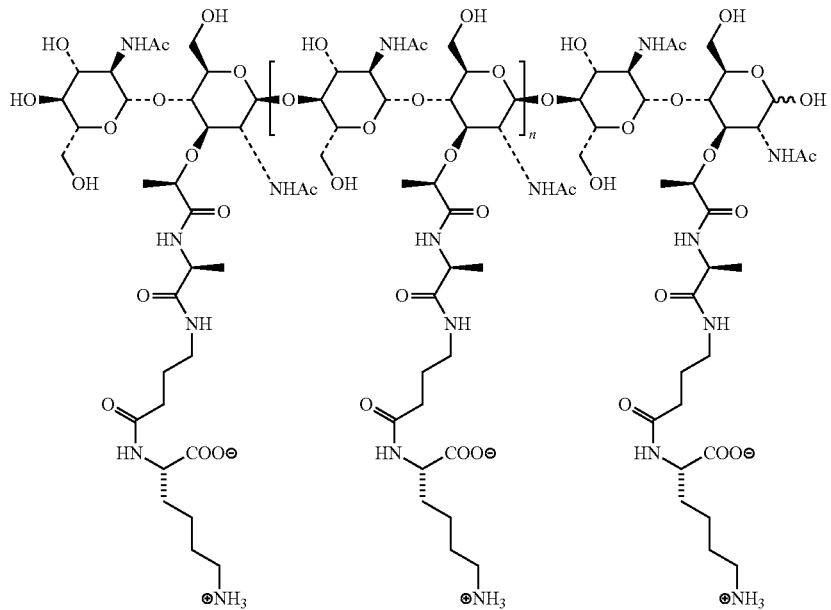

(b) or a homopolymer comprising a monomeric unit of the following formula:

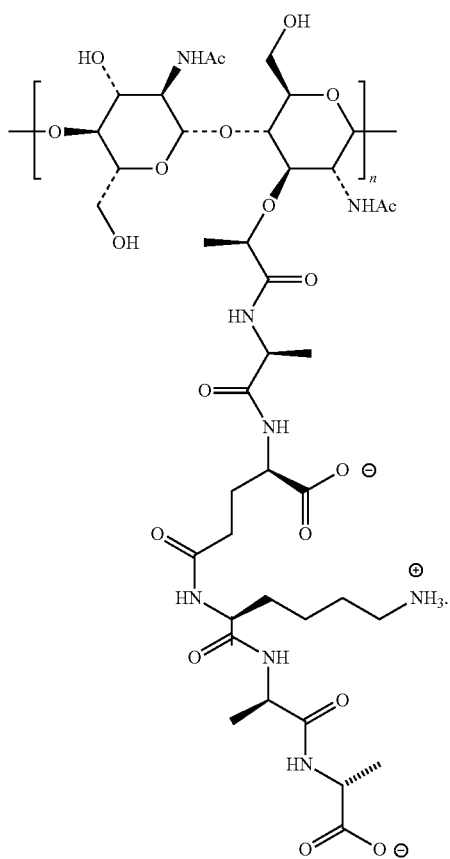

Preferably, each of $R_1^1, R_2^1, \ldots, R_{n-1}^1$ and $R_n^1$ is methyl.

In another embodiment, $X^1$ is H and $X^2$ is OH.

In another embodiment, n is 75 to 375, or 2 to 10, or 2 to 3.

In another embodiment, one or more of $R_1^2, R_2^2, \ldots, R_{n-1}^2$ and $R_n^2$ is a dipeptide, a tripeptide, a tetrapeptide or a pentapeptide. Preferably, each of $R_1^2, R_2^2, \ldots, R_{n-1}^2$ and $R_n^2$ is a dipeptide, tripeptide, a tetrapeptide or a pentapeptide.

In another embodiment, one or more of the monomeric units of formula $Y'''$ is:

(a) a group of Formula IIa, when $Y'''$ is not $Y''$; or

Formula IIIa

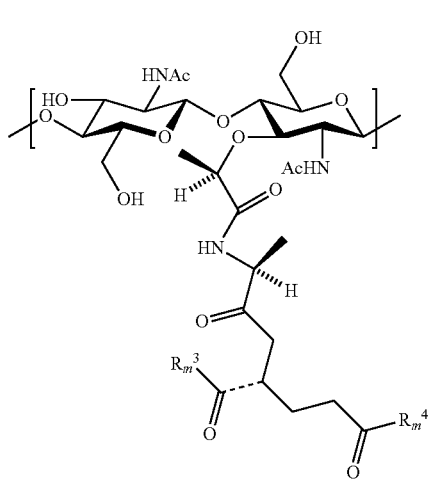

(b) a group of Formula IIIb, when $Y'''$ is $Y''$

Formula IIIb

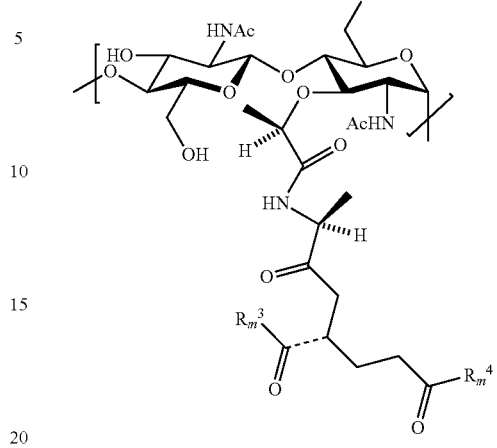

wherein:

each of $R_1^3, R_2^3, \ldots R_{n-1}^3$ and $R_n^3$ is independently —OH or —NH$_2$;

each of $R_1^4, R_2^4$, and $R_{n-1}^4$ is independently —OH or —NH$_2$, an amino acid residue, or a peptide comprising 2 to 8 amino acid residues, wherein:

(c) each amino acid residue is independently in the D or L configuration;

(d) each amino acid residue is unsubstituted or substituted with one or more groups selected from halo, alkyl, hydroxy, alkoxy, phenoxy, CF$_3$, amino, alkylamino, dialkylamino, —C(O)Oalkyl and —NO$_2$; and (e) the amino acid residues are independently joined at the α or γ carboxyl groups, and at the α or ε amino groups, or any combination thereof.

Preferably, each of the monomeric units of formula $Y'''$, other than $Y''$, is a group of Formula IIIa; and $Y''$ is a group of Formula IIIB. These compounds are referred to herein as compounds of Formula V. Preferably, these compounds are substantially pure.

In another embodiment, non of the monomeric units of formula $Y'''$ is:

(a) a group of Formula IIa, when $Y'''$ is not $Y''$; or

Formula IIIa

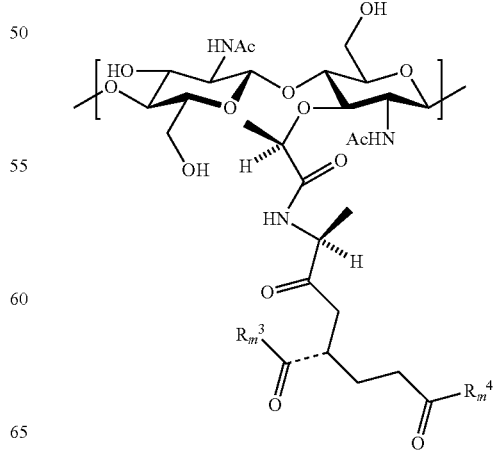

(b) a group of Formula IIIb, when Y′″ is Y″

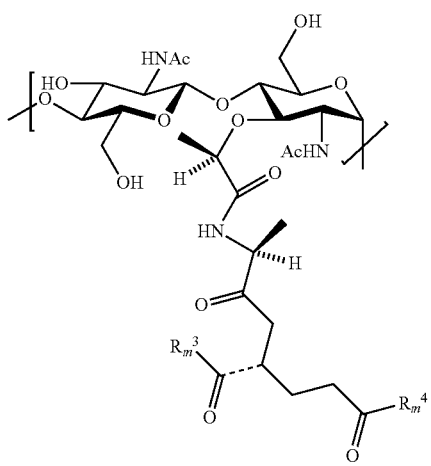

Formula IIIb wherein:
each of $R_1^3, R_2^3, \ldots R_{n-1}^3$ and $R_n^3$ is independently —OH or —NH$_2$;
each of $R_1^3, R_2^4, \ldots R_{n-1}^4$ and $R_n^4$ is independently —OH or —NH$_2$, an amino acid residue, or a peptide comprising 2 to 8 amino acid residues, wherein:
  (c) each amino acid residue is independently in the D or L configuration;
  (d) each amino acid residue is unsubstituted or substituted with one or more groups selected from halo, alkyl, hydroxy, alkoxy, phenoxy, CF$_3$, amino, alkylamino, dialkylamino, —C(O)Oalkyl and —NO$_2$; and
  (e) the amino acid residues are independently joined at the α of γ carboxyl groups, and at the α or ε amino groups, or any combination thereof.

These compounds are referred to herein as compounds of Formula VI.

In another embodiment, one or more of $R^{12}, R_2^2, \ldots, R_{n-1}^2$ and $R_n^2$ has a net charge, preferably a negative net charge. Preferably, each of $R_1^2, R_2^2, \ldots, R_{n-1}^2$ and $R_n^2$ has a net charge, preferably a negative net charge.

In another embodiment, one or more of $R_1^2, R_2^2, \ldots, R_{n-1}^2$ and $R_n^2$ has a net neutral charge. Preferably, each of $R_1^2, R_2^2, \ldots, R_{n-1}^2$ and $R_n^2$ has a net neutral charge.

In another embodiment, the linear polymer is a homopolymer.

In another embodiment, the linear polymer is a random copolymer, alternating copolymer, or block copolymer. Preferably, the linear polymer is a random copolymer. The linear copolymer can comprise 2 to 375 different monomeric units.

In another embodiment, the present invention provides a composition, comprising any of the foregoing compounds or a salt thereof, together with a buffer, diluent, excipient, or carrier. The composition can further comprise a dispersing agent, e.g., polyethylene glycol, glycerol or sucrose.

In another embodiment, the present invention provides a pharmaceutical composition, comprising any of the foregoing compounds or pharmaceutically acceptable salts thereof, together with a pharmaceutically acceptable buffer, diluent, excipient, or carrier. The pharmaceutical composition can further comprise a dispersing agent, e.g., polyethylene glycol, glycerol or sucrose.

In another embodiment, the present invention provides the use of a compound of Formula I, or a pharmaceutically acceptable salt thereof, for the preparation of a medicament for the treatment of a disease or disorder susceptible to treatment with an immunodulator.

In another embodiment, the present invention provides the use of a compound of Formula V, or a pharmaceutically acceptable salt thereof, for the preparation of a vaccine adjuvant.

In another embodiment, the present invention provides the use of a compound of Formula I, or a pharmaceutically acceptable salt thereof, for the treatment of a disease or disorder susceptible to treatment with an immunodulator.

In another embodiment, the present invention provides a method of inducing an immune response in a mammal, comprising administering to said mammal an effective amount of a compound of Formula I, or a pharmaceutically acceptable salt thereof.

In another embodiment, the immune response is inflammatory and the compound is a compound of Formula V, or a pharmaceutically acceptable salt thereof.

In another embodiment, the immune response is anti-inflammatory and the compound is a compound of Formula VI, or a pharmaceutically acceptable salt thereof.

In another embodiment, the present invention provides a method of inhibiting the maturation of an antigen presenting cell, comprising contacting in vitro said antigen presenting cell and an effective amount of a compound of Formula VI or a pharmaceutically acceptable salt thereof for a time and under conditions effective to inhibit maturation of said antigen presenting cell.

In another embodiment, the present invention provides a method of inhibiting the maturation of an antigen presenting cell in a mammal, comprising administering to a mammal an effective amount of a compound of Formula VI or a pharmaceutically acceptable salt thereof and inhibiting maturation of said antigen presenting cell.

In another embodiment, the present invention provides a method of inhibiting an inflammatory response in a mammal in need thereof, comprising:
  (a) isolating peripheral blood mononuclear cells, or a monocyte-containing fraction thereof, from said mammal;
  (b) contacting in vitro said isolated peripheral blood mononuclear cells or monocytes and a composition containing an effective amount of cytokines that differentiate monocytes to immature dendritic cells for a time and under conditions effective to generate immature monocyte-derived dendritic cells;
  (c) contacting in vitro said immature monocyte-derived dendritic cells and an effective amount of a compound of Formula VI or a pharmaceutically acceptable salt thereof for a time and under conditions effective to prevent maturation of said immature monocyte-derived dendritic cells; and
  (d) administering said immature monocyte-derived dendritic cells to said mammal, reducing the ability of dendritic cells of said mammal to drive cognate interactions with T cells and inhibiting said inflammatory response in said mammal.

In this and the other ex vivo methods disclosed herein, administration of treated cells can be performed intravenously, intraperitoneally, or via intercardiac route.

Inflammatory responses that can be treated via the foregoing and following methods include abscesses and post-surgical adhesions, sepsis; rheumatoid arthritis; myesthenia gravis; inflammatory bowel disease; colitis; systemic lupus erythematosis; multiple sclerosis; coronary artery disease; diabetes; hepatic fibrosis; psoriasis; eczema; acute respiratory distress syndrome; acute inflammatory pancreatitis; endoscopic retrograde cholangiopancreatography-induced pancreatitis; burns; atherogenesis of coronary, cerebral, and peripheral arteries; appendicitis; cholecystitis; diverticulitis; visceral fibrotic disorders; wound healing; skin scarring disorders; granulomatous disorders; asthma; pyoderma gangrenosum; Sweet's syndrome; Behcet's disease; primary sclerosing cholangitis; and cell, tissue, or organ transplantation.

In yet another embodiment, the present invention provides a method of inhibiting an inflammatory response in a mammal in need thereof, comprising:
administering to said mammal an effective amount of a compound of Formula VI or a pharmaceutically acceptable salt thereof for preventing dendritic cells or other antigen presenting cells of said mammal from maturing and rendering them incapable of stimulating T cell activation,
thereby inhibiting said inflammatory response in said mammal.

In another embodiment, the present invention provides a method of inhibiting an inflammatory response in a mammal in need thereof, comprising:
(a) isolating peripheral blood mononuclear cells, or a monocyte-containing fraction thereof, from said mammal;
(b) contacting in vitro said isolated peripheral blood mononuclear cells or monocytes and a composition containing an effective amount of cytokines that differentiate monocytes to immature dendritic cells for a time and under conditions effective to generate immature monocyte-derived dendritic cells;
(c) contacting in vitro said immature monocyte-derived dendritic cells and an effective amount of a compound of Formula VI or a pharmaceutically acceptable salt thereof for a time and under conditions effective to prevent maturation of said immature monocyte-derived dendritic cells;
(d) contacting in vitro said immature dendritic cells and naïve T cells to generate T regulatory cells; and
(e) administering said T regulatory cells that suppress T effector cells to said mammal,
thereby suppressing said inflammatory response.

In a further embodiment, the present invention provides a method of inhibiting an inflammatory response in a mammal in need thereof, comprising:
administering to said mammal an effective amount of a compound of Formula VI or a pharmaceutically acceptable salt thereof,
generating T regulatory cells that suppress T effector cells and that inhibit said inflammatory response.

In another embodiment, the present invention provides a method of measuring the immunological activity of a compound of Formula VI or a pharmaceutically acceptable salt thereof, comprising:
administering the compound to said mammal;
administering Candin to said mammal; and
measuring the inhibition of delayed type hypersensitivity skin lesions elicited by said Candin,
wherein a reduction in lesion size in said mammal compared to lesion size in an untreated control mammal that has not received the compound indicates that said compounds are effective in inhibiting a localized inflammatory response.

In another embodiment, the present invention provides a method of activating a toll-like receptor of an antigen presenting cell, comprising contacting said antigen presenting cell and an effective amount of a compound of Formula V or a pharmaceutically acceptable salt thereof for a time and under conditions effective to activate said toll-like receptor. The toll-like receptor can be toll-like receptor 2.

In another embodiment, the present invention provides a method of preventing or treating a viral infection or cancer in a mammal in need thereof, comprising administering to said mammal an effective amount of a compound of Formula V or a pharmaceutically acceptable salt thereof.

In another embodiment, the present invention provides a method of inducing an immune response in a mammal, comprising administering to said mammal an effective amount of a linear homopolymer of the following formula, where n is 2 to 375:

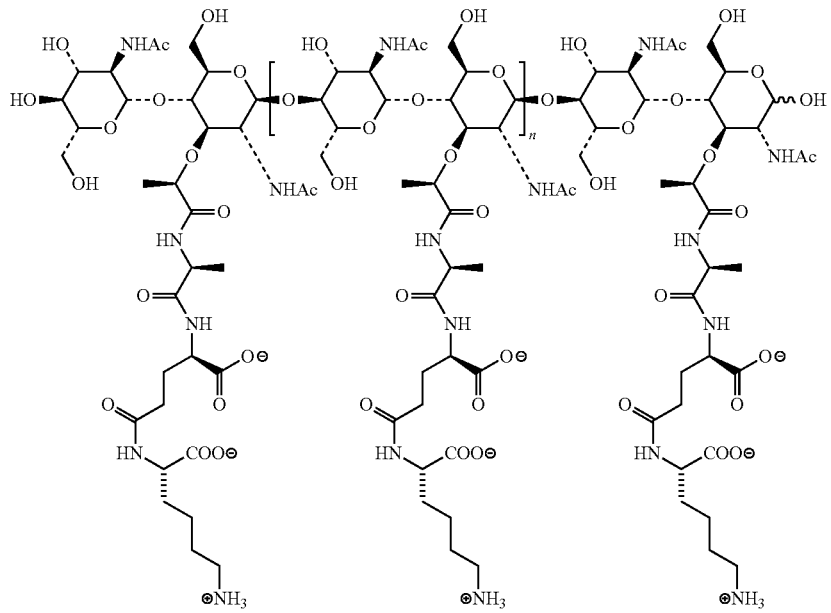

The present invention encompasses all combinations of the embodiments disclosed herein.

Further scope of the applicability of the present invention will become apparent from the detailed description provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

BRIEF DESCRIPTION OF THE DRAWINGS

The above and other aspects, embodiments, features, and advantages of the present invention will be better understood from the following detailed description taken in conjunction with the accompanying drawings, all of which are given by way of illustration only, and are not limitative of the present invention, in which.

DETAILED DESCRIPTION OF THE INVENTION

Figure 1:
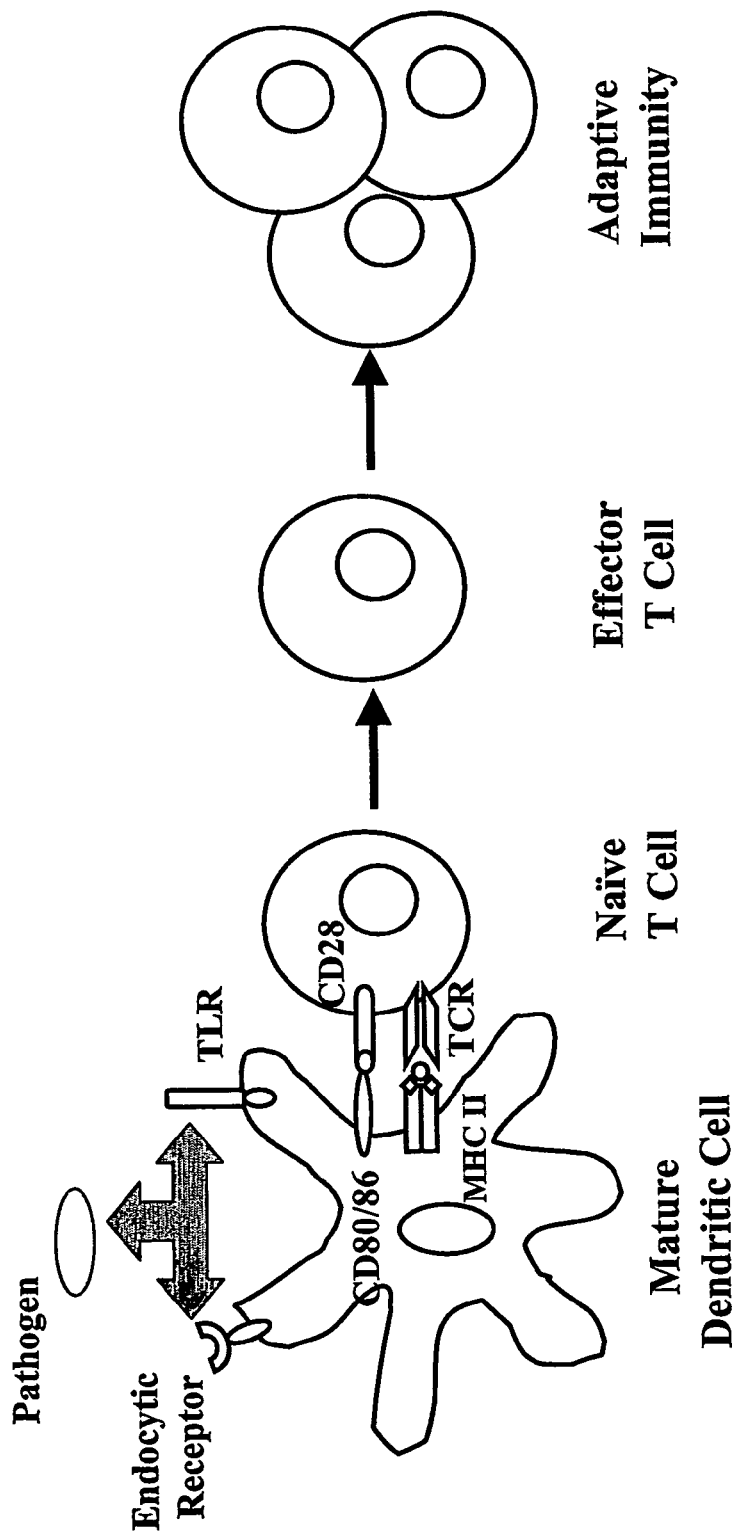
FIG. 1 is a schematic showing the normal events that occur when interactions between dendritic cells and T cells lead to inflammation or adaptive immunity

The following detailed description of the invention is provided to aid those skilled in practicing the present invention. Even so, the following detailed description should not be construed to unduly limit the present invention as modifications and variations in the embodiments discussed herein can be made by those of ordinary skill in the art without departing from the spirit or scope of the present inventive discovery.

The contents of each of the references cited herein are herein incorporated by reference in their entirety.

DEFINITIONS

As used herein, the abbreviation "h" or "hr" means hour(s). The abbreviation "min" means minute(s).

As used herein, unless indicated otherwise, the following terms have the following meanings:

"Ac" means $CH_3C(O)$—.

"Alkyl" means an aliphatic hydrocarbon group which may be straight or branched having about 1 to about 20 carbon atoms in the chain. Preferred alkyl groups have 1 to about 12 carbon atoms in the chain, more preferred is lower alkyl as defined herein. Branched means that one or more lower alkyl groups such as methyl, ethyl or propyl are attached to a linear alkyl chain. "Lower alkyl" means about 1 to about 4 carbon atoms in the chain that may be straight or branched.

"Amino acid" means an amino acid selected from the group consisting of natural and unnatural amino acids as defined herein. Amino acid is also meant to include -amino acids having L or D stereochemistry at the α-carbon. Preferred amino acids are those possessing an α-amino group. The amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are α-amino acids. Exemplary natural amino acids are isoleucine, proline, phenylalanine, tryptophan, methionine, glycine, serine, threonine, cysteine, tyrosine, asparagine, glutamine, lysine, arginine, histidine, aspartic acid and glutamic acid. Unnatural amino acid" means an amino acid for which there is no nucleic acid codon. Examples of unnatural amino acids include, for example, the D-isomers of the natural α-amino acids as indicated above; Aib (aminobutyric acid), βAib (3-amino-isobutyric acid), Nva (norvaline), β-Ala, Aad (2-aminoadipic acid), βAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), aIle (allo-isoleucine), Nle (norleucine), tert-Leu, Cit (citrulline), Orn, Dpm (2,2'-diaminopimelic acid), Dpr (2,3-diaminopropionic acid), α- or β-Nal, Cha (cyclohexyl-Ala), hydroxyproline, Sar (sarcosine), and the like; cyclic amino acids; N$^α$-alkylated amino acids such as MeGly (N$^α$-methylglycine), EtGly (N$^α$-ethylglycine) and EtAsn (N$^α$-ethylasparagine); and amino acids in which the α-carbon bears two side-chain substituents. The names of natural and unnatural amino acids and residues thereof used herein follow the naming conventions suggested by the IUPAC Commission on the Nomenclature of Organic Chemistry and the IUPAC-IUB Commission on Biochemical Nomenclature as set out in "Nomenclature of a-Amino Acids (Recommendations, 1974)" Biochemistry, 14(2), (1975). To the extent that the names and abbreviations of amino acids and residues thereof employed in this specification and appended claims differ from those noted, differing names and abbreviations will be made clear.

"Amino acid residue" means the individual amino acid units incorporated into a peptide, or peptide portion of a molecule, through an amide linkage.

The term "biomarker" means a marker of a specific activity that correlates with the administration of a drug. Non-limiting examples of biomarkers include a cell surface receptor, a soluble mediator, an mRNA message, or an in vivo response that is modulated and that can be measured.

"Effective amount" refers to an amount of a compound or composition of the present invention effective to produce the desired or indicated immunologic or therapeutic effect.

"IL10" is an endogenous mediator that is often involved in the down modulation of inflammatory responses. Directed, endogenous generation of IL10 may maximize efficacy and minimize toxic effects.

"Immune cell" means any cell capable of responding or mounting a response within the entirety of the host immune system. Generally these cells are referred to as "white blood cells" but are not necessarily limited to this category. Examples of immune cells include T and B cells, monocytes, macrophages, natural killer cells, dendritic cells, antigen presenting cells, and polymorphonuclear leukocytes.

The terms "inflammation," "inflammatory response," "pro-inflammatory response," or the like refer to the complex bodily process initiated by tissue damage, either endogenous or exogenous. Inflammatory response to such damage involves the induction of soluble factors such as cytokines including, but not limited to, interleukin-(IL-) 1, IL-6, and tumor necrosis factor (TNF)-α, as well as chemokines including, but not limited to, IL-8, interferon-γ, and macrophage induction protein (MIP)-1β. Several immune cell populations also participate in the inflammatory response, including, but not limited to neutrophiles, macrophages, and lymphocytes. Although inflammation evolved as, and may be induced as, a protective function, numerous examples of inflammatory pathologies may be encountered (e.g., inflammatory bowel disease, formation of excess post-surgical adhesions, and abscess formation, among many others).

The terms "anti-inflammation," "anti-inflammatory," or the like refer to any process by which an inflammatory response is attenuated or reversed. Such processes include, but are not limited to, induction of soluble mediators such as IL-10, or induction of cell populations such as regulatory T ($T_{reg}$) cells.

"Immune response" means either a pro-inflammatory or anti-inflammatory response of the immune system.

The terms "modulate" or "modulation" or the like mean either an increase or a decrease in a selected parameter.

"Net charge" means the arithmetic sum of the charges in an ionic species, e.g., a peptide having charge (−) where there is a net negative charge; a peptide having charge (+,−,−) where there is a net negative charge; a peptide having charge (+,+,−) where there is a net positive charge; a peptide having charge (−,−) where there is a net negative charge; a peptide having charge (+) where there is a net postitive charge, etc. Note particularly that in a peptide having charge (+,−) there is no net charge.

"Non-immune cell" means a cell that is not normally involved in immune responses but that may have the capacity to be modulated by products of the immune system.

The terms "patient" or "subject" refer to mammals and other animals including humans and other primates; companion, zoo, and farm animals, including, but not limited to, cats, dogs, rodents, horses, cows, sheep, pigs, goats; poultry; etc.

"Peptide" means a polymer comprising amino acid residues joined together through amide bonds.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylenebis-β-hydroxynaphthoates, gentisates, isethionates, di-p-toluoyltartrates, methanesulphonates, ethanesulphonates, benzenesulphonates, p-toluenesulphonates, cyclohexylsulphamates and quinateslaurylsulphonate salts, and the like. See, for example S. M. Berge, et al., "Pharmaceutical Salts," *J. Pharm. Sci.* 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids; e.g., lysine and arginine, and dicyclohexylamine, and the like.

"Substantially pure" means a purity in the range from about 90% to about 100%, more preferably from about 95% to about 100%, and even more preferably from about 97% to about 100%, including individual values of 90%, 91%, 92%, 93%, 94%, 95%, 96%, 97%, 98%, 99%, and 100%, or any range therein. Compounds of the present invention can be obtained in substantially pure or isolated form, free from the bulk of biological contaminants, including other molecules having immunomodulatory activity, that are customarily present in preparations of peptidoglycans isolated from natural bacterial sources.

"Synthetic polysaccharide antigen" or "SPA" as defined herein is synthetically produced, substantially pure, linear, uncrosslinked, polymer of N-acylglucosaminyl-β-[1,4]-N-acylmuramyl-peptide. The peptide may comprise two or more amino acids, natural or unnatural structures, D or L configuration. Pure synthetic polysaccharide antigen as disclosed herein is essentially devoid of naturally occurring bacterial cell wall contaminants. Such antigens are not available from natural sources by any known chemical or enzymatic method. Note that this definition includes, but is not limited to, native, uncrosslinked, bacterial peptide sequences. Compounds 1 and 2 disclosed herein, which are synthetic peptidoglycans (PGs), are particular SPAS. SPAs can be produced by total synthesis.

"Terminal group": The synthetic polymers of the present invention terminate at a muramic acid residue with a free reducing anomeric alcohol. It will be recognized by those skilled in the art that the N-acetylmuramyl termini, being glucopyranosyl in structure, may be treated with an aryl amine to form C-1 N-aryl derivatives and with aryl hydrazines to form C-1 hydrazones. Furthermore, limited enzymatic digestion of the synthetic polymers with a lytic transglycosylase (e.g., Dijkstra et al. (1994) Curr. Opin. Struct. Biol. 4:810) will produce termini with muramyl-[1,6]-anhydro linkages which can be used for chemical modifications of the resulting anomeric carbons.

"T regulatory cells" or "$T_{regs}$" refers to a unique lineage of immunoregulatory T cells that potently suppress inflammatory effector T cells in vitro and in vivo. $T_{regs}$ are characterized by expression of certain cell surface markers including, for example, CD4 and CD25 (CD4+/CD25+).

"Zwitterion" means a unimolecular dipolar ion per polysaccharide repeat unit or polypolar ion including, for example, molecules with charges (+,−), (+,−,−), etc.

Immunomodulators of the Present Invention

The compounds of Formula I of the present invention are linear, non-crosslinked polymers, and include homopolymers and copolymers of various types. These polymers can be accessed through chemo-enzymatic total synthesis, for example from N-acetyl-glucosamine. Furthermore, depending on their structure, compounds of the present invention can either be inflammatory or anti-inflammatory.

Compound 1, shown below, a compound of Formula VI, is an example of an anti-inflammatory immunomodulator. It is a homopolymer of the indicated repeat unit, existing as a distribution of molecular weights centered around 150 kilodaltons. The polymer is a hygroscopic white powder that is soluble in water or saline.

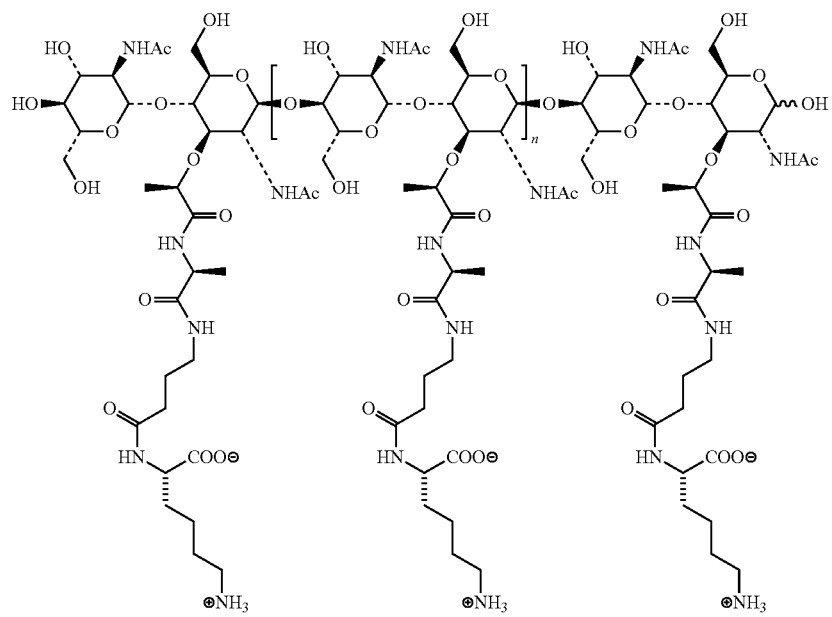

Compound 1

Natural peptidoglycan in the bacterial cell wall is a single covalently closed macromolecule that precisely defines the shape of a bacterial cell throughout the cell cycle. It is composed of a rigid axis of parallel polymeric peptidoglycan glycan strands wherein the repeat unit is β-[1,4]-linked N-acetylglucosaminyl-β-[1,4]-N-acetyl-muramylpentapeptide. The glycan strand is helical in shape with about four repeat units per complete turn of the helix. The more flexible pentapeptide axes extend N to C from the lactyl carboxyls of the muramic acid residues. The peptide is generally $H_2N$-Ala-D-iso-Glu (or iso-Gln)-Lys (or diaminopim-elate, DAP)-D-Ala-D-Ala-COOH. The peptides may be crosslinked between Lys (or DAP) from a donor strand to the carbonyl of the penultimate D-Ala of an acceptor strand. The actual degree of crosslinking in a living cell varies with by genus, and is always less than 100%. In comparison, the compounds of the present invention are linear, i.e., there is no crosslinking in the peptides.

As shown below, Compound 1 protects against the induction of inflammation in models of intraabdominal abscesses and post-surgical adhesions. As demonstrated in the examples presented below, investigation into the mechanism of protection induced by this molecule reveals that it may inhibit the maturation of dendritic cells, the most powerful antigen presenting cells (APCs) in the immune cell repertoire. Immature APCs are unable to activate T cells due to the their inability to signal T cells through co-stimulation. Treatment of human PBMCs with Compound 1 fails to stimulate activation or proliferation of T cells. Treatment of human PBMCs with other molecules of Formula VI should also fail to stimulate activation or proliferation of T cells. This is completely unexpected in view of the literature on both zwitterionic polysaccharides and naturally occurring peptidoglycans, discussed earlier. Both zwitterionic polysaccharides and naturally occurring peptidoglycans have been reported to be mitogens for T cell activation (PCT International Publication WO 00/59515; Kalka-Moll et al. (2000) *J. Immunol.* 164:719-724; Tzianabos et al. (2000) *J. Biol. Chem.* 275:6733-6738; Levinson et al. (1983) *Infect. Immun.* 39:290-296). Furthermore, Compound 1 fails to stimulate Toll-like receptors in reporter cells in vitro, or to stimulate the expression of inflammatory cytokines in PBMC cultures, events that would be expected if maturation of APCs occurs through stimulation of TLR2 or other TLRs (Schwander et al. (1999) *J. Biol. Chem.* 274:17406-17409; Medzhitov et al. (2001) *Nat. Rev. Immunol.* 6: 135-145) with subsequent activation of T cells through the expected cognate interactions between the two cells types in the presence of antigen. It is expected that other compounds of Formula VI will not be ligands for TLR2 or other TLRs. The present inventors also predict an increase in the number of CD4+ CD25+ cells present in PBMC cultures following treatment with molecules of Formula VI, suggesting that treatment with such molecules creates a population of immature APCs that drive the stimulation of T regulatory cells within the culture. This hypothesis is further supported by functional observations of suppression of proliferation of T cells in PBMC cultures stimulated with anti-CD3 antibodies following treatment with Compound 1.

Finally, the inventors have also surprisingly discovered that when human PBMCs are treated in vitro with Compound 1, the response is most notably the expression of IL10. Negligible expression of IL2, IFN-γ, TNF-α, IL6, or IL12 is observed. IL10 is a type II cytokine with pleomorphic effects (Moore et al. (2001) *Annu. Rev. Immunol.* 19:683-765). It has been shown to have potent anti-inflammatory activity, down-modulating inflammatory responses of T effector cells (Morel et al. (2002) *Immunol.* 106:229-236), dendritic cells (Martin et al. (2003) *Immunity* 18:155-167), and other antigen presenting cells (Williams et al. (2002) *J. Leuko. Biol.* 72:800-809). IL10 is produced by a variety of cell types, including T cells, dendritic cells, monocytes (Moore et al. (2001) *Annu. Rev. Immunol.* 19:683-765), and a specialized sub-set of T cells known as T regulatory (Treg) cells (Suri-Payor et al (2001) *J. Autoimmun.* 16:115-123). In many ways, this cytokine functions to help maintain a dynamic balance within the immune system. IL10 acts to tamp down unchecked inflammatory responses that could otherwise be deleterious to the host (Moore et al. (2001) *Annu. Rev. Immunol.* 19:683-765).

These results are in direct contrast to the body of literature characterizing the recognition of bacterial peptidoglycans by the immune system. Furthermore, the stimulation of an anti-inflammatory response by compounds of Formula VI disclosed herein is completely novel and unexpected in view of the current body of evidence regarding natural peptidoglycans, discussed above, indicating that bacterial peptidoglycan is a potent inflammatory agent. Thus, while natural peptidoglycans are potently inflammatory, the presently disclosed compounds of Formula VI are anti-inflammatory. The inventors' surprising discovery that compounds of Formula VI should exhibit in vitro anti-inflammatory activity contrasts markedly with previously published observations on the activity of purified bacterial peptidoglycans, and prompted testing of the activity of Compound 1 in animal models of inflammation. As demonstrated below, this synthetic peptidoglycan exhibits protective therapeutic effects in an animal model of inflammation-based pathology.

Compound 2, which is representative of compounds of Formula V of the present invention, is an example of an inflammatory immunomodulator.

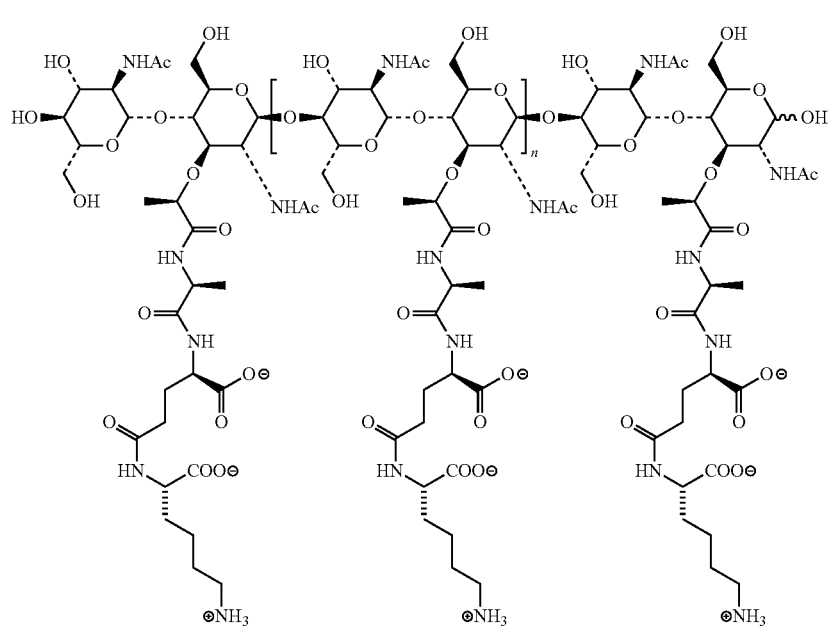

Compound 2

This molecule activates TLR2 (data not shown) and, as shown below, induces modest production of the pro-inflammatory cytokine TNF-α by human PBMCs. The modest pro-inflammatory activity of Compound 2 contrasts with the potent inflammatory activity of natural peptidoglycans isolated from bacterial sources. This difference is most likely due to the presence and activities of numerous biological contaminants present in the heterogeneous material isolated from bacteria.

The linear, non-crosslinked polymers of Formula I:

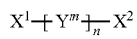

Formula I comprise n independent monomeric units of Formula $Y^m$. The subscript n, representing the number of momomeric units of Formula $Y^m$ in the polymer, is a single integer in the range from 2 to 375. For example, when n=2, there are two monomeric units: $Y^1$ and $Y^2$. When n=3, there are three monomeric units: $Y^1$, $Y^2$ and $Y^3$. When n=375, there are 375 monomeric units: $Y^1$, $Y^2$, $Y^3$, . . . , $Y^{374}$ and $Y^{375}$.

The superscript m, representing the position of a particular monomeric unit $Y^m$ in the polymer sequentially from left to right, is a series of integers from 1 to n. $Y^1$ is directly attached to $X^1$ while $Y^n$ is directly attached to $X^2$. Illustrative examples of sequences include the following:

| n | m | Polymer of Formula I |
|---|---|---|
| n | 1, 2, 3, . . . n − 1 and n | $X^1$-$Y^1$-$Y^2$-$Y^3$- . . . -$Y^{n-1}$-$Y^n$-$X^2$ |
| 2 | 1 and 2 | $X^1$-$Y^1$-$Y^2$-$X^2$ |
| 3 | 1, 2 and 3 | $X^1$-$Y^1$-$Y^2$-$Y^3$-$X^2$ |
| 4 | 1, 2, 3 and 4 | $X^1$-$Y^1$-$Y^2$-$Y^3$-$Y^4$-$X^2$ |
| 375 | 1, 2, 3, . . . , 374 and 375 | $X^1$-$Y^1$-$Y^2$-$Y^3$-$Y^4$- . . . -$Y^{374}$-$Y^{375}$-$X^2$ |

Each monomeric unit $Y^m$ (i.e., each of $Y^1$, $Y^2$, . . . , $Y^{n-1}$ and $Y^n$) is independently selected, such that they can all be the same, all be different, or any combination thereof. Thus, the invention includes homopolymers (i.e., all monomers are the same) and copolymers (i.e., two or more different monomers). The copolymers can be random copolymers, block copolymers or alternating copolymers. For example, if $Y^1$ and $Y^2$ represent two different monomeric units of Formula $Y^m$, the polymer types can be illustrated as follows:

| Polymer Type | Illustrative Example |
|---|---|
| Homopolymer: | $X^1$-$Y^1$-$Y^1$-$Y^1$-$Y^1$-$Y^1$-$Y^1$-$Y^1$-$Y^1$-$Y^1$-$Y^1$-$Y^1$-$Y^1$-$Y^1$-$X^2$ |
| Random copolymer | $X^1$-$Y^1$-$Y^2$-$Y^1$-$Y^1$-$Y^2$-$Y^2$-$Y^2$-$Y^1$-$Y^2$-$Y^1$-$Y^1$-$Y^2$-$Y^1$-$X^2$ |
| Block copolymer | $X^1$-$Y^1$-$Y^1$-$Y^1$-$Y^2$-$Y^2$-$Y^2$-$Y^1$-$Y^1$-$Y^1$-$Y^2$-$Y^2$-$Y^2$-$X^2$ |
| Alternating Copolymer | $X^1$-$Y^1$-$Y^2$-$Y^1$-$Y^2$-$Y^1$-$Y^2$-$Y^1$-$Y^2$-$Y^1$-$Y^2$-$Y^1$-$Y^2$-$X^2$ |

In the polymers of Formula I, each monomeric unit of Formula $Y^m$ is independently:

(a) a group of Formula IIa, when $Y^m$ is not $Y^n$; or (a) a group of Formula IIa, when $Y^m$ is not $Y^n$; or

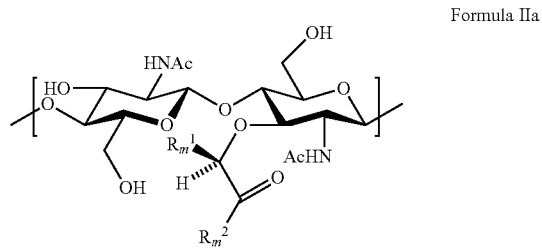

Formula IIa (b) a group of Formula IIb, when $Y^m$ is $Y^n$

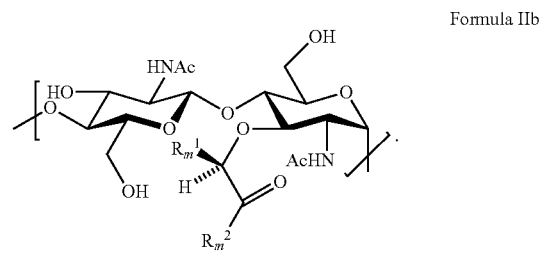

Formula IIb

Each monomeric unit of Formula $Y^m$ comprises an independent set of variables: $R_m^1$ and $R_m^2$, as illustrated below:

| Monomeric Unit: $Y^m$ | Variables of $Y^m$: $R_m^1$ and $R_m^2$ |
|---|---|
| $Y^m$ | $R_m^1$, and $R_m^2$ |
| $Y^1$ | $R_1^1$ and $R_1^2$ |
| $Y^2$ | $R_2^1$ and $R_2^2$ |
| $Y^3$ | $R_3^1$ and $R_3^2$ |
| $Y^{375}$ | $R_{375}^1$ and $R_{375}^2$ |

Thus, a polymer comprising n monomeric $Y^m$ units (i.e., $Y^1$, $Y^2$, $Y^3$, . . . , $Y^{n-1}$ and $Y^n$) will have two sets of variables:

Set 1: $R_1^1$, $R_2^1$, $R_3^1$, . . . , $R_{n-1}^1$ and $R_n^1$

Set 2: $R_1^2$, $R_2^2$, $R_3^2$, . . . , $R_{n-1}^2$ and $R_n^2$

Within each set, the variables are independently selected to be all the same, all different, or any combination thereof. That is, each of $R_1^1$, $R_2^1$, $R_3^1$, . . . , $R_{n-1}^2$ and $R_n^2$ is independently selected. Likewise, each of $R_1^2$, $R_2^2$, $R_3^2$, . . . , $R_{n-1}^2$ and $R_n^2$ is independently selected.

An example of a polymer of Formula I, where n=2, is shown below:

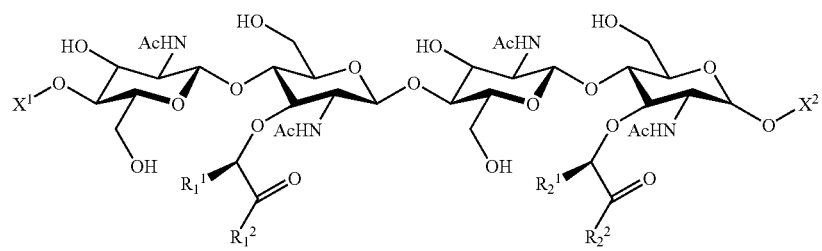

where $R_1^1$ and $R_2^1$ are independently selected and $R_1^2$ and $R_2^2$ are independently selected.

Similarly, when n=3 the polymer of Formula I is shown below:

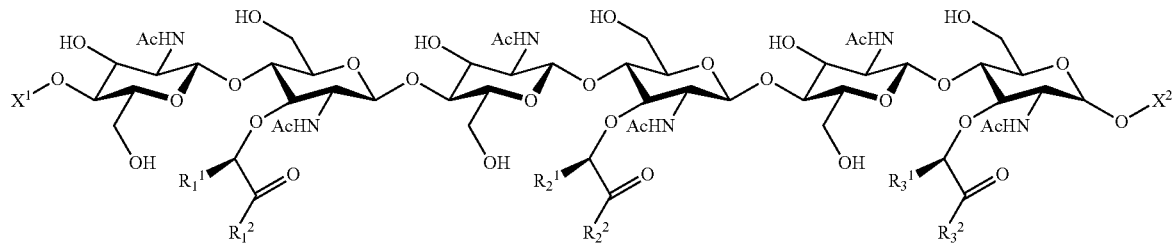

where $R_1^1$, $R_2^1$, and $R_3^1$ are independently selected and $R_1^2$, $R_2^2$ and $R_3^2$ are independently selected.

The disaccharide monomers GMDP (N-acetylglucosaminyl-N-acetylniuramyl-L-alanyl-D-isoglutamine) and GMDP-A (N-acetylglucosaminyl-N-acetylmuramyl-L-alanyl-D-glutamic acid), of the following structures:

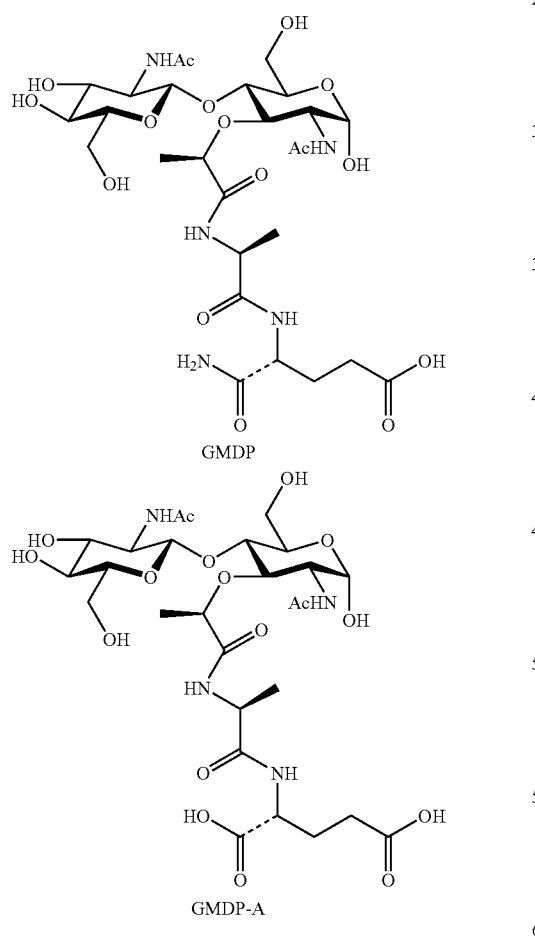

have been reported to induce an inflammatory response (see, e.g., U.S. Pat. No. 4,395,399). Similarly, commercially available samples of polymeric bacterial peptidoglycan (*Staphylococcus aureus*, Sigma; *Streptococcus pyogenes*, Lee Laboratories) are potently inflammatory (*Staphylococcus*>*Streptococcus*). While these materials are heterogeneous in composition, smaller disaccharide fragments (some of which have peptide crosslinks) have been purified by HPLC and characterized, and are also inflammatory. The inflammatory potency of these materials is reportedly dependent on structure (Tuomanen et al. (1993) *J. Clin. Invest.* 92:297). The smallest fragment of peptidoglycan that reportedly has biological activity is muramyl dipeptide, or MDP, and its biological activity is inflammatory in nature (Chedid (1983) *Microbio. Immunol.* 27:723). In fact, the MDP and MDP-A motifs, shown below, are a common feature of known inflammatory compounds:

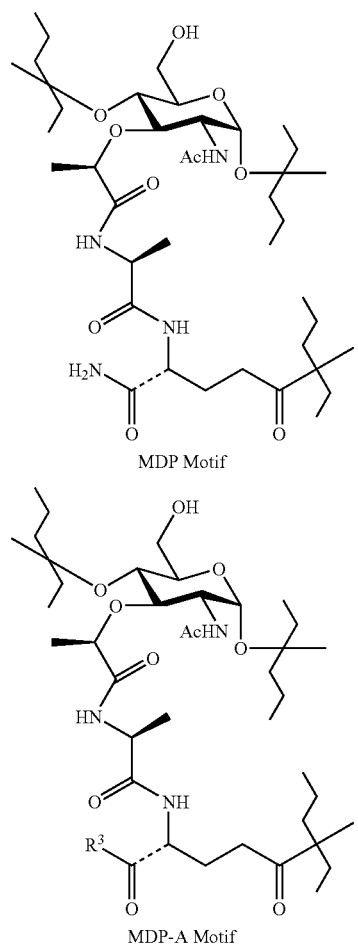

Applicants have discovered that, at a minimum, compounds of Formula I must include one of the following motifs to induce an inflammatory response:

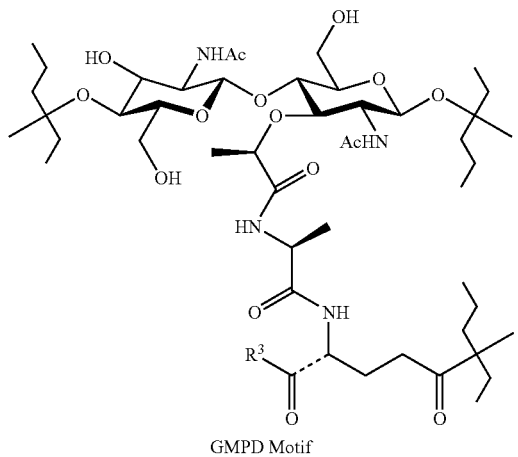

GMPD Motif

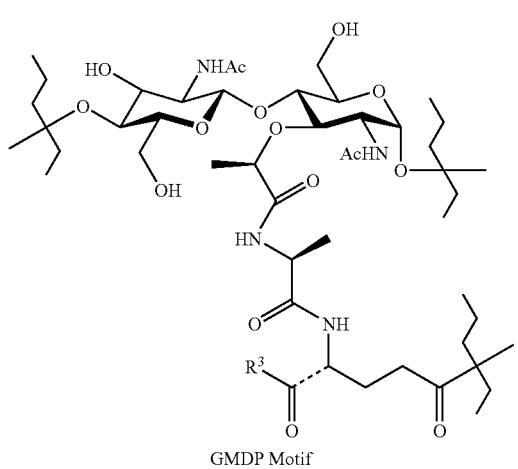

GMDP Motif

If these motifs are absent or modified, the polymer will induce an anti-inflammatory response. If the second amino acid (D-iso-Glu or D-iso-Gln) is missing the pendant carboxyl, or if the pendant carboxyl is of the L configuration, inflammatory activity is abolished (Girardin et al. (2003) *J. Biol. Chem.* 278:8869). Addition of one or more of the remaining three amino acids (Lys-D-Ala-D-Ala) results in retention of activity. We show below that Compound 2 produces pro-inflammatory responses from human peripheral blood mononuclear cells. Its polymeric structure is -[NAG-NAM]$_n$-tripeptide, wherein n is an integer whose distribution is centered around ca. 135, and the tripeptide is a native bacterial sequence (Ala-D-iso-Glu-Lys). Furthermore, we show below that Compound 1 produces anti-inflammatory responses in a number of biological systems. This molecule is the same as Compound 2 except that the second amino acid is missing its pendant carboxyl.

Some of the compounds of Formula I also induce an inflammatory response, for example, where one or more of the monomeric units of Formula $Y^m$ is:

(a) a group of Formula IIa, when $Y^m$ is not $Y^n$; or

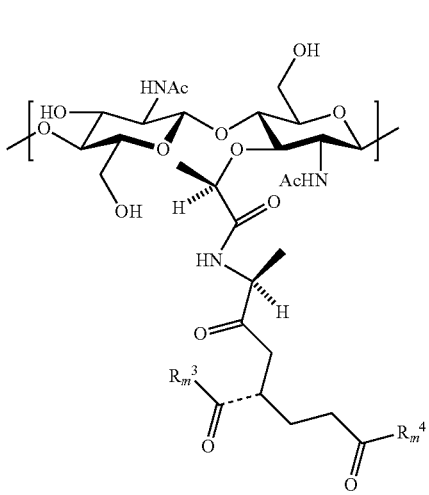

Formula IIIa (b) a group of Formula IIIb, when $Y^m$ is $Y^n$

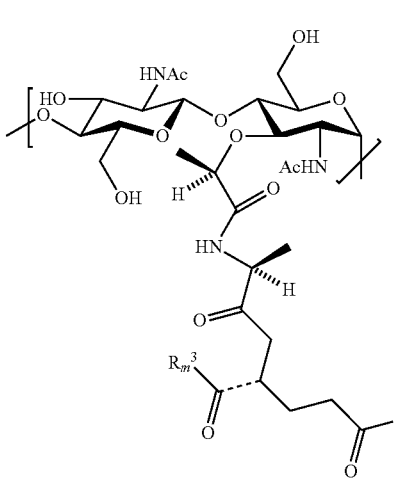

Formula IIIb wherein:
  each of $R_1^3, R_2^3, \ldots R_{n-1}^3$ and $R_n^3$ is independently —OH or —NH$_2$;
  each of $R_1^4, R_2^4, \ldots R_{n-1}^4$ and $R_n^4$ is independently —OH or —NH$_2$, an amino acid residue, or a peptide comprising 2 to 8 amino acid residues, wherein:
    (c) each amino acid residue is independently in the D or L configuration;
    (d) each amino acid residue is unsubstituted or substituted with one or more groups selected from halo, alkyl, hydroxy, alkoxy, phenoxy, CF$_3$, amino, alkylamino, dialkylamino, —C(O)Oalkyl and —NO$_2$; and
    (e) the amino acid residues are independently joined at the α or γ carboxyl groups, and at the α or ε amino groups, or any combination thereof.
These inflammatory compounds are referred to herein as compounds of Formula V. Examples include Compound 2 as described herein and polymers of GMDP and GMDP-A In contrast, some of the compounds of Formula I induce an anti-inflammatory response, for example, where none of the monomeric units of Formula $Y'''$ is:

(a) a group of Formula IIa when $Y'''$ is not $Y''$; or

Formula IIIa

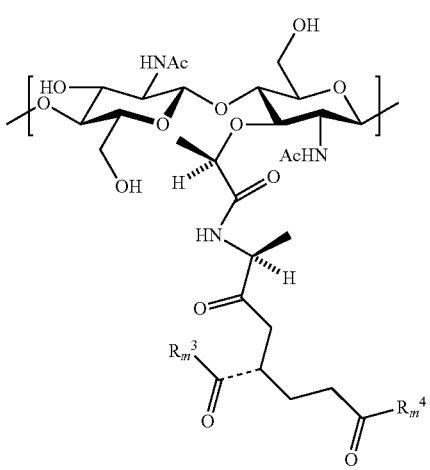

(b) a group of Formula IIIb when $Y'''$ is $Y''$

Formula IIIb

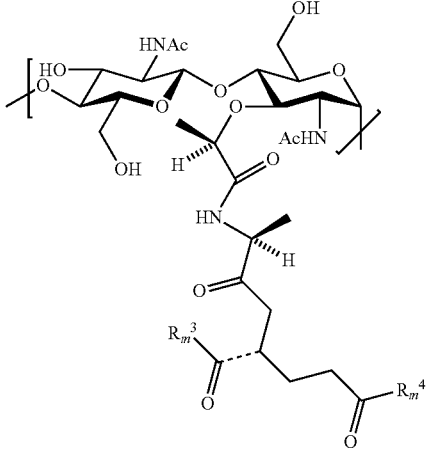

wherein:

each of $R_1^3, R_2^3, \ldots R_{n-1}^3$ and $R_n^3$ is independently —OH or —NH$_2$;

each of $R_1^4, R_2^4, \ldots R_{n-1}^4$ and $R_n^4$ is independently —OH or —NH$_2$, an amino acid residue, or a peptide comprising 2 to 8 amino acid residues, wherein:

(c) each amino acid residue is independently in the D or L configuration;

(d) each amino acid residue is unsubstituted or substituted with one or more groups selected from halo, alkyl, hydroxy, alkoxy, phenoxy, CF$_3$, amino, alkylamino, dialkylamino, —C(O)Oalkyl and —NO$_2$; and (e) the amino acid residues are independently joined at the α or γ carboxyl groups, and at the α or γ amino groups, or any combination thereof.

These anti-inflammatory compounds are referred to herein as compounds of Formula VI. While not a compound of the present invention, Compound 1 is an example of an anti-inflammatory compound comprising the groups of Formula IIIa and IIIb.

It should be appreciated that the examples described above are for illustrative purposes only, and are not meant to narrow the scope of the present invention.

Interactions of Bacterial Peptidoglycans and Synthetic Polysaccharide Antigens with Dendritic Cells Most microbial antigens signal the immune system through highly conserved structural motifs referred to as pathogen-associated microbial patterns (PAMPs) (Medzhitov (2001) *Nat. Rev. Immunol.* 135-145). PAMPs interact with Toll-like receptors (TLRs) present on a variety of antigen presenting cells to initiate a signaling cascade that results in the expression of pro-inflammatory cytokines such as IL12 and IL6, and a variety of chemokines (Janeway et al. (2002) *Annu. Rev. Immunol.* 20:197-216). Activation of antigen presenting cells through TLRs, in particular dendritic cells, leads to a maturation process that is characterized by increased expression of surface MHC II molecules and co-stimulatory molecules such as CD80 and CD86 (Chakraborty et al. (2000) *Clin. Immunol.* 94:88-98). This cascade is designed to marshal early defenders of the innate immune system to respond immediately to invasion, and forms the basis for the link to long-standing adaptive immunity through antigen presentation to T cells (Keller (2001) *Immunol. Lett.* 78:113-122) (See FIG. 1). Since Compound 1 is patterned after natural bacterial cell wall-derived peptidoglycan, but is single stranded, one might expect that this polymer would possess PAMPs that can signal through TLRs. Indeed, natural peptidoglycan has been shown to be a ligand for TLR2 (Schwandner et al. (1999) *J. Biol. Chem.* 274:17406-17409). Surprisingly, as shown herein, Compound 1, representative of compounds of Formula VI, does not appear to activate TLR2 or any other TLR tested in either human or rodent cells. This is further evidenced by the lack of expression of IL12, IL6, or other pro-inflammatory cytokines in PBMC cultures stimulated with this compound. In addition, human monocyte-derived dendritic cells are not driven to maturation by stimulation with this compound. Following treatment with Compound 1, immature dendritic cells do not demonstrate the characteristic upregulation in MHC II, CD80, or CD86 on their surface, despite the fact that these cells are considered to be the most potent of antigen presenting cells and avidly internalize these molecules and concentrate them in endocytic vacuoles.

Bacterial lipopolysaccharide (LPS) is a powerful TLR4 agonist (Beulter (2002) *Curr. Top Microbiol. Immunol.* 270: 109-120.), and is commonly used as a maturation signal for immature dendritic cells (Ardavin et al. (2001) *Trends Immunol.* 22:691-700). LPS specifically upregulates co-stimulatory molecules such as CD80 and CD86 on dendritic cells Michelsen et al. (2001) *J. Biol. Chem.* 276:25680-25686). These surface molecules are essential for signaling T cells to elaborate effector functions such as inflammatory responses. When immature dendritic cells are co-cultured with Compound 1 and LPS, CD80 and CD86 are not upregulated, suggesting that compounds of Formula VI should inhibit the maturation of dendritic cells.

Dendritic Cells

Dendritic cells (DCs) are a family of professional antigen presenting cells that are found in virtually every organ. Dendritic cell subtypes have been well defined, and it has been demonstrated that these cell types evolve through several levels of differentiation and maturation throughout their life span (Jonuleit et al. (2001) *Trends in Immunol.* 22:394-400). Immature dendritic cells are characterized by low expression of MHC II molecules, as well as limited expression of the co-stimulatory molecules CD80 and CD86. The expression of these surface molecules is dramatically upregulated in response to inflammatory stimuli such as IFNγ or activation of a TLR through interactions with bacterial antigens. Functionally, immature DCs in the periphery are especially adept at the capture and processing of antigens. Maturing DCs downregulate these activities, and significantly upregulate their ability to stimulate naïve T cells through the presentation of antigen via MHCII and co-stimulation through CD80/86 (Banchereau et al (2000) *Annu. Rev. Immunol.* 18:767-811). Summarized in FIG. 1.

In the absence of inflammation, most peripheral DCs are in an immature state, and it is thought that these cells play a major role in maintenance of peripheral T cell tolerance (recognition of self), induction of T cell anergy, and protection against autoimmunity (Jonuleit et al. (2001) *Trends in Immunol* 22:394-400).

As shown herein, treatment of immature dendritic cells with Compound 1 inhibits their ability to mature, despite the presence of a potent inflammatory stimulus (LPS). The consequences for immune regulation through immature or semi-mature (low CD80 and CD86 expression) dendritic cells are only beginning to be fully appreciated (Lutz et al. (2002) *Trends Immunol.* 23:445-449). It has been suggested that the induction of adaptive immunity versus tolerance or suppression of inflammation may be determined by the ratio of immature or semi-mature DCs to fully mature DCs in the periphery (Jonuleit et al. (2001) *Trends in Immunol.* 22:394-400; Garza et al. (2000) *J. Exp. Med.* 191:2021-2028) Chemotherapeutic maintenance of an immature DC population through treatment with compounds of Formula VI should inhibit the cognate interactions between T cells and DCs, thus preventing the clonal expansion of antigen-specific effector T cells in response to inflammatory stimuli. In view of the entire body of evidence presented herein, however, it is more likely that the immature DCs generated by treatment with compounds of Formula VI will induce a T regulatory cell population that directly inhibits the activity of inflammatory effector T cells, thus affording protection against inflammatory pathologies. Evidence is mounting in the literature that immature DCs induce T regulatory cells in vivo, and further, T regulatory cells have been induced by immature DCs that specifically protect animals from influenza virus infection and prevent rejection in models of transplantation (Jonuleit et al. (2001) *Trends in Immunol.* 22:394-400; Dhodapkar et al. (2001) *J. Exp. Med.* 193:233-238; Thomson et al. (1999) *Transplant. Proc.* 31:2738-2739). In these studies, immature DCs were expanded ex vivo and then administered to animals. Compounds of Formula VI could provide a unique therapy in which autologous or immunologically compatible DCs are rendered chronically immature through ex vivo treatment and then reintroduced into patients to stimulate T regulatory activity.

T Regulatory Cells

Recent studies from several laboratories have demonstrated that the immature dendritic cell is a critical component in the generation of T regulatory cells (Tregs) (Jonuleit et al. (2001) *Trend Immunol.* 22:394-400). T regulatory cells function to maintain peripheral tolerance, protect against autoimmunity, and participate in modulating inflammation to allow for appropriate responses to microbial invasion or tissue damage while protecting the host from deleterious bystander effects (Maloy et al. (2001) *Nat. Immunol.* 2:816-822).

The most intensely studied Treg phenotype is characterized by the constitutive expression of the surface markers CD4 and CD25 (Shevach (2002) *Nat. Rev. Immunol.* 2:389-400). T regulatory cells with this phenotype have been identified both in vitro and in vivo in both rodents (Taylor et al. (2001) *J. Exp. Med.* 193:1311-1317) and man (Jonuleit et al. (2001) *J. Exp. Med.* 193:1285-1294). CD4+CD25+ T cells naturally occur in the peripheral circulation at a frequency of approximately 2-10% (Shevach (2002) *Nat. Rev. Immunol.* 2:389-400). During co-culture of CD4+ CD25− target cells with CD4+ CD25+ T regulatory cells, the T regulatory cells inhibit the proliferation of CD4+ CD25− target cells despite the presence of potent proliferative signals such as anti-CD3 antibodies or allogeneic APCs (Pasare et al. (2003) *Science* 299:1033-1036). To date, there have been no reports describing a definitive chemical means to generate T regulatory cells in vivo. Early studies reported in the literature indicated that CD4+CD25+ Treg cells expressed some IL10 in vitro (Shevach (2002) *Nat. Rev. Immunol.* 2:389-400). Furthermore, in inflammatory models, CD4+ CD25+ cells were unable to inhibit inflammation in IL10 knockout animals (Shevach (2002) *Nat. Rev. Immunol.* 2:389-400). These studies led to the widely held belief that the mechanism of T regulatory anti-inflammatory activity is via the expression of IL10. Elegant studies performed in several laboratories (Jonuleit et al. (2001) *J. Exp. Med.* 193:1285-1294; Levings et al. (2001) *J. Exp. Med.* 193:1295-1302; Dieckman et al. (2001) *J. Exp. Med.* 193:1303-1310) have shown that while CD4+ CD25+ T cells do indeed express IL10 and/or other cytokines, the mechanism by which they suppress inflammatory T cells is dependent on cell-cell contact. In the initial interactions between CD4+ CD25+ T cells and their targets, cytokine expression does not play a role. Recently, this seemingly paradoxical set of observations was clarified by the work of Diekman et al. ((2002) *J. Exp. Med.* 196:247-253). This group has also shown that CD4+CD25+ T cells interact with inflammatory T cells through cell-cell contact. Although the exact nature of the signals transduced by this contact is not yet known, these workers demonstrated that one important consequence of contact is that the target cells, i.e., CD4+CD25− T cells, become anergized, and begin to express high levels of IL10. Since T regulatory cells are relatively rare in the context of the entirety of the immune system, this provides a mechanism to amplify the anti-inflammatory effect, and explains the body of data indicating a role for IL10 in systemic anti-inflammation mediated by CD4+CD25+ T cells.

As shown below, human PBMC cultures treated with Compound 1 do not respond by proliferation when compared to control cultures treated with polyclonal mitogens such as phytohaemagglutinin (PHA) or superantigens such as *Staphylococcus aureus* enterotoxin A (SEA). Furthermore, when Compound 1-treated PBMC cultures are stimulated with anti-CD3 antibodies, there is a marked suppression in the proliferative capacity of the culture compared to that of untreated controls. Microarray analysis further reveals that PBMC cultures treated with Compound 1 and anti-CD3 antibodies selectively upregulate the expression of IL10 and IL19 (an IL10 paralogue) messages in the CD3+ T cell population while downregulating several inflammatory cytokine messages such as IL17 and TNFβ.

Taken together, these data suggest that compounds of Formula VI as exemplified by Compound 1 inhibit the maturation of dendritic cells. Immature dendritic cells have a unique capacity to drive the generation of T regulatory cells. Treg cells may then participate in the inhibition of inflammatory responses through cell-cell signaling as well as through the stimulation of IL10 expression from anergized T cells at the sites of inflammation.

Therapeutic Applications of IL10

The concept of using recombinant IL10 as an immunotherapeutic is widely accepted (Madsen (2002) *Gastroen-* terol. 123:2140-2144; Barnes (2001) *Curr. Opin. Allergy Clin. Immunol.* 1:555-560; Bremeanu et al (2001) *Int. Rev. Immunol.* 20:301-331; St. Clair (2000) *Curr. Dir. Autoimmun.* 2:126-149). There are numerous animal models of inflammation in which IL10 has been shown to be efficacious, e.g., inflammatory bowel disease (IBD), Crohn's disease, rheumatoid arthritis, autoimmune diabetes, and allergic disease (Madsen (2002) *Gastroenterol.* 123:2140-2144; Barnes (2001) *Curr. Opin. Allergy Clin. Immunol.* 1:555-560; Bremeanu et al (2001) *Int. Rev. Immunol.* 20:301-331; St. Clair (2000) *Curr. Dir. Autoimmun.* 2:126-149). Clinical trials using recombinant IL10 for the treatment of inflammatory bowel disease have, however, met with mixed results. Requirements for repeated high dose regimens, as well as some resulting toxicity, have hampered the success of these efforts. Harnessing an individual's immune system to selectively produce endogenous IL10 via T regulatory activity may provide a better route to immunotherapy. Expression of endogenous IL10, modulated by the host within the entirety of the immune system, may provide the appropriate context to achieve efficacy without the requirement for repeated dosing or the problems of cytokine toxicity. Furthermore, the selective enhancement of a cell population may prove to be the ideal delivery system for such a potent cytokine. Inherent in the immune cell repertoire is the ability to traffic within the body to sites of inflammation. An immune cell population that has been given a specific trafficking signal via a Formula VI compound-tolerized dendritic cell may populate specific sites and locally induce IL10 expression. This therapeutic approach would avoid the problems associated with systemic administration of potent cytokines and better mimic the naturally localized action of this immune mediator.

Intra-Abdominal Abscesses

The formation of intra-abdominal abscesses is the consequence of contamination of the peritoneal cavity with colonic bacteria. This usually occurs during trauma or surgical interventions. Bacteria stimulate a vigorous inflammatory response, resulting in the recruitment of macrophages, polymorphonuclear leukocytes (PMNs), and lymphocytes, and the release of a variety of inflammatory mediators such as IL1β, TNFα, TNFβ, IL17, as well as a number of chemokines (Whal. et al. (1986) *J. Exp. Med.* 163:884-891; Tzianabos et al. (2002) *Curr. Opin. Micro.* 5:92-95). One possible outcome of this response is the encapsulation of invading bacteria by a variety of immune cells interlaced with deposits of fibrin. Once formed, the abscess is relatively resistant to antibiotic therapy, and patients often require surgical intervention to drain the abscess. Although prophylactic antibiotics are given to patients at risk, these interventions are not fully successful. A method to prevent the initial formation of an abscess by modulation of the host response through T regulatory cell activity and the expression of IL10 represents a better form of therapy that could become a standard of care for at risk surgical procedures.

Post-Surgical Adhesions

Post-surgical adhesions are a significant complication of abdominal, gynecologic, orthopedic, and cardiothoracic surgeries. In the abdomen and pelvic cavity, adhesions are associated with considerable morbidity and can be fatal. In preclinical models, exogenously administered IL10 has been shown to limit the formation of adhesions (Laan. et al. (1999). *J. Immunol.* 162:2347-2352; Chung et al. (2002). *J. Exp. Med.* 195:1471-1476). Current therapies in human medicine are, however, designed to interrupt the formation of adhesions after surgical insult. These products involve the introduction of gels or barrier products into the surgical site. These devices have met with only limited success due to enhanced infection rates; lack of efficacy, and relatively low rates of use within the medical community. Better methods to prevent the formation of adhesions are urgently needed.

Like abscess formation, current evidence suggests that the formation of adhesions also involves activation of inflammatory processes, most notably the consistent expression of the inflammatory mediator, IL17, and the deposition of fibrin and other matrix proteins. Together, these processes define a unique intersection between the immune system and pathways of fibrinogenesis and wound repair.

Delayed Type Hypersensitivity Assay for Use as a Clinical Study Biomarker

In view of the hypothesis that Compound 1 may elicit its protective effects through the response of a T regulatory population to inflammatory stimuli, there is a need to develop a specific assay to measure this activity for clinical studies. Early phase clinical trials typically employ healthy volunteers for safety and dose response assessment, a scenario that does not necessarily include the induction or measurement of a specific inflammatory pathology. It is therefore necessary to develop a surrogate biomarker for the activity of these compounds. Delayed Type Hypersensitivity (DTH) reactions in the skin have been used for decades to assess exposure to *Mycobaterium tuberculosis* (TB) in humans, and more recently to determine the state of T cell responsiveness in the face of immunocompromise (Anderson et al. (1968) *Immunology* 15:405-409; Gray et al (1994) *Curr. Opin. Immunol.* 6:425-437; Kuby et al. (2000) *Immunology*, W. H. Freeman and Co.) Studies in the literature have demonstrated that the DTH response is primarily mediated by T cells and that the inflammatory activity can be adoptively transferred to naïve animals by DTH T cells alone (Elices et al. (1993) *Clin. Exp. Rheumatol.* 11:s77-s80). As disclosed herein, a Guinea pig model of DTH has been developed to assess the ability of compounds of Formula VI to limit the localized inflammatory reaction in the skin. Direct measurements of the DTH response can be readily observed and measured in humans and Guinea pigs. Flares, wheals, and/or indurations can be observed and readily measured quantitatively on the surface of the skin. The antigen used to elicit inflammatory T cell activity in this assay, derived from *Candida albicans* (Candin), is currently being used clinically to measure immune competence in individuals undergoing transplant therapies or suffering from AIDs. This antigen is also considered to be safer for the general population than TB antigens. Since it has been reported in the literature that CD4+ CD25+ T regulatory cells are essential components of the memory and protective immunity to *C. albicans* (Montagnoli et al. (2002) *J. Immunol.* 169:6298-6308), these results would provide further evidence that the protective effects of compounds of Formula VI are derived from T regulatory activity.

Mechanism of Action of Synthetic Polysaccharide Antigens of Formula VI: The T Regulatory Cell Hypothesis Disclosed below are detailed investigations into the mechanism(s) by which immunomodulatory molecules such as the synthetic polysaccharide antigen Compound 1 direct and elicit anti-inflammatory effects in mammals, including the induction of T regulatory cell populations. From these studies, the following picture, summarized in FIG. 2, has emerged.

Figure 2:
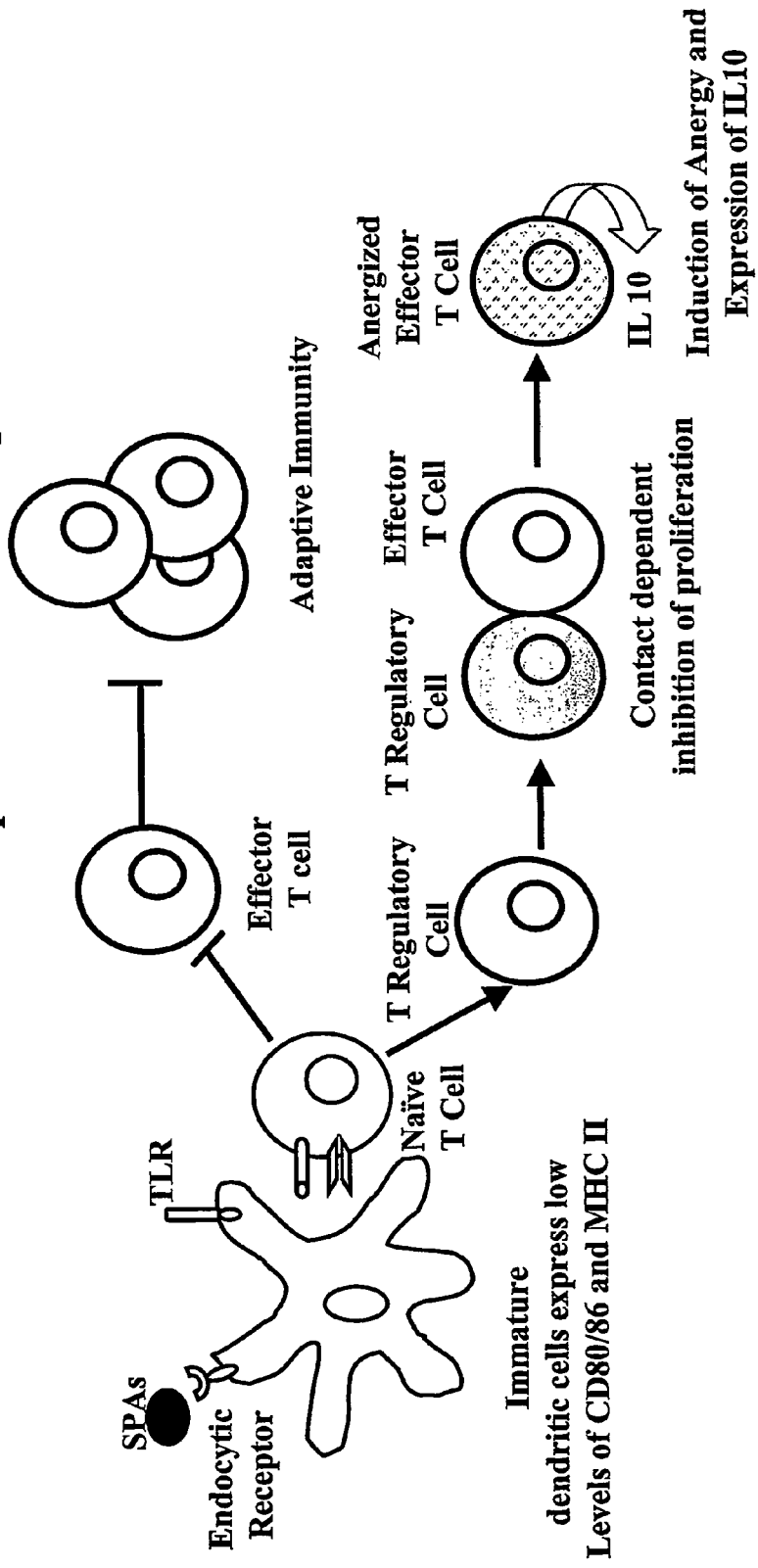
FIG. 2 is a schematic showing the T regulatory cell hypothesis of the present invention.

As depicted in FIG. 2, synthetic immunomodulatory polysaccharide antigens of Formula VI as exemplified by Compound 1 inhibit the maturation of dendritic cells. Immature dendritic cells (iDCs) express low CD80 and CD86 co-stimulatory molecules. In this state, iDCs have the unique ability to interact with naïve T cells and induce the generation of CD4+ CD25+ T regulatory cells (pathway B). In the face of an inflammatory response, T regulatory cells interact with T effector cells through cell-cell dependent contact and inhibit the proliferative capacity of these T inflammatory effector cells. Further, contact between T regulatory cells and T effector cells renders the effectors anergic and stimulates these cells to express large amounts of IL10. Elicitation of IL10 expression in the former inflammatory T cell effectors serves to amplify the suppressive effects of direct T regulatory cell contact and broadens the protection against an ongoing inflammatory process. The inhibition of maturation of dendritic cells observed by the present investigators could also inhibit the clonal expansion of T effector cells through the lack of cognate interactions between these two cell types (pathway A). However, the data presented herein more compellingly support the hypothesis that T regulatory cells are ultimately generated by the synthetic polysaccharide antigens of Formula VI of the present invention and afford protection against inflammatory pathologies.

Figure 8:
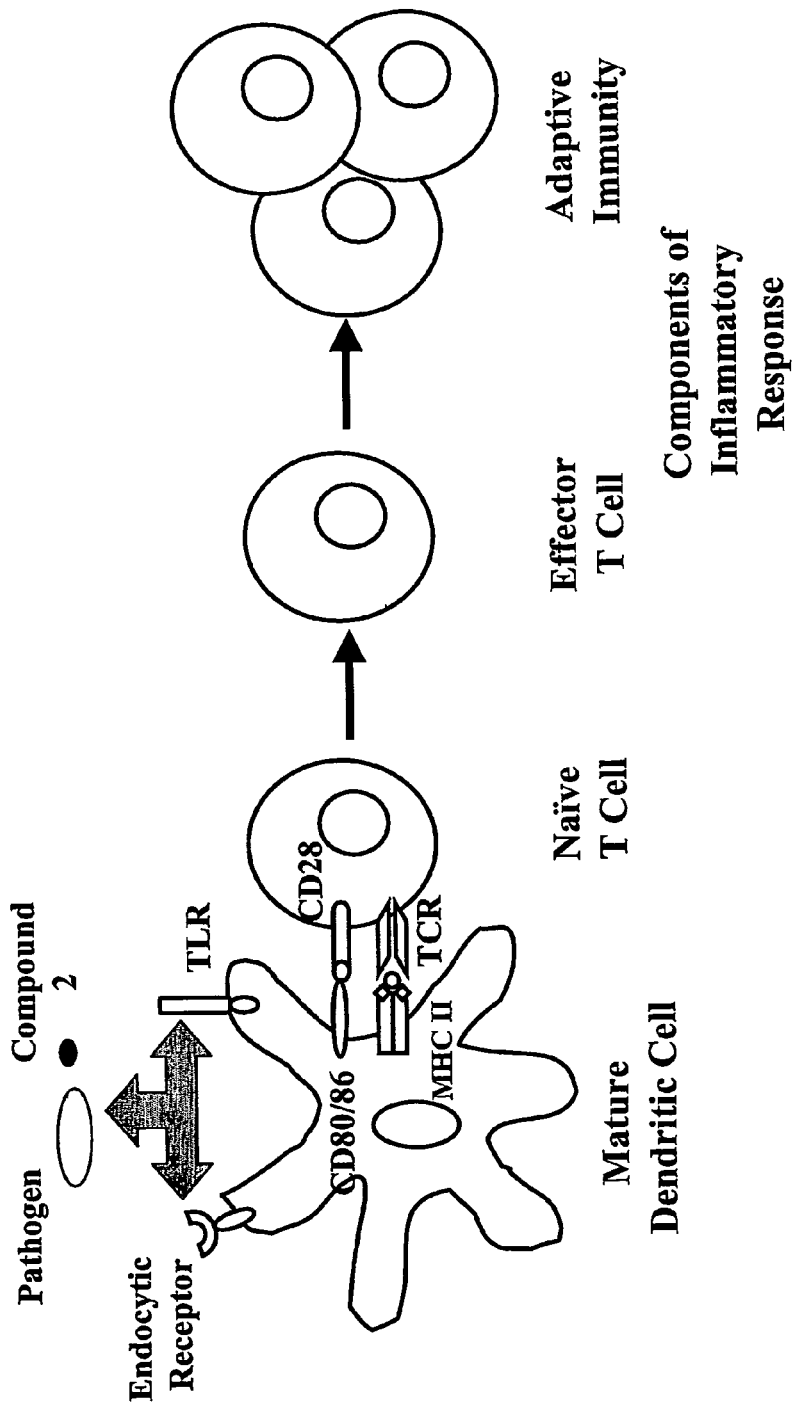
FIG. 8 is a schematic showing the events that may occur when interactions between Compound 2, dendritic cells, and T cells lead to inflammation or adaptive immunity.

Mechanism of Action of Synthetic Polysaccharide Antigens of Formula V: The Inflammatory Hypothesis Compounds of Formula V, exemplified by Compound 2, appear to stimulate an inflammatory response as evidenced by the production of TNF-α. Compound 2 may interact with immune cells in a fashion similar to that of either whole bacteria or bacterial cell wall antigens, most likely through the activation of TLR2. In this case, interactions between compounds of Formula V and TLR2-bearing cells stimulate characteristic markers of inflammation. This would suggest that inflammatory cells would come into play, as is the case following the detection of an invading pathogen. These concepts are summarized in FIG. 8.

Pharmaceutical Compositions and Their Formulation

Depending on their structure, the compounds of Formula I disclosed herein can be used either to prevent or treat inflammatory pathologies or to induce inflammation in connection with various disease states or conditions in which such inflammation provides a beneficial treatment or prophylactic effect in humans and other animals. Thus, in one aspect, the present invention provides pharmaceutical compositions for human and veterinary medical use comprising a compound of Formula I, or a pharmaceutically acceptable salt thereof, together with one or more pharmaceutically or physiologically acceptable buffers, carriers, excipients, or diluents, and optionally, other therapeutic agents. It should be noted that compounds of the present invention can be administered individually, or in mixtures comprising two or more compounds. The present invention also encompasses the use of a compound of Formula I, or a pharmaceutically acceptable salt thereof, for the preparation of a medicament for the prevention or treatment of an inflammatory pathology, or a disease state or condition in which an inflammatory immune response is beneficial. Choice of a compound of Formula V or VI for these uses depends upon which type of immune response is desired for therapeutic purposes.

The compounds of the present invention can be administered in pharmaceutically or physiologically acceptable solutions that can contain pharmaceutically or physiologically acceptable concentrations of salts, buffering agents, preservatives, compatible carriers, diluents, excipients, dispersing agents, etc., and optionally, other therapeutic ingredients. Compound 1 disclosed herein is soluble up to ca. 20 mg/mL in water at neutral pH. Furthermore, aqueous solutions of this compound can accommodate low (about 0.5 to about 5) weight percentages of glycerol, sucrose, and other such pharmaceutically acceptable excipient materials. Compound 1 disclosed herein and other compounds of the present invention can thus be formulated in a variety of standard pharmaceutically acceptable parenteral formulations.

Net Charge and Aggregation

Balanced charge zwitterionic molecules of the present invention having equal numbers of positive and negative charges per repeat unit can, over time, aggregate with one another and/or compress intramolecularly due to charge-charge attractive forces. Compound 1 disclosed herein is a representative balanced charge zwitterionic molecule that, as shown below, exhibits desirable anti-inflammatory activity. Retention of anti-inflammatory immunomodulatory activity over time by molecules of this type in pharmaceutical compositions can be optimized by formulation techniques that minimize aggregation, such as the inclusion of surfactants or dispersing agents, e.g., polyethylene glycol, glycerol, sucrose, etc.

Advantageously, linear macromolecules of the present invention possessing a net positive or negative charge per repeat unit at physiological pH due to their peptidic moieties maintain charge-charge repulsion. Such molecules therefore exhibit ideal solution behavior, i.e., an extended solution state with minimal intramolecular or intermolecular aggregation, events which may diminish immunological activity over time, especially at low ionic strength. Therefore, molecules of the present invention with a net positive or negative charge per repeat unit will behave as polyelectrolytes, and possess the advantage that they will exhibit enhanced solution, and therefore storage, behavior. The polyelectrolyte charge-charge repulsion phenomenon has been observed directly by atomic force microscopy (AFM) for poly(2-vinylpyridine) (Minko et al. (2002) *J. Am. Chem. Soc.* 124:3218). Furthermore, the immunomodulatory activities of synthetic polysaccharide antigens of Formulae-V and VI exhibiting a net positive or negative charge per repeat unit are significantly enhanced by the intra- and intermolecular charge-charge repulsive forces that keep these molecules from aggregating, facilitating proper display of their structural features to cellular receptors.

The pharmaceutical compositions of the present invention can contain an effective amount of the presently disclosed compounds, optionally included in a pharmaceutically or physiologically acceptable buffer, carrier, excipient, or diluent. The term "pharmaceutically or physiologically acceptable buffer, carrier, excipient, or diluent" means one or more compatible solid or liquid fillers, dilutants, or encapsulating substances that are suitable for administration to a human or other animal. The term "carrier" denotes an organic or inorganic ingredient, natural or synthetic, with which the active ingredient is combined to facilitate the application. The components of the pharmaceutical compositions are capable of being commingled with the polymers of the present invention, and with each other, in a manner such that there is no interaction that would substantially impair the desired pharmaceutical efficiency of the active compound(s).

Compositions suitable for parenteral administration conveniently comprise sterile aqueous preparations, which can be isotonic with the blood of the recipient. Among the acceptable vehicles and solvents are water, Ringer's solution, and isotonic sodium chloride solution. In addition, sterile, fixed oils are conventionally employed as a solvent or suspending medium. For this purpose, any bland fixed oil can be employed, including synthetic mono- or diglycerides. In addition, fatty acids such as oleic acid are useful in the preparation of injectables. Carrier formulations suitable for subcutaneous, intramuscular, intraperitoneal, intravenous, etc. administrations can be found in *Remington: The Science and Practice of Pharmacy*, 19$^{th}$ Edition, A. R. Gennaro, ed., Mack Publishing Co., Easton, Pa., (1995).

The compositions can be conveniently presented in unit dosage form or dosage unit form, and can be prepared by any of the methods well known in the art of pharmacy. All methods include the step of bringing the compound into association with a carrier that constitutes one or more accessory ingredients. In general, the compositions are prepared by uniformly and intimately bringing the compound into association with a liquid carrier, a finely divided solid carrier, or both, and then, if necessary, shaping the product. Compounds of the present invention can be stored lyophilized.

Other delivery systems can include time-release, delayed-release, or sustained-release delivery systems. Such systems can avoid repeated administrations of the anti-inflammatory or inflammatory agent, increasing convenience to the subject and the physician. Many types of release delivery systems are available and known to those of ordinary skill in the art, including polymer-based systems such as poly(lactide-glycolide), copolyoxalates, polycaprolactones, polyesteramides, polyorthoesters, polyhydroxybutyric acid, and polyanhydrides.

Microcapsules of the foregoing polymers containing drugs are described in, for example, U.S. Pat. No. 5,075,109. Delivery systems also include non-polymer systems such as: lipids, including sterols such as cholesterol, cholesterol esters, and fatty acids or neutral fats such as mono-, di-, and tri-glycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The present invention encompasses pharmaceutical compositions comprising the presently described immunomodulating polymers in combination with an antibacterial agent or other therapeutic agent, and a pharmaceutically acceptable buffer, carrier, excipient, or diluent. The immunomodulatory polymers of the present invention can be delivered separately with another anti-bacterial antibiotic drug(s), or in the form of anti-bacterial antibiotic cocktails. An anti-bacterial antibiotic cocktail is a mixture of a molecule of the present invention and an anti-bacterial antibiotic drug and/or supplementary potentiating agent. The use of antibiotics in the treatment of bacterial infection is routine in the art. In this embodiment, a common administration vehicle (e.g., tablet, implant, injectable solution, etc.) can contain both a natural or synthetic polysaccharide antigen and the anti-bacterial antibiotic drug and/or supplementary potentiating agent. Alternatively, the anti-bacterial antibiotic drug can be separately dosed.

Non-limiting examples of anti-bacterial antibiotic drugs useful in the present invention include: penicillin G, penicillin V, ampicillin, arnoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefmenoxine, ceftriaxone, moxalactam, cefotetan, cefoperazone, ceftazidme, imipenem, clavulanate, timentin, sulbactam, neomycin, oritavancin, erythromycin, metronidazole, chloramphenicol, clindamycin, lincomycin, vancomycin, trimethoprim-sulfamethoxazole, aminoglycosides, quinolones, tetracyclines, and rifampin. Note *Goodman & Gilman's The Pharmacological Basis of Therapeutics*, Ninth Edition, Hardman et al., Eds., McGraw-Hill, New York, (1996) in this regard. The precise amounts of the therapeutic agent used in combination with the immunomodulatory polymers of the present invention will depend upon a variety of factors, including the polymer itself, the dose and dose timing selected, the mode of administration, the nature of any surgery that may be contemplated, and certain characteristics of the subject. Where local administration is carried out, it will be understood that very small amounts may be required (nanograms, or possibly picograms). The precise amounts selected can be determined without undue experimentation, particularly since a threshold amount will be any amount that will favorably enhances the desired immune response. A dose in the range of from about one picogram to about one milligram may be efficacious, depending upon the mode of delivery; a dose in the range of from about one nanogram to about one microgram may also be useful.

Dosing Treatment Regimen, and Administration

Appropriately selected compounds of the present invention can be administered in an effective amount for either inducing protection against a wide variety of different inflammation-based pathologies, including post-surgical adhesions and intra-abdominal abscesses associated with bacterial infection, or for inducing inflammation in connection with various disease states or disorders in which such inflammation provides a beneficial treatment or prophylactic effect. For such purposes, an effective amount is that amount of an anti-inflammatory or inflammatory compound of the present invention that will, alone or together with further doses or additional therapeutic compounds, either inhibit, ameliorate, or prevent the inflammation-based pathology, or stimulate a therapeutically beneficial inflammatory response, respectively. The dose range can be from about one picogram/kilogram bodyweight to about one milligram/kilogram bodyweight, or from about one nanogram/kilogram bodyweight to about one microgram/kilogram bodyweight. The absolute amount will depend upon a variety of factors, including the nature of the disease or disorder to be treated, whether the administration is in conjunction with elective surgery or emergency surgery, concurrent treatment, the number of doses, individual patient parameters including age, physical condition, size and weight, and the severity of the disease or disorder to be treated, and can be determined by the medical practitioner with no more than routine experimentation. It is generally preferred that a maximum dose be used, that is, the highest safe dose according to sound medical judgment. Multiple doses of the pharmaceutical compositions of the invention are contemplated.

Determination of the optimal amount of compound to be administered to human or animal patients in need of prevention or treatment of an inflammation-based pathology, or a disease or disorder which benefits from immune system stimulation, as well as methods of administering therapeutic or pharmaceutical compositions comprising such compounds, is well within the skill of those in the pharmaceutical, medical, and veterinary arts. Dosing of a human or animal patient is dependent on the nature of inflammation-based pathology or other disease or disorder to be treated, the patient's condition, body weight, general health, sex, diet, time, duration, and route of administration, rates of absorption, distribution, metabolism, and excretion of the compound, combination with other drugs, severity of the inflammation-based pathology or other disease or disorder to be treated, and the responsiveness of the pathology or disease state being treated, and can readily be optimized to obtain the desired level of effectiveness. The course of treatment can last from several days to several weeks or several months, or until a cure is effected or an acceptable diminution or prevention of the disease state is achieved. Optimal dosing schedules can be calculated from measurements of drug accumulation in the body of the patient in conjunction with the effectiveness of the treatment. Persons of ordinary skill can easily determine optimum dosages, dosing methodologies, and repetition rates. Optimum dosages can vary depending on the potency of the immunomodulatory polymeric compound, and can generally be estimated based on $ED_{50}$ values found to be effective in in vitro and in vivo animal models. Effective amounts of the present compounds for the treatment or prevention of inflammation-based pathologies or other diseases or disorders to be treated, delivery vehicles containing these compounds, agonists, and treatment protocols, can be determined by conventional means. For example, the medical or veterinary practitioner can commence treatment with a low dose of the compound in a subject or patient in need thereof, and then increase the dosage, or systematically vary the dosage regimen, monitor the effects thereof on the patient or subject, and adjust the dosage or treatment regimen to maximize the desired therapeutic effect. Further discussion of optimization of dosage and treatment regimens can be found in Benet et al., in *Goodman & Gilman's The Pharmacological Basis of Therapeutics*, Ninth Edition, Hardman et al., Eds., McGraw-Hill, New York, (1996), Chapter 1, pp. 3-27, and L. A. Bauer, in *Pharmacotherapy, A Pathophysiologic Approach*, Fourth Edition, DiPiro et al., Eds., Appleton & Lange, Stamford, Conn., (1999), Chapter 3, pp. 21-43, and the references cited therein, to which the reader is referred.

A variety of administration routes are available. The particular mode selected will depend upon which compound is selected, the particular condition being treated, and the dosage required for therapeutic efficacy. Generally speaking, the methods of the present invention can be practiced using any mode of administration that is medically acceptable, meaning any mode that produces effective levels of an immune response without causing clinically unacceptable adverse effects. Preferred modes of administration are parenteral routes, although oral administration can also be employed. The term "parenteral" includes subcutaneous, intravenous, intramuscular, or intraperitoneal injection, or infusion techniques.

In the context of the present invention, the terms "treatment," "therapeutic use," or "treatment regimen" as used herein are meant to encompass prophylactic, palliative, and therapeutic modalities of administration of the immunomodulatory polymers of the present invention, and include any and all uses of the presently claimed compounds that remedy a disease state, condition, symptom, sign, or disorder caused by an inflammation-based pathology or other disease or disorder to be treated, or which prevents, hinders, retards, or reverses the progression of symptoms, signs, conditions, or disorders associated therewith. Thus, any prevention, amelioration, alleviation, reversal, or complete elimination of an undesirable disease state, symptom, condition, sign, or disorder associated with an inflammation-based pathology, or other disease or disorder that benefits from stimulation of the body's immune response, is encompassed by the present invention.

A particular treatment regimen can last for a period of time which may vary depending upon the nature of the particular inflammation-based pathology or other disease or disorder to be treated, its severity, and the overall condition of the patient, and may involve administration of compound-containing compositions from once to several times daily for several days, weeks, months, or longer. Following treatment, the patient is monitored for changes in his/her condition and for alleviation of the symptoms, signs, or conditions of the disorder or disease state. The dosage of the composition can either be increased in the event the patient does not respond significantly to current dosage levels, or the dose can be decreased if an alleviation of the symptoms of the disorder or disease state is observed, or if the disorder or disease state has been ablated.

An optimal dosing schedule is used to deliver a therapeutically effective amount of the compounds of the present invention. For the purposes of the present invention, the terms "effective amount" or "therapeutically effective amount" with respect to the compounds disclosed herein refers to an amount of compound that is effective to achieve an intended purpose, preferably without undesirable side effects such as toxicity, irritation, or allergic response. Although individual patient needs may vary, determination of optimal ranges for effective amounts of pharmaceutical compositions is within the skill of the art. Human-doses can be extrapolated from animal studies (A. S. Katocs, *Remington: The Science and Practice of Pharmacy*, $19^{th}$ Ed., A. R. Gennaro, ed., Mack Publishing Co., Easton, Pa., (1995), Chapter 30). Generally, the dosage required to provide a therapeutically effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any), and the nature and scope of the desired effect(s) (Nies et al., *Goodman & Gilman's The Pharmacological Basis of Therapeutics*, $9^{th}$ Ed., Hardman et al., eds., McGraw-Hill, New York, N.Y., 1996, Chapter 3).

Prophylactic modalities for high risk individuals are also encompassed by the present invention. As used herein, the term "high risk individual" is meant to refer to an individual for whom it has been determined, via, e.g., individual or family history or genetic testing, living or working environment or conditions, etc., that there is a significantly higher than normal probability of being susceptible to an inflammation-based pathology or the onset or recurrence of an associated disease or disorder, or a disease/disorder that will benefit from a stimulation of the body's immune response. For example, a patient could have a personal and/or family medical history that includes frequent occurrences of a particular disease or disorder. As another example, a patient could have had such a susceptibility determined by genetic screening according to techniques known in the art (see, e.g., U.S. Congress, Office of Technology Assessment, Chapter 5 In: *Genetic Monitoring and Screening in the Workplace*, OTA-BA-455, U.S. Government Printing Office, Washington, D.C., 1990, pages 75-99). In the case of viral diseases, environment can be a predisposing factor. As part of a treatment regimen for a high risk individual, the individual can be prophylactically treated to prevent inflammation-based pathologies or the onset or recurrence of the disease, disorder, sign, symptom, or condition, or diseases/disorders that will benefit from an enhanced immune response. The term "prophylactically effective amount" is meant to refer to an amount of a pharmaceutical composition of the present invention that produces an effect observed as the prevention of infection or inflammation, or the onset or recurrence of an inflammatory disease, symptom, sign, condition, or disorder, or a disease/disorder that benefits from a stimulation of the body's immune response. Prophylactically effective amounts of a pharmaceutical composition are typically determined by the effect they have compared to the effect observed when a second pharmaceutical composition lacking the active agent is administered to a similarly situated individual.

For therapeutic use, the immunomodulatory compounds disclosed herein can be administered to a patient suspected of suffering from an inflammation-based pathology in an amount effective to reduce the symptomology of the disease, symptom, sign, condition, or disorder, or suffering from a disease or disorder that will benefit from an enhanced immune response. One skilled in the art can determine optimum dosages and treatment schedules for such treatment regimens by routine methods.

In the case of surgery- or trauma-related abscesses and adhesions, the methods of the present invention can be effectuated by administering multiple doses over a three week period preceding surgery, over a two week period preceding surgery, over a one week period preceding surgery, when the first dose is administered only 24 hours preceding surgery, and even when given only after exposure to bacteria. Further doses can be administered after surgery as well. Any regimen that results in an enhanced immune response to bacterial infection/contamination and subsequent abscess/adhesion formation can be used, although optimal doses and dosing regimens are those which would not only inhibit the development of abscess and/or adhesion formation, but also would result in a complete protection against abscess or adhesion formation by a particular bacterial organism or a variety of bacterial organisms. Desired time intervals for delivery of multiple doses of a particular polymer can be determined by one of ordinary skill in the art employing no more than routine experimentation.

Thus, the present invention is useful whenever it is desirable to prevent bacterial abscess or adhesion formation in a human or animal subject. This includes prophylactic treatment to prevent such conditions in planned surgical procedures, as well as in emergency situations. Elective surgeries include the following intraabdominal surgeries: right hemicolectomy; left hemicolectomy; sigmoid colectomy; subtotal colectomy; total colectomy; laparoscopic or open cholecystectomy; gastrectomy; caesarian section; etc. Emergency surgeries include those to correct the following conditions: perforated ulcer (duodenal or gastric); perforated diverticulitis; obstructive diverticulitis; acute appendicitis; perforated appendicitis; blunt abdominal trauma; penetrating abdominal trauma; second operation to drain abscess; etc. The methods of the present invention encompass colic surgeries in equine species, surgery of any type in companion animals, for example routine sterilization, gastrointestinal invasive procedures, etc. The methods of the present invention are also useful in nonintraabdominal surgeries such as cardiac surgeries and surgeries to correct wound infections. The present methods are also useful in connection with diseases that predispose a subject to abscess formation such as pelvic inflammatory disease, inflammatory bowel disease, urinary tract infections, and colon cancer. The present methods are therefore useful with abscesses of virtually any tissue or organ, including specifically, but not limited to, dermal abscesses such as acne. Those of ordinary skill in the art to which this invention pertains will readily recognize the range of conditions and procedures in which the present invention is applicable.

In another aspect, the present invention includes a method for inducing protection against postoperative surgical adhesion formation associated with many common types of surgery. The method includes the step of administering to a subject in need of such protection a pharmaceutical preparation containing an effective amount for reducing postoperative surgical adhesion formation of the immunomodulating polymer of the present invention. It is fully expected that administration of one or more such polymers at a site separate from the operative site will be effective in inducing protection against postoperative surgical adhesion formation. This is particularly surprising in view of previous observations, as discussed above.

PCT International Publication WO 00/59515 teaches that local administration of certain polymers into the surgical site is effective for reducing the incidence of postoperative surgical adhesions. In accordance with the present invention, an immunomodulatory polymer can be effective when given subcutaneously apart from the surgical site at which adhesions are likely to form.

The presently disclosed compounds can be administered in an effective amount for inducing protection against postoperative surgical adhesion formation. An effective amount for inducing protection against postoperative surgical adhesion formation as used herein is that amount of immunomodulating polymer of the present invention that will, alone or together with further doses or additional therapeutic compounds, inhibit or prevent the formation of postoperative surgical adhesion. It is believed that doses ranging from about one picogram/kilogram bodyweight to about one milligram/kilogram bodyweight, or from about one nanogram/kilogram bodyweight to about one microgram/kilogram bodyweight, will be effective, depending upon the mode of administration. The absolute amount will depend upon a variety of factors (including whether the administration is in conjunction with elective surgery or emergency surgery, concurrent treatment, number of doses, and individual patient parameters including age, physical condition, size and weight), and can be determined via routine experimentation. It is preferred generally that a maximum dose be used, that is, the highest safe dose according to sound medical judgment.

Multiple doses of the pharmaceutical compositions of the present invention are contemplated for inducing protection against postoperative surgical adhesion formation. Such multiple doses can be administered over a three day period beginning on the day preceding surgery. Further doses can be administered post surgery as well. Any regimen that results in a reduced postoperative surgical adhesion formation can be used, although optimum doses and dosing regimens are those which would not only inhibit the development of postoperative surgical adhesion formation, but would also result in complete protection against postoperative surgical adhesion formation. Desired time intervals for delivery of multiple doses of one of the present immunomodulatory polymers can be determined by one of ordinary skill in the art employing no more than routine experimentation.

Thus, the methods disclosed herein are useful whenever it is desirable to prevent postoperative surgical adhesion formation in a human or animal subject. This includes prophylactic treatment to prevent adhesion formation following planned surgical procedures, as well as following emergency operations. Elective surgeries include the following intraabdominal surgeries: right hemicolectomy; left hemicolectomy; sigmoid colectomy; subtotal colectomy, total colectomy; laparoscopic or open cholecystectomy; gastrectomy; pancreatectomy; splenectomy; liver, pancreas, small bowel, or kidney transplantation; lysis of adhesions; etc. Emergency intraabdominal surgeries include those to correct the following conditions: perforated ulcer (duodenal or gastric); perforated diverticulitis; obstructive diverticulitis; bowel obstruction; acute appendicitis; perforated appendicitis; blunt abdominal trauma; penetrating abdominal trauma; second operation to drain abscess; ruptured abdominal aortic aneurysm, etc. The methods of the present invention are also useful in the case of nonintraabdominal surgeries such as cardiac surgeries, open and endoscopic orthopedic surgeries, neurosurgeries, gynecologic and pelvic surgeries, and surgeries to correct wound infections. The present methods are also useful in connection with diseases that predispose a subject to spontaneous adhesion formation, such as pelvic inflammatory disease, inflammatory bowel disease, urinary tract infections, and colon cancer. The present methods are thus useful with inflammatory processes involving virtually any tissue or organ.

When administered to prevent postoperative surgical adhesion formation, the compounds of the present invention can be administered either distant from the operative site, including systemically, or locally into the operative site at which it is desirable to reduce the likelihood of postoperative surgical adhesion formation. The compounds of the present invention can be administered as an aqueous solution, as a crosslinked gel, or as any temporal or physical combination of aqueous solution and crosslinked gel forms.

The preparations of the present invention can be administered "in conjunction with" infection, meaning close enough in time with the surgery, trauma, or diseases that predispose the host to abscess or adhesion formation so that a protective effect against abscess or adhesion formation is obtained. The preparations can be administered long before surgery in the case of elective surgery (i.e., weeks or even months), preferably with booster administrations closer in time to (and even after) the surgery. Particularly in emergency situations, the preparations can be administered immediately before (minutes to hours) and/or after the trauma or surgery. It is important only that the preparation be administered close enough in time to the surgery so as to enhance the subject's immune response against bacterial infection/contamination, thereby increasing the chances of a successful host response and reducing the likelihood of abscess or adhesion formation.

Those of ordinary skill in the art to which this invention pertains will recognize that the present methods can be applied to a wide range of diseases, symptoms, conditions, signs, disorders, and procedures. Besides abscesses and adhesions, other inflammatory processes and pathologies to which the Formula VI anti-inflammatory compounds, compositions, and methods of the present invention can be applied include:

Allergic diseases such as (generalized) anaphylaxis, serum sickness, generalized drug reactions, food allergies, insect venom allergies, and mastocytosis; airway allergies such as allergic rhinitis, asthma, and hypersensitivity pneumonitis; skin allergies such as urticaria, angioedema, eczema, atopic dermatitis, allergic contact dermatitis, infectious dermatitis, erythema multiforme and Stevens-Johnson syndrome; and ocular allergies such as allergic conjunctivitis, atopic keratoconjunctivitis, venereal keratoconjunctivitis, giant papillary conjunctivitis, and contact allergy.

Organ specific autoimmune diseases such as those of the:

Endocrine system: (thyroid gland) Hashimoto's thyroiditis, Graves' disease, thyroiditis with hyperthyroidism; Type I autoimmune polyglandular syndrome, Type II autoimmune polyglandular syndrome, insulin-dependent diabetes mellitus, immune-mediated infertility, and autoimmune Addison's disease.

Skin: pemphigus vulgaris, pemphigus foliaceus, paraneoplastic pemphigus, bullus pemphigoid, dermatitis herpetiformis, linear IgA disease epidermolysis bullosa acquisita, autoimmune alopecia, erythema nodosa, pemphigoid gestationis, cicatricial pemphigoid, and chronic bullous disease of childhood.

Hematologic system: autoimmune hemolytic anemia, autoimmune thrombocytopenic purpura (idiopathic and drug-related); and autoimmune neutropenia.

Neuromuscular system: myasthenia gravis, Eaton-Lambert myasthenic syndrome, Stiff-man syndrome, acute disseminated encephalomyelitis, multiple sclerosis, Guillain-Barré syndrome, chronic inflammatory demyelinating polyradiculoneuropathy, multifocal motor neuropathy with conduction block, and chronic neuropathy with monoclonal gammopathy.

Paraneoplastic neurologic disorders: opsoclonus-myoclonus syndrome, cerebellar degeneration, encephalomyelitis, retinopathy.

Hepatobiliary system: autoimmune chronic active hepatitis, primary biliary sclerosis, and sclerosing cholangitis.

Gastrointestinal tract: gluten-sensitive enteropathy, pernicious anemia, and inflammatory bowel disease.

Organ nonspecific autoimmune diseases such as:

Connective tissue diseases such as systemic lupus erythematosus, rheumatoid arthritis, systemic sclerosis (scleroderma), ankylosing spondylitis, reactive arthritides, polymyositis/dermatomyositis, Sjögren's syndrome, mixed connective tissue disease, Behcet's syndrome, and psoriasis.

Vasculitic syndromes: systemic necrotizing vasculitides, including classic polyarteritis nodosa, allergic angiitis and granulomatosis (Churg-Strauss disease), and polyangiitis overlap syndrome; hypersensitivity vasculitis, Wegener's granulomatosis, temporal arteritis, Takayasu's arteritis, Kawasaki's disease, isolated vasculitis of the central nervous system, thromboangiitis obliterans, and miscellaneous vasculitides; sarcoidosis, graft-versus-host disease, and cryopathies.

Other diseases and conditions in which anti-inflammatory compounds of the present invention are useful include sepsis; colitis; coronary artery disease; hepatic fibrosis; acute respiratory distress syndrome; acute inflammatory pancreatitis; endoscopic retrograde cholangiopancreatography-induced pancreatitis; burns; atherogenesis of coronary, cerebral, and peripheral arteries; appendicitis; cholecystitis; diverticulitis; visceral fibrotic disorders (liver, lung, intestinal); wound healing; skin scarring disorders (keloids, hidradenitis suppurativa); granulomatous disorders (sarcoidosis, primary biliary cirrhosis); pyoderma gangrenosum; Sweet's syndrome; cell, tissue, or organ transplantation; Alzheimer's disease; Parkinson's disease; atherosclerosis; obesity; and cancer.

Diseases and pathologies to which the inflammatory compounds of Formula V, compositions thereof, and methods employing these compounds and compositions can be applied include antiviral therapy, for example treatment or prevention of hepatitis B virus and hepatitis C virus infections; anticancer therapy; and use as vaccine adjuvants.

The foregoing descriptions provide a comprehensive overview of the many aspects of the present invention. The following examples illustrate various aspects thereof and are not intended, nor should they be construed, to be limiting thereof in any way.

EXAMPLE 1

General Preparation of Compounds of Formula I

Compounds of Formula I can be prepared, for example, by polymerizing lipid II substrates of Formula IV:

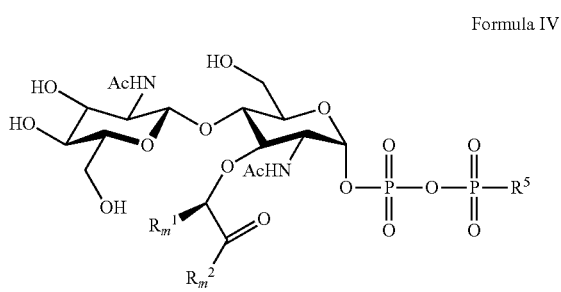

Formula IV where $R^5$ is a lipid carrier and the other variables are as described herein. Suitable lipid carriers include, for example, saturated and unsaturated hydrocarbon chains having more than one carbon. The chains may be straight or branched. The hydrocarbon may also be substituted (e.g., perfluorinated) or unsubstituted. Preferably, the hydrocarbon chain contains from 5 to 55 carbons and 1 to 11 prenyl units, more preferably 25 to 55 carbons and 5 to 11 prenyl units, most preferably 40 to 55 carbons and 8 to 11 prenyl units. Lipid II substrates of formula IV can be prepared, for example, according to the methods described in WO 01/79242 A3, WO 02/085929 A1 and U.S. Pat. No. 6,461,829. The lipid II substrates can be polymerized to produce compounds of Formula I, for example, according to the methods described herein employing the monofunctional transglycosylase MgtA, or employing any of the mono- or bifunctional transglycosylases described in U.S. Pat. No. 6,461,829.

Preparation of Homopolymers of Formula I: General Procedure

A 20 mM stock solution of a lipid II substrate molecule of Formula IV as described herein is prepared. PEG 8000 (as a 50% stock in water) is diluted with water to ca. 20% (w/w). To the PEG solution was added 0.5M HEPES buffer at pH 7.0, 1M aqueous magnesium chloride and lipid II substrate to achieve final concentration of 20 mM, 25 mM and 2 mM, respectively. The resulting solution is brought to homogeneity by thorough mixing. The reaction is initiated by addition of *Staphylococcus aureus* MtgA enzyme stock solution at ca. 120 µM such that the final molar enzyme concentration is 10 µM (ca. 200:1=substrate:enzyme). The reaction solution is mixed well and allowed to stand undisturbed for 24 hr.

The reaction mix is brought to ca. 0.5M in aqueous HCl. The system becomes homogeneous after addition of the acid. The aqueous acidic solution is incubated at 37° C. 4 hr, after which the solution is neutralized to pH 7-8 with 5M aqueous NaOH. At a point near pH 7, the homogeneous solution becomes cloudy. The cloudy solution is centrifuged (1700×g, 20 min). The pellet is washed with water and the supernatants are combined. Aqueous 5M NaOH is added to bring the final concentration to 0.5M. This solution was allowed to stand at room temperature for 2 hr and then neutralized to pH 7 with 5M aqueous HCl at which point the solution becomes turbid. The cloudy solution is centrifuged (1700×g, 20 min). The pellet is washed with water and the supernatants are combined, diluted 2× with water and extracted with chloroform until PEG is absent (Nag et al. (1996) Anal Biochem. 237: 224). The slightly emulsified aqueous layer is centrifuged (1700×g, 20 min) and the clear aqueous layer is removed. The final aqueous solution is placed in an Amicon stirred cell concentrator (10K NMWCO regenerated cellulose), and subjected to concentration/dilution cycles until the effluent conductance is near zero. The solution is then concentrated as much as possible, filtered through a Millipore Steriflip filter (0.2µ), and the concentration of Formula I compound estimated by size exclusion chromatography (UV absorption at 206 nm).

Preparation of Copolymers of Formula I: General Procedure

The rates of polymerization of various lipid II substrate molecules of Formula IV do not vary significantly. As a result, a mixture of different lipids II substrate molecules of Formula IV can be polymerized, thereby affording a copolymer. One skilled in the art will appreciate that, using known procedures, it is possible to prepare copolymers varying in both the number of distinct monomeric units and the frequency at which these units occur. In order to prepare a copolymer, the stock solution should preferably be at a total lipids II substrate molecule concentration of about 20 µM.

For example, a compound of Formula I can be prepared by the action of an enzyme, e.g., MtgA, on a mixture of two distinct lipid II substrate molecules of Formula IV. The relative rate of occurrence of the two distinct monomeric units within the copolymer will depend primarily on their relative concentrations in the solution and secondarily on their relative polymerization rates. Similarly, a compound of Formula I can be prepared by the action of an enzyme, e.g., MtgA, on a mixture of up to 375 distinct lipid II substrate molecules of Formula IV. Likewise, the relative rate of occurrence of any one of the 375 distinct monomeric units within the copolymer will depend primarily on its concentration relative to the other distinct components in the solution and secondarily on its polymerization rate relative to that of the other distinct components in the solution.

Block copolymers of Formula I can be prepared, for example, by allowing an enzyme, e.g., MtgA, to polymerize a single lipid II substrate molecule of Formula IV for a defined period; terminating or stopping this reaction, or removing the formed polymer from the reaction mixture; placing the polymer in a second enzyme solution containing a different single lipid II substrate molecule of Formula IV for a defined period, etc., as would be apparent to one of ordinary skill in the art.

Block copolymers of Formula I can be prepared by the action of an enzyme, e.g., MtgA, on a solution of a single lipid II substrate molecule of Formula IV. The relative rate of occurrence of the two distinct monomeric units within the copolymer will depend primarily on their relative concentrations in the solution and secondarily on their relative polymerization rates. Similarly, a compound of Formula I can be prepared by the action of an enzyme, e.g., MtgA, on a mixture of up to 375 distinct lipid II substrate molecules of Formula IV. Likewise, the relative rate of occurrence of any one of the 375 distinct monomeric units within the copolymer will depend primarily on its concentration relative to the other distinct components in the solution and secondarily on its polymerization rate relative to that of the other distinct components in the solution.

Verification of the Structure of Compounds of Formula I: General Procedure

The structural identity of the compound of Formula I is determined via size exclusion chromatography based on dextran as standard and by $^1$H nmr spectrometry in $D_2O/CD_3CN$. The material is degradable by lysozyme and the disaccharide-peptide lysozyme degradation product can be analyzed by ES/MS.

Preparation of Compound 1

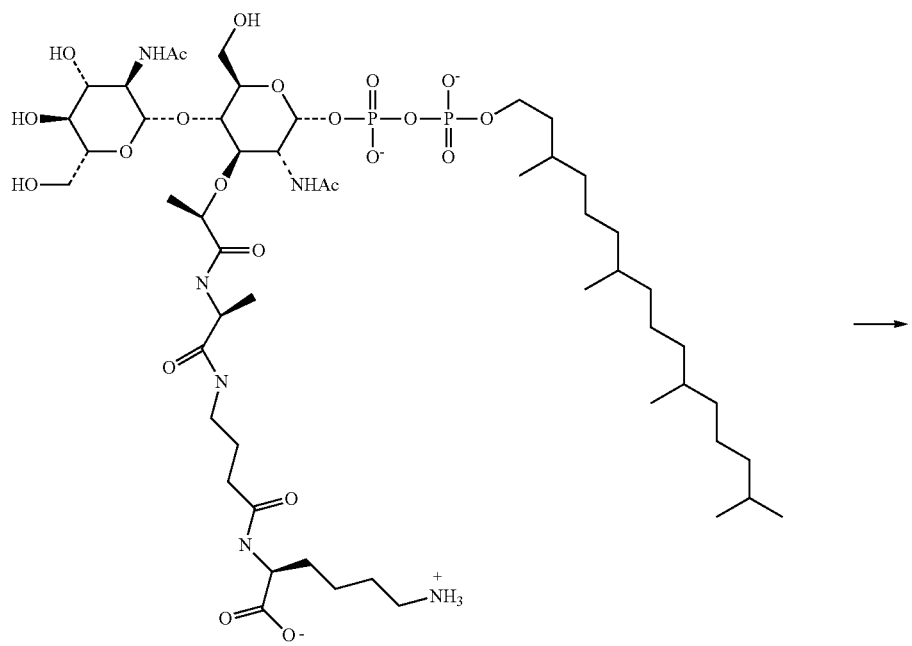

Compound 3

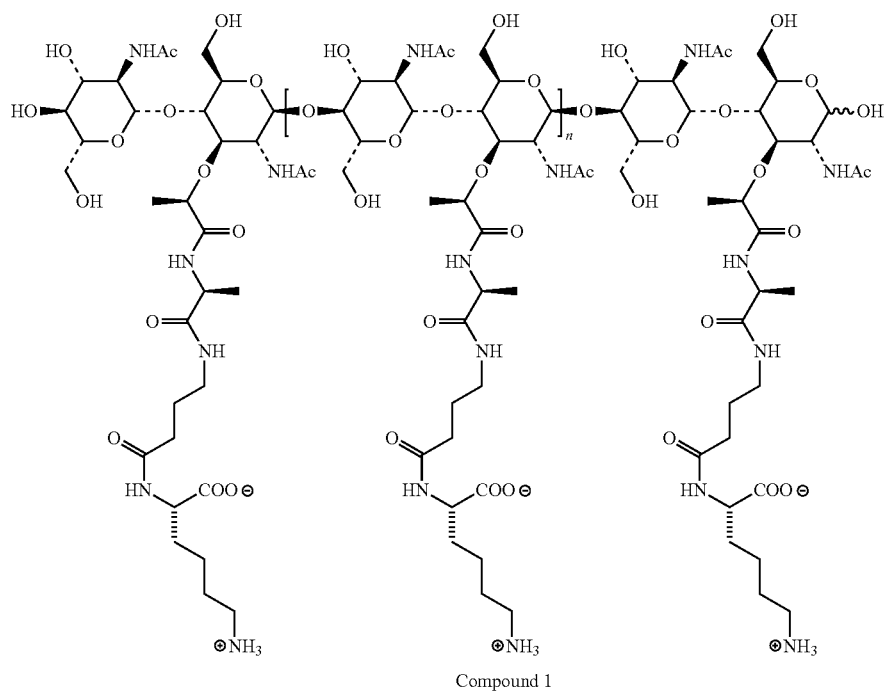

Compound 1

A 20 mM stock solution of Compound 3 is prepared by dissolving the white powder (370 mg) in water (14.5 mL). To water (79.7 mL) is added PEG 8000 (28.8 mL as a 50% stock in water). To this solution is added 0.5M sodium phosphate buffer at pH 7.0 (5.8 mL), 1M aqueous magnesium chloride (3.6 mL). The resulting solution is divided equally among three conical tubes, and to each is added Compound 3 stock solution (4.8 mL) with thorough mixing. The polymerization reaction is initiated by addition of a stock solution of *Staphylococcus aureus* MtgA enzyme (U.S. Pat. No. 5,922,540)

(123 μM; 3.9 mL). The reaction solutions are mixed well and allowed to stand undisturbed for 24 hr.

As the polymer forms, it aggregates and settles to the bottom of the tube. The supernatant is removed and centrifuged (3500 rpm, 20 min) to recover any polymer that has been adventitiously removed with the supernatant. The pellet is dissolved in 0.2M aqueous HCl (5 mL) and taken on to the next step in this form.

To each of the crude polymer suspensions that remains after decanting the supernatant is added 5M aqueous HCl (2×100 μL with mixing after each addition). The system becomes homogeneous after addition of the acid. To the yellowish solutions thus obtained are added the acidified pellet solutions from processing of the original supernatants (vide supra). These aqueous acidic solutions are incubated at 37° C. overnight, after which the tube contents are pooled to a final volume of about 30 mL. The solution is neutralized to pH 7-8 using about 1.2 mL of 5M aqueous NaOH, at which point the homogeneous solution becomes cloudy. The cloudy solution is centrifuged twice (3500 rpm, 20 min), the pellet being washed with water each time and then discarded (final volume of retained supernatant=36 mL).

Aqueous 5M NaOH (3.6 mL) is added to bring the final concentration to 0.5M. This solution is allowed to stand at room temperature for 2 hr and is then neutralized to pH 6 with 5M aqueous HCl. The solution is divided into eight aliquots (8×5 mL, 1×3 mL), each in a 50 mL conical tube. Nine volumes of ethanol are added to each tube and the solutions are stored overnight in the −20° C. freezer. The tubes are centrifuged (3500 rpm, 20 min) and the supernatants carefully removed. After brief drying in vacuo, the pellets are dissolved in minimal aqueous NaCl (100 mM) and pooled to a final volume of 16 mL. Nine volumes of ethanol are again added and the precipitation process repeated. Finally, a third round of precipitation is executed.

The final pellet is dissolved in water (40 mL), placed in an Amicon Model 8050 stirred cell concentrator, and subjected to concentration/dilution cycles until the effluent conductance is near zero. The solution is then concentrated as much as possible, filtered through a pre-washed Millipore Steriflip filter, and lyophilized. Compound 1 is thus isolated as a white solid (144 mg, 66%).

Verification of Compound 1 Structure

The structural identity of Compound 1 is determined by size exclusion chromatography, $^1$H NMR spectroscopy, enzymatic susceptibility and mass spectrometry. Size exclusion chromatography (3.2 mm×30 mm Pharmacia Superose 6 column, 20 mM sodium phosphate buffer at pH=7) indicates the midpoint of the size distribution to be about 150 kilodaltons based on dextran as standard (range about 75 kD to about 375 kD). $^1$H NMR (400 MHz, D$_2$O) δ 4.45 (br s, 1H), 4.32 (br s, 1H), 3.50 (br m, 13H), 2.90 (m, 2H), 2.26 (M, 2H), 1.95 (s, 3H), 1.89 (s, 3H), 1.75 (m, 3H), 1.62 (m, 3H), 1.31 (m, 6H).

Compound 1 is rapidly degraded by lysozyme. Bacterial cell wall glycan polymer, a substructure of peptidoglycan, is the natural substrate for lysozyme. Therefore, lysozyme susceptibility represents-prima facie evidence for the glycan substructure of Compound 1. Finally, the lysozyme hydrolysis product of Compound 1, N-acetylgulcosaminyl-β-[1,4]-N-acetylmuramyl-[Ala-GABA-Lys]-peptide, is confirmed by ES/MS m/z 781.6 [M+H]$^+$, 779.5 [M−H]$^−$.

Preparation of Compound 2

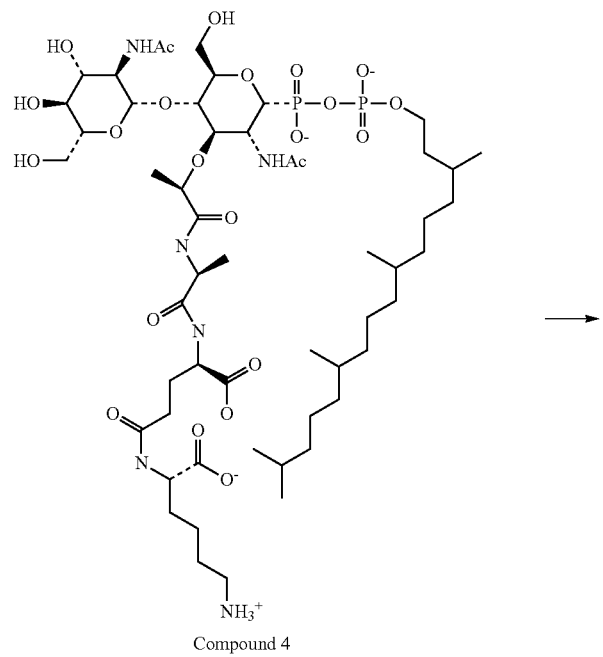

Compound 4

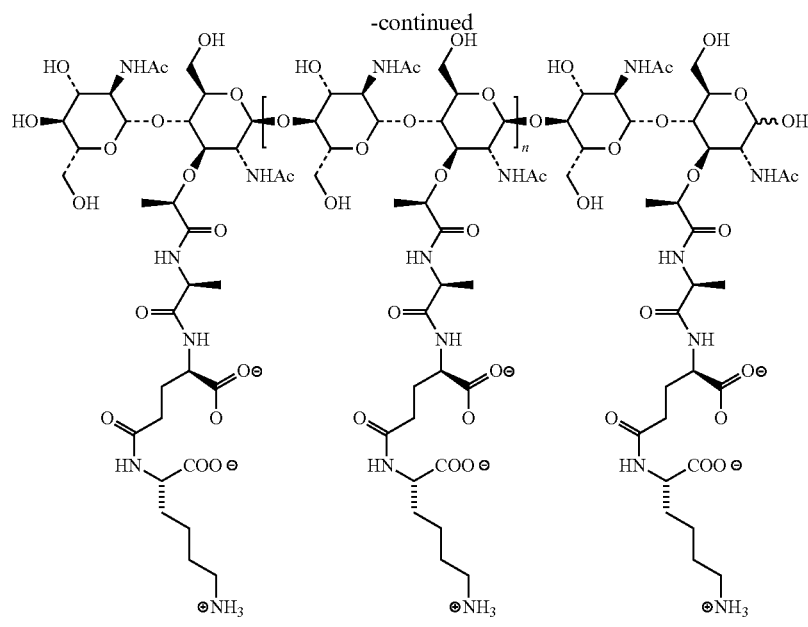

Compound 2

A 20 mM stock solution of Compound 4 is prepared. PEG 8000 (as a 50% stock in water) is diluted with water to ca. 20% (w/w). To the PEG solution is added 0.5M HEPES buffer at pH 7.0, 1M aqueous magnesium chloride and Compound 4 to achieve final concentrations of 20 mM, 25 mM and 2 mM, respectively. The resulting solution is brought to homogeneity by thorough mixing. The reaction is initiated by addition of *Staphylococcus aureus* MtgA enzyme stock solution at ca. 120 µM such that the final molar enzyme concentration is 10 µM (ca. 200:1=substrate:enzyme). The reaction solution is mixed well and allowed to stand undisturbed for 24 hr.

The reaction mix is brought to ca. 0.5M in aqueous HCl. The system becomes homogeneous after addition of the acid. The aqueous acidic solution is incubated at 37° C. 4 hr, after which the solution is neutralized to pH 7-8 with 5M aqueous NaOH. At a point near pH 8, the homogeneous solution becomes cloudy. The cloudy solution is centrifuged (1700×g, 20 min). The pellet is washed with water and the supernatants are combined. The cloudy solution is centrifuged (1700×g, 20 min). The pellet is washed with water and the supernatants are combined, diluted 2× with water and extracted 8× with chloroform. By colorimetric analysis, PEG is absent. The slightly emulsified aqueous layer is centrifuged (1700×g, 20 min) and the clear aqueous layer is removed. The final aqueous solution is placed in an Amicon stirred cell concentrator (10K NMWCO regenerated cellulose), and subjected to concentration/dilution cycles until the effluent conductance is near zero. The solution is then concentrated as much as possible, filtered through a Millipore Steriflip filter (0.2µ), and the Compound 2 concentration estimated to be 2.6 mg/mL (size exclusion chromatography, WV absorption at 206 nm).

Verification of Compound 2 Structure

Compound 2 was analyzed by size exclusion chromatography (SEC) on a Superose 6 analytical chromatography column (3.2 mm×30 cm): 25 µL injection; 20 mM sodium phosphate mobile phase, pH 7, flowing at 50 µL/min. over 60 min. (isocratic); and WV detection at 206 nm. Dextran standards from 25-270 kD were used for calibration.

The chromatogram obtained shows a normal, symmetrical, bell-shaped curve centered at approximately 30 min. (80-150 kD) and bounded at about 20 min. (>270 kD) and about 40 min. (<23.8 kD).

Compound 4 mass spectral analysis:
ES/MS m/z=1264.1 (M−H), 642.8 [(M−2+Na)/2], 631.5 [(M−2)/2]1265.7 (M+H), 807.4 (glycosyl cation), 644.4 [(M+H+Na)/2], 655.4 [(M+2Na)/2], 633.5 [(M+2)/2]

EXAMPLE 2

Stimulation of IL10 Expression in Human Peripheral Blood Mononuclear Cells by a Compound of Formula VI Since natural peptidoglycans and bacterial capsular antigens have been shown to stimulate inflammatory cytokines in vitro and in vivo, we sought to determine the cytokine profile elicited from human peripheral blood mononuclear cells (PBMCs) exposed to a compound of Formula VI, exemplified by Compound 1.

Figure 3:
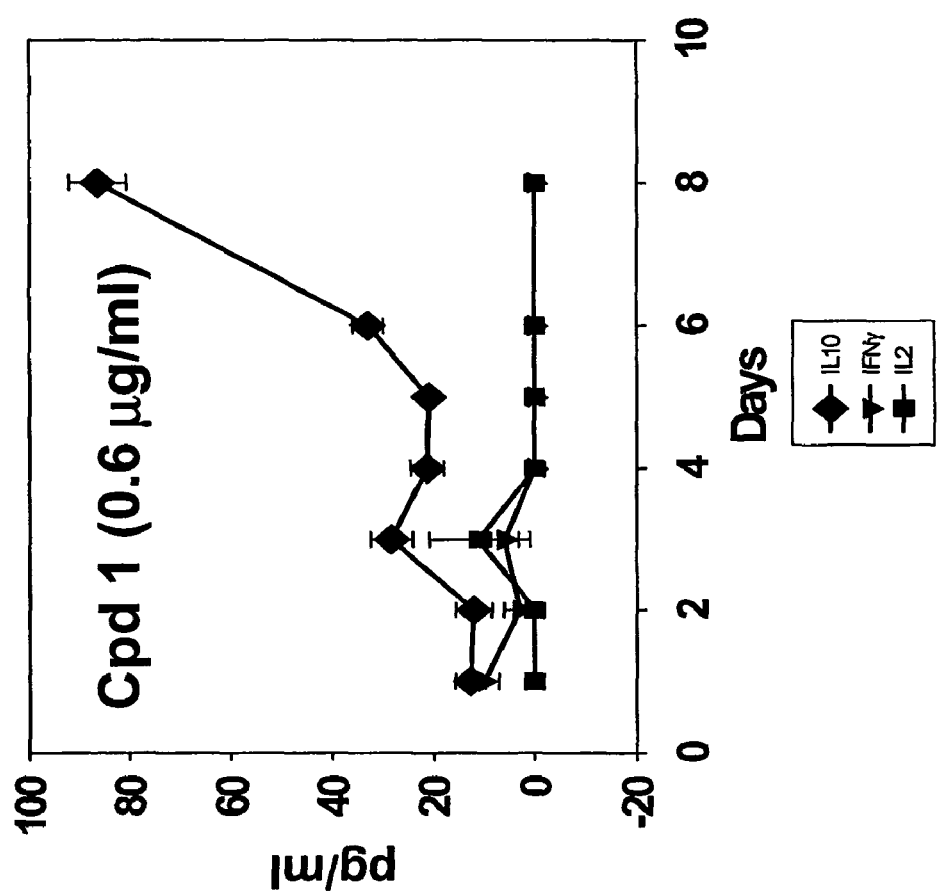
FIG. 3 shows the cytokine profile from human peripheral blood mononuclear cells (PBMCs) treated with Compound 1. Human PBMCs in culture are treated with Compound 1 at 0.6 micrograms/ml, and the expression of cytokines is measured over the course of eight days. Results are normalized against untreated media controls. Data are expressed as the average of triplicate wells 3± the standard error of the concentration of cytokines represented. The results show that the primary response to treatment with Compound 1 is the expression of IL10.

Human PBMCs are obtained from anonymous donors through the Eli Lilly and Company donor program. Mononuclear cells are separated by Ficoll-hypaque (Stem Cell Technologies, Vancouver, Canada) sedimentation to eliminate red blood cells and polymorphonuclear leukocytes. The mononuclear layer, consisting of T, B, and mononuclear cells, is cultured in RPMI 1640 with 10% fetal bovine serum (Gibco, BRL, Carlsbad Calif.). PBMCs (2×10$^6$ cells/well) are cultured with several concentrations of Compound 1 to determine the optimal response. Although the response to Compound 1 typically varies among human donors, a concentration of 0.6 µg/ml of Compound 1 gives reproducible and consistent results and is therefore used in these experiments (FIG. 3). Following isolation, human PBMCs are treated with Compound 1 (0.6 µg/ml) and maintained in culture for eight days. Supernatants are sampled daily and analyzed for cytokine expression using a multiplex Enzyme Linked Immunosorbent Assay (Luminex, Linco Research, St. Charles, Mo.; catalog no. HCYTO-60K). The human multiplex cytokine kits employed in these experiments measure IL1, IL2, IL4, IL6, IL8, IL10, TNFα, and INFγ. In additional experiments, a custom IL12 specific antibody bead complex is added to further define the cytokine response (Luminex, Linco Research, St. Charles, Mo.). In all assays, results are normalized against untreated media controls. Data are expressed as the average of triplicate wells ± the standard error of the concentration of cytokines represented. The data represent typical results from at least three experiments.

As shown in FIG. 3, data from several experiments reveal that treatment of human PBMCs with Compound 1 results in only minimal expression of most inflammatory cytokines represented in the kit. Surprisingly, the predominant response is the expression of the anti-inflammatory cytokine IL10. The expression of IL10 occurs late in the time course, detectable at day 5 and continuing to rise at day 8 to a concentration of approximately 80 pg/ml. IL2 and INFγ are only barely detectable early in the time course, whereas the expression of IL4, IL6, IL12 or TNF are not detected at any time point.

These results suggest that compounds of Formula VI, as exemplified by Compound 1, will selectively induce the expression of IL10 in PBMC cell cultures, and that they will be efficacious in animal models of inflammation and in treating various types of inflammatory pathologies.

EXAMPLE 3

Interaction of Compounds of Formula VI With Toll-Like Receptor 2 (TLR2)

Toll-like receptors (TLRs) play a critical role in early innate immunity to invading pathogens by sensing the presence microorganisms within the body (Akira et al. (2001) *Nature Immunol.* 2:675-680.) These receptors recognize highly conserved structural motifs only expressed by microbial pathogens, called pathogen-associated microbial patterns (PAMPs) (Medzhitov (2001) *Nat. Rev. Immunol.* 135-145). PAMPs include various bacterial cell wall components such as lipopolysaccharides (LPS), peptidoglycan and lipopeptides, as well as flagellin, bacterial DNA, and viral double-stranded RNA. Stimulation of TLRs by PAMPs initiates a signaling cascade leading to the activation of the transcription factor NF-κB, which induces the secretion of pro-inflammatory cytokines and effector cytokines that direct the adaptive immune response (Janeway et al. (2002) *Annu. Rev. Immunol.* 20:197-216). Since natural peptidoglycan is a PAMP that activates cells via TLR-2 (Iwaki et al. (2002) *J. Biol. Chem.* 277:24315-24320), we sought to determine if compounds of Formula VI, exemplified by Compound 1, could also activate NF-κB in vitro.

These experiments involve transfecting HEK293 cells (American Type Culture Collection, Manassas, Va.) with two plasmid DNAs. The first plasmid, pcDNA3.1/Hygro (Invitrogen), contains the human TLR-2 gene. The second plasmid, pNF-κB-luc (Stratagene, La Jolla, Calif.), encodes the NF-κB gene linked to a luciferase reporter gene whose product can be followed in vitro as a direct measure of NF-κB-activation. To prepare the DNA for transfection into the cells, Fugene6 (Roche, Basel Switzerland) transfecting reagent is diluted 1:6 in OPTI-MEM (Invitrogen, Carlsbad, Calif.) growth medium. Next, 75 ng of pNF-κB-luc and 300 ng of pcDNA3.1/Hygro DNA are added to the diluted Fugene6 and the mixture is incubated at 37° C. for 30 minutes. HEK293 cells at a concentration of $10^6$ cells/ml are added to the DNA/Fugene6 mixture. After gentle mixing, the cell/DNA mixtures are aliquoted into 96 well tissue culture plates at a concentration of $10^5$ cells/well and incubated for 24 h at 37° C. in a 5% $CO_2$ environment. After incubation, varying concentrations of test compounds are added to the cells and incubation is allowed to continue for an additional 24 h. The amount of luciferase activity resulting from incubation with the compounds is evaluated by removing the growth medium from the cells and replacing it with 100 µl of RLB lysis solution (Promega, Madison, Wis.). Lysis is completed by a single freeze/thaw cycle at −80° C. The luciferase activity of each cell culture is determined in a 25 µl aliquot of cell lysate in a Victor Luminometer (Perkin Elmer Life Sciences, Shelton, Conn.) according to the manufacturer's instructions. A positive control for NFκB activation in HEK293 cells is incubation of transfected cells with TNFα (Pharmingen, Palo Alto, Calif.) at a concentration of 1 ng/ml.

Table 1 shows that, using varying concentrations of commercially-available natural peptidoglycan isolated from *Staphylococcus aureus* (Fluka, St. Louis, Mo.), up to 54.5-fold induction of NFκB activity is observed compared with that of unstimulated cultures. Another commercially available preparation of peptidoglycan and polysaccharide mixture (PG/PS; Lee Labs Inc., Grayson, Ga.) stimulates up to a 33.7-fold induction of NF-κB in HEK293 cells. The data in Table 1 show the lack of NF-κB activation by Compound 1 at concentrations up to 500 µg/ml.

TABLE 1

Luciferase Assay for Measurement of TLR2 Activity in HEK293 Cells

| Concentration (µg/ml) | *Staphylococcus aureus* peptidoglycan (Fluka) | PG/PS (Lee Labs Inc) | Compound 1 |
|---|---|---|---|
| 500 | 48.0 | 33.7 | 0 |
| 250 | 51.8 | 27.0 | 0 |
| 125 | 54.5 | 15.2 | 0 |
| 62.5 | 50.7 | 8.8 | 0 |
| 31.2 | 48.6 | 5.3 | 0 |
| 15 | 37.7 | 3.0 | 0 |
| 7.5 | 34.9 | 2.6 | 0 |
| 3.7 | 31.8 | 1.9 | 0 |
| 1.8 | 24.7 | 1.6 | 0 |
| 0.93 | 20.7 | 1.5 | 0 |
| 0.46 | 17.8 | 1.0 | 0 |

Positive stimulation control: cultures incubated with 1 ng/ml TNFα yielded a 22.5-fold increase in luciferase activity compared with unstimulated cultures.

These results demonstrate that unlike natural peptidoglycan (which is a PAMP), Compound 1, which is representative of compounds of Formula VI, does not induce activation of NFκB through TLR2.

EXAMPLE 4

Interaction of a Compound of Formula VI with Other Toll-Like Receptors (TLRs)

Concurrently with the studies investigating the interaction of Compound 1 with TLR2, we also tested the interaction of Compound 1 with an expanded list of TLR constructs using the same NF-κB-reporter assays described above in Example 3 (Table 1). The results are shown in Table 2.

TABLE 2

Summary of TLR activation[1] via NFκB Using Various Compounds

| Receptor | Escherichia coli LPS | Compound 1 | PG/PS (Lee Labs) |
|---|---|---|---|
| TLR2 | + | − | ++ |
| TLR2/CD14 | ++ | − | ++ |
| TLR4/CD14 | +++ | − | − |
| TLR5 | + | − | − |
| TLR7 | +/− | − | − |
| TLR8 | − | − | − |

[1] The relative positive activation of NFκB is indicated by the number of "+" signs while a lack of activation is indicated by a "−" sign.

As shown in Table 2, concentrations of Compound 1 between 0.001-100 μg/ml elicit no NF-κB-signaling with any of the other TLR receptors. In all of these experiments, LPS serves as a positive control for TLR4 activation and natural PG serves as a positive control for TLR2 activation.

These experiments confirm the previous observation (Example 3) that Compound 1 does not activate TLR2, even in the presence of a necessary adaptor molecule CD14 (Janeway et al. (2002) *Annu. Rev. Immunol.* 20:197-216), and extends this observation to five other TLRs.

EXAMPLE 5

A Compound of Formula VI Does Not Stimulate Maturation of Human Dendritic Cells (DCs)

DCs are often referred to as professional antigen presenting cells and sentinels of the immune system (Banchereau et al. (2000) *Annu. Rev. Immunol.* 18:767-811). They reside in almost all peripheral tissues in an immature state (iDC), which allows them to phagocytose (or engulf) antigens so they can be processed and presented to the immune system, specifically to naïve T cells (Shortman et al. (2002) *Nat. Rev. Immunol.* 2:151-161). With their cargo of processed antigens, the dendritic cells migrate via the blood and lymphatic circulation to lymph nodes, spleen, and other lymphoid tissues. During this journey, they mature, losing their ability to take up and process antigen, and begin to display that antigen on their surfaces. By the time they reach their destinations, they have become potent stimulators of T cells and, with their multitentacled (dendritic) shape, proceed to make cell-cell contact with large numbers of T cells (Banchereau et al. (2000) *Annu. Rev. Immunol.* 18:767-811).

Certain CD (cluster of differentiation) markers, which are surface-exposed proteins and glycoproteins, can be used to track the maturation state of the dendritic cells (Chakraborty et al. (2000) *Clin. Immunol.* 94:88-98). Table 3 lists the commonly used CD markers for this purpose and their relative expression levels on monocytes, immature dendritic cells (iDC), and mature dendritic cells (mDC) (Chakraborty et al. (2000) *Clin. Immunol.* 94:88-98).

TABLE 3

Cluster of Differentiation (CD) Markers used to distinguish monocytes (MO), immature-(iDC) and mature-(mDC) dendritic cells.

| | Cell Surface Marker[1]: | | | | |
|---|---|---|---|---|---|
| | CD1a | CD14 | CD83 | CD86 | HLA-DR |
| MO | − | ++ | − | − | − |
| iDC | ++ | − | − | − | − |
| mDC | ++ | − | +++ | +++ | +++ |

[1] The relative amount of each cell surface marker is indicated in the table by the number of "+" signs while the absence of the cell surface marker is indicated by a "−" sign Labeling cells with fluorescently-conjugated anti-CD antibodies permits analysis of dendritic cell maturation status via determination of mean fluorescence intensity (MFI) of the marker on the surface of a cell population. Flow cytometry is used to analyze large cell samples for the presence of cell surface markers. In vitro, iDC can be produced by isolating CD14(+) monocytes from human blood and culturing these cells for four days with a cocktail of two cytokines (Granulocyte-Macrophage Colony-Stimulating Factor (GM-CSF) and Interleukin-4 (IL-4)). Since several bacterial molecules, for example LPS (Matsunaga et al. (2002) *Scand. J. Immunol.* 56:593-601) and peptidoglycan (Michelsen et al. (2001) *J. Biol. Chem.* 276:25680-25686), can induce the differentiation of iDCs to the mDC phenotype (as would occur during activation of the innate immune system), we were interested in evaluating the potency of a compound of Formula VI in maturing human monocyte-derived dendritic cells.

Human PBMCs are obtained from anonymous donors through the Eli Lilly and Company donor program. Mononuclear cells are separated by Ficoll-hypaque (Stem Cell Technologies, Vancouver, Canada) sedimentation to eliminate red blood cells and polymorphonuclear leukocytes. The CD14(+) monocyte fraction is isolated from PBMCs by incubation with CD14-conjugated magnetic beads (Miltenyi Biotech Inc., Auburn, Calif.) followed by physical separation in a magnetic field using an autoMACS apparatus (Miltenyi Biotech, Inc., Auburn, Calif.). Once isolated, the CD14(+) monocytes are incubated in complete DC media consisting of RPMI 1640 containing 10% heat-inactivated Australian fetal bovine serum (FBS), non essential amino acids, sodium pyruvate, 2-mercaptoethanol, penicillin-streptomycin (as 1× solutions all from Gibco BRL, Carlsbad Calif.). In addition, some cultures are induced to differentiate into iDCs using complete DC medium containing 20 ng/ml IL-4 (Sigma, St. Louis, Mo.) and 40 ng/ml GM-CSF (Pharmingen, Palo Alto, Calif.) for four days at 37° C. with 5% $CO_2$. After the four day incubation, cells are incubated with Compound 1 or LPS for an additional 24 h before being stained for CD marker analysis by flow cytometry. The standard staining protocol for flow cytometry involves washing the cells twice in Dulbecco's phosphate buffered saline (DPBS, Gibco BRL, Carlsbad, Calif.) containing 2% heat inactivated FBS (Gibco BLR, Carlsbad, Calif.) and 0.05% sodium azide (Sigma, St. Louis, Mo.), hereafter referred to as "flow wash solution." After washing, $10^5$ cells/sample are resuspended in 100 μl of flow wash solution and 20 μl of pre-diluted phycoerythrin-conjugated primary anti-CD marker antibody (all antibodies used are from Pharmingen, Palo Alto, Calif.) for 15 min on ice. A similarly conjugated isotype control antibody is included in all analyses. After incubation, cells are washed three times in flow wash solution. After the final wash, cells are fixed by resuspension in the flow wash solution containing 1% paraformaldehyde (Becton Dickinson, Palo Alto, Calif.). Cell samples are stored at 4° C. and protected from light until analysis using an FC500 flow cytometer (Beckman Coulter, Miami, Fla.). Once cells are correctly gated for forward and side scatter profiles, mean fluorescent intensity (the amount of marker on the cell surface) is evaluated for 10,000 cells/sample.

The results of these experiments are summarized in Table 4.

TABLE 4

Flow cytometric analysis of monocyte-derived dendritic cells after incubation with Compound 1 or LPS

| Cell type | Cell Surface Marker[1]: | | | | |
|---|---|---|---|---|---|
| | CD1a | CD14 | CD83 | CD86 | HLA-DR |
| MO | 5.1 | 16.5 | 5.6 | 12.8 | 23.9 |
| iDC | 116.1 | 3.3 | 7.6 | 10.9 | 7.7 |
| iDC + Cpd 1 | 109.8 | 3.4 | 9.5 | 12.1 | 9.1 |
| iDC + LPS | 124.4 | 4.1 | 46.7 | 75.4 | 29.2 |

[1]Numbers represent mean fluorescence intensity of cell surface markers in 10,000 cells/sample.

As shown in Table 4, the panel of surface markers used in this experiment confirms that the four day incubation of CD14(+) monocytes with GM-CSF and IL-4 induces the differentiation of the cells into immature dendritic cells (compare the results in Table 4 with the expected phenotype summarized in Table 3). As shown in Table 4, these immature dendritic cells are functionally capable of reaching a mature state since incubation of these cells with *E. coli* LPS (the positive control for maturation) significantly increases the staining of CD-83, -86 and HLA-DR on their cell surfaces, which is the expected phenotype of a mature DC. The data in Table 4 show that incubation with Compound 1 fails to change the staining profile from the iDC state, indicating that this compound, representative of compounds of Formula VI, is capable of affecting the maturation of dendritic cells.

EXAMPLE 6

Uptake of a Compound of Formula VI by Immature Human Dendritic Cells (iDCs)

The inhibition of maturation of DCs induced by Compound 1 may be due to the inability of these cells to process these molecules internally. Antigen uptake and processing (degradation) are two fundamental properties of APCs (Banchereau et al. (2000) *Annu. Rev. Immunol* 18:767-811). DCs are the most potent APCs of the immune system in part because of their powerful capacity to endocytose or sample material from their environment (Shortman et al. (2002) *Nat. Rev. Immunol.* 2:151-161). To determine whether iDCs are capable of endocytosing high molecular weight immunomodulatory polysaccharide antigens such as compounds of Formula VI as exemplified by Compound 1, we prepared a fluorescent derivative of Compound 1 for use in uptake studies employing confocal microscopy. This imaging technique can be used to localize within cells fluorescent probes such as the Oregon-green labeled Compound 1 disclosed herein. In these experiments, fluorescently labeled (FITC) dextran polymer is used as a control molecule. Dextran (40 kDa in size) is a macromolecule commonly used for endocytosis experiments (Sallusto et al. (1995) *J. Exp. Med.* 182:389-400). Since it is a high molecular weight carbohydrate polymer, it is a useful comparator for Compound 1.

Oregon-green labeled Compound 1 is prepared as described in PCT International Publication WO 01/79242. Briefly, Oregon-green (Molecular Probes, Eugene, Oreg.)-conjugated Lipid II is included in an MtgA polymerization reaction at a ratio of 1:4 with unlabeled Lipid II to produce a 25% Oregon-green labeled polymer. The polymeric material is purified and treated as previously described. For uptake studies, fluorescent Compound 1 at a final concentration of 50 μg/ml, or Lysine-fixable FITC-conjugated dextran (40 kDa size, Molecular Probes, Eugene, Oreg.) at 1 mg/ml, is incubated with human monocyte-derived iDC prepared as described in Example 5 for two minutes at 37° C. After incubation, extracellular probe is removed by washing the cells four times in ice cold complete DC medium (Example 5). Washed cells are then incubated at 37° C. and staining is stopped at two-minute intervals by washing in 1% paraformaldehyde fix diluted in flow wash solution (which also contains the metabolic poison sodium azide; protocol described in Example 5). Glass slide samples are prepared at each time interval and sealed with clear nail polish. Samples are stored at −20° C. and protected from light until analysis on a Radiance 2100 confocal microscope (BioRad Laboratories, Hercules, Calif.).

Figure 4:
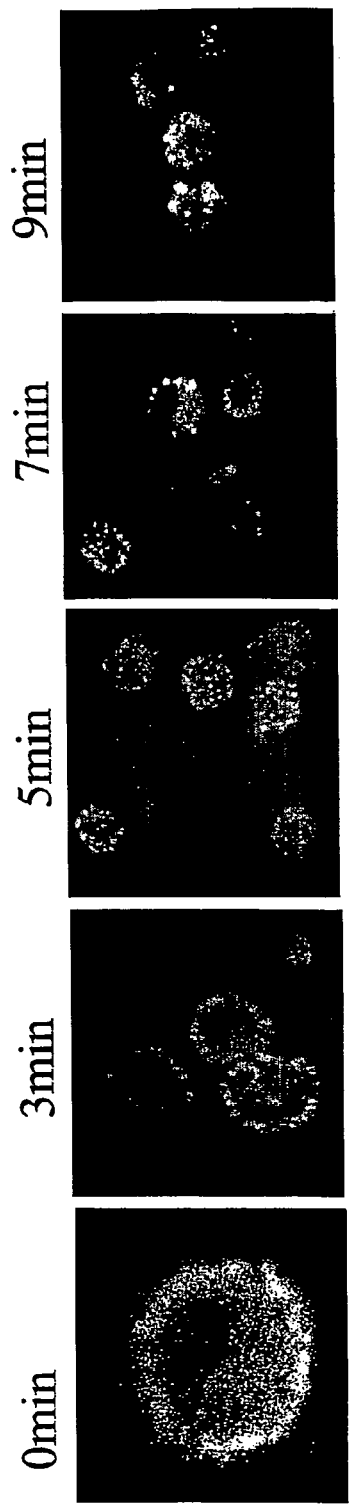
FIG. 4 shows Confocal microscope images of human iDCs treated with either FITC-Dextran (FITC-Dx, 40 kDa in size; Panel A) or Oregon-green labeled Compound 1 (OG-Cpd 1, approx. 150 kDa in size; Panel B) for two minutes. After incubation with the polymers, the cells are washed extensively to remove any external polymer and the internalized material followed at two-minute intervals. Localization of polymer in endocytic vacuoles can be seen using either compound, and fluorescence is visualized in the photographs as white punctate material within the dark field of the cells.
Figure 4:
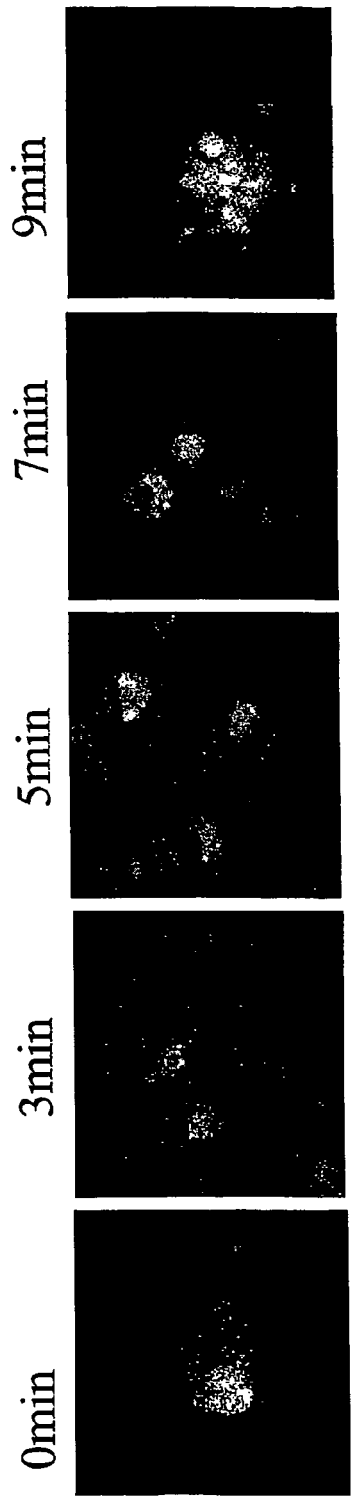

FIG. 4 shows black and white confocal images of human iDCs treated with either FITC-Dextran (40 kDa in size) (Panel A) or Oregon-green labeled Compound 1 (approx. 150 kDa in size) (Panel B) for two minutes. After incubation with the polymers, the cells are washed extensively to remove any external polymer and the internalized material is followed at two-minute intervals.

Intracellular localization of either FITC-Dextran or Compound 1 is visible as bright areas in the dark field of the cells after a two-minute incubation with the polymers (FIG. 4, Panels A and B, respectively). Furthermore, the internalized polymers are not spread throughout the cytoplasm, but are instead localized in discrete packets or vesicles, consistent with their presence in endocytic vacuoles.

These results demonstrate that iDCs are capable of endocytosing a compound of Formula VI, i.e., Compound 1.

EXAMPLE 7

Kinetics of Uptake of a Compound of Formula VI by Immature Human Dendritic Cells (iDCs)

Since there appears to be such robust uptake of Compound 1 by iDCs (FIG. 4), the fluorescent version of this molecule is used in flow cytometry to visualize the kinetics of polymer uptake.

In these experiments, human monocyte-derived dendritic cells are prepared as described in Example 5. Dendritic cells are resuspended at $5\times10^5$ cells/sample and incubated on ice at 37° C. At the start of each time course, cells are incubated with either fluorescent Compound 1 at a final concentration of 50 μg/ml or Lysine-fixable FITC-conjugated dextran (40 kDa size, Molecular Probes, Eugene, Oreg.) at 1 mg/ml. At 0, 2, 10, 20, 30, 40, and 50 minutes after the start of incubation, uptake is stopped by washing the cells with four washes of ice cold flow wash buffer (Example 5). The washed cells are fixed in paraformaldehyde also as described in Example 5. Stained, fixed cells are stored at 4° C. protected from light until analysis using a FC500 flow cytometer (Beckman Coulter, Miami, Fla.). Once cells are correctly gated for forward and side scatter profiles, mean fluorescent intensity of the population is evaluated for 10,000 cells/sample.

Figure 5:
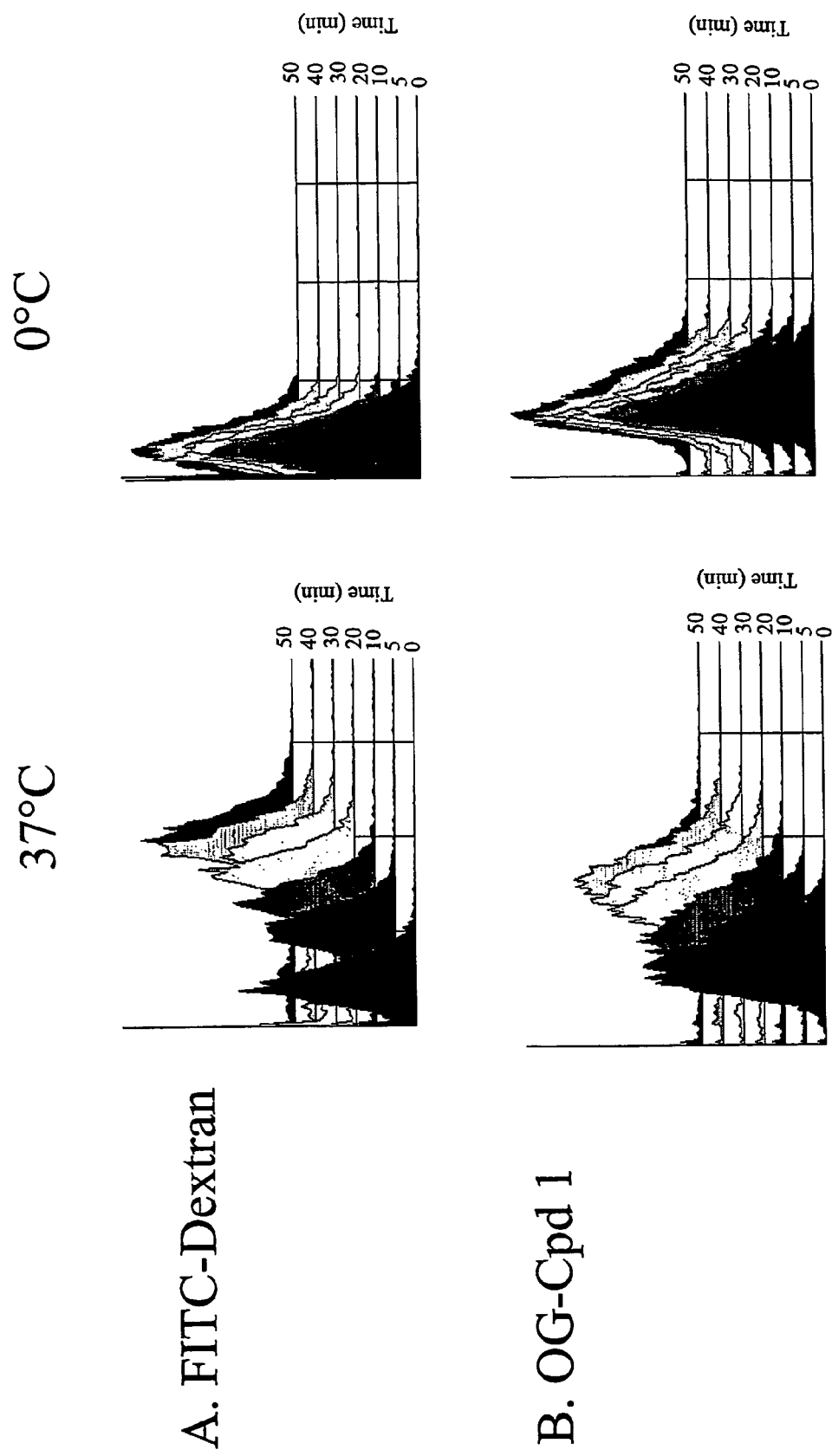
FIG. 5 shows flow cytometric analysis of uptake of either FITC-Dextran (panel A) or Oregon-green labeled Compound 1 (panel B) by human monocyte-derived dendritic cells at 37° C. or 0° C., respectively. Each histogram shows the mean fluorescence intensity of fluorescent signal versus cell number at the time intervals indicated. The results show that the uptake of each molecule is similar, and that this uptake is inhibited when the cells are metabolically inactive at 0° C.

FIG. 5 (Panel B) shows that over time, Oregon-green labeled Compound 1 accumulates in the iDC cytoplasm. The same is true for the control molecule FITC-Dextran (FIG. 5, Panel A). To control for non-specific adhesion of the molecules to the cell surface (which could be read as a positive in this assay), cells are also incubated with the fluorescent polymers at 0° C. At this temperature, the iDCs are viable yet unable to endocytose material, i.e., they are metabolically inactive (Sallusto et al. (1995) *J. Exp. Med.* 182:389-400). At this temperature, signal from neither the control molecule (FITC-dextran) nor Compound 1 increases over time (FIG. 5, Panels A and B, respectively). This indicates that the uptake seen at 37° C. is a result, of cellular endocytosis.

These results demonstrate that iDCs are capable of rapidly endocytosing a fluorescently labeled compound of Formula VI, as exemplified by Compound 1, and that the inability of this molecule to mature DCs is not due to recalcitrance to endocytic uptake thereof.

EXAMPLE 8

Interference of a Compound of Formula VI With LPS-Induced Maturation of iDCs

As shown above in Table 4 (Example 5), LPS at 50 μg/ml is capable of transforming iDCs to an mDC phenotype characterized by an increase in co-stimulatory markers (CD83 and CD86) as well as class II Major Histocompatibility (MHC) markers (HLA-DR) (Chakraborty et al. (2000) Clin. Immunol. 94:88-98). We next investigated whether a compound of Formula VI, exemplified by Compound 1, is capable of interfering with the transformation of iDCs to mDCs. The results are shown in Table 5.

TABLE 5

Flow cytometric analysis of monocyte-derived dendritic cells matured with E. coli LPS in the presence of a Compound of Formula VI

| Cell type | Cell Surface Marker[1]: | | | | |
|---|---|---|---|---|---|
| | CD1a | CD14 | CD83 | CD86 | HLA-DR |
| iDC + LPS | 126.4 | 4.1 | 46.7 | 75.4 | 29.2 |
| iDC + LPS + Cpd 1 | 120.2 | 4.1 | 52.6 | 59.2 | 31.9 |

[1]Numbers represent mean fluorescence intensity of 10,000 cells/sample.

In these experiments, CD14(+) monocytes are isolated from human PBMCs and differentiated into iDCs as described in Example 5. After differentiation, iDCs are incubated with either of two known inducers of cell maturation: E. coli LPS (Matsunaga et al. (2002) Scand. J. Immunol. 56:593-601) or a cytokine cocktail containing Tumor Necrosis Factor-α (TNF-α), Interleukin-1β (IL-1β), Prostaglandin E$_2$, and IL-6 (Dieckman et al. (2002) J. Exp. Med. 196:247-253) for 24 h. To some induced cultures we also add 100 μg/ml Compound 1 at the same time we add either LPS or cytokines. After incubation, the cells are evaluated for CD1a, CD14, CD83, CD86, and HLA-DR expression by flow cytometry as described in Example 5.

In the case of cytokine-matured iDCs, flow cytometry confirms that maturation by incubation with the cytokine cocktail occurs; however, incubation with Compound 1 has no influence on the matured phenotype as determined by surface marker analysis (data not shown). In contrast to this, Table 5 shows that Compound 1 is able to interfere with LPS-induced maturation of iDCs. Specifically, surface expression of the co-stimulatory marker CD86 is decreased in the presence of this molecule, while the other markers tested are essentially unchanged. Additional experiments also demonstrate that CD80, another marker of co-stimulation, is also decreased (data not shown).

The powerful capacity of DCs to activate T cells is linked to their constitutive expression of both MHC and costimulatory markers like the family B7 markers (i.e., CD80 and CD86) (Banchereau et al. (2000) Annu. Rev. Immunol. 18:767-811). If these molecules are decreased or absent from the DC cell surface, the DCs are unable to participate in stimulatory cognate interactions with T cells. Schwartz ((1990) Science 248: 1349-1356) was the first to observe that presentation of antigen on MHC molecules in the absence of costimulatory molecules induces T-cell anergy. Thus, DCs can provide both stimulatory (by virtue of being APCs) and downregulatory signals for immune reactions.

To understand fully the significance of the above findings, it is important to understand the role of DCs in immune tolerance. Tolerance is an essential property of the immune system whereby self- or auto-antigens do not trigger an immune response (Belz et al. (2002) Immunol. Cell Biol. 80:463-468). Others have shown that when DCs undergo an incomplete maturation (low levels of CD80 and or CD86), or have been treated with antibodies that block the B7 family of costimulatory markers (i.e., CD80 and CD86), these cells can induce antigen-specific unresponsiveness in vitro and T cell anergy in vivo (Lu et al. (1996) J. Immunol. 157:3577-3586; Gao et al. (1999) Immunology 98:159-170). Immature DCs are now understood to contribute to peripheral tolerance by inducing the differentiation of human T regulatory cells (Jonuleit et al. (2000) J. Exp. Med. 192:1213-1222), a group of T cells that display regulatory functions in vitro and in vivo. Activated T regulatory cells have also been shown to elicit the production of IL-10, an anti-inflammatory cytokine, through autocrine expression or induction in effector T cells (Dieckmann et al. (2002) J. Exp. Med. 196:247-253). Thus, the fact that Compound 1, which is representative of molecules of Formula VI, appears to influence the expression of costimulatory markers on the DC surface suggests a mechanism of action for molecules of this type in the induction of tolerogenic DCs. These anergic DCs could then induce T-cell anergy directly or through the activity of a T regulatory cell population.

EXAMPLE 9

Molecules of Formula VI are Not Polyclonal Mitogens and do Not Stimulate Proliferation of Lymphocytes in Human PBMC Cultures Mitogens are substances that nonspecifically induce DNA synthesis and cell division in lymphocytes. LPS is a B-cell specific mitogen (Moller et al. (1973) J. Infect. Dis. 128:52-56), while phytohaemagglutinin (PHA) specifically induces T cells to divide (Boldt et al. (1975) J. Immunol. 114:1532-1536). Peptidoglycan is another T cell mitogen (Levinson et al. (1983) Infect. Immun. 39:290-296). We were therefore interested in determining whether compounds of Formula VI, as exemplified by Compound 1, could stimulate human peripheral blood mononuclear lymphocytes (PBMCs) to divide in culture, particularly since Compound 1 is a completely synthetic peptidoglycan. Cell division is measured in these experiments by uptake of radiolabeled nucleotide base into the DNA of the proliferating cells. The radioactive counts per minute (cpm) of the culture, measured by scintillation counting, are a direct measure of cellular proliferation.

In this experiment, PBMCs are isolated from a healthy human volunteer as described in Example 2. Isolated PBMCs are aliquoted into round-bottomed 96-well tissue culture plates (Falcon Brand, Becton Dickinson, Palo Alto, Calif.) at density of $10^5$ cells/well. Some cells are also incubated with 100 μg/ml Compound 1 or 25 μg/ml PHA (Sigma, St. Louis, Mo.) as a positive control for T cell proliferation. Cells are incubated at 37° C. in a 5% CO$_2$ atmosphere for up to four days. At 30, 54, and 78 hours post inoculation, some cultures are pulsed with 1 μCi/well of [$^3$H]-thymidine (Specific Activity 6.7 Ci/mmol; ICN Inc, Costa Mesa, Calif.) and returned to 37° C. incubation for a further 18 hours before being harvested onto filter plates (Packard Instruments, Shelton, Conn.) using a Filtermate harvester (Packard Instruments, Shelton, Conn.). Filterplates are dried after harvesting, prior to the addition of 20 μl/well of Microscint-O scintillation cocktail (Packard Instruments, Shelton, Conn.). Scintillation counting is performed with a MicroBeta TriLux liquid scintillation counter (Perkin Elmer, Shelton, Conn.).

Figure 6:
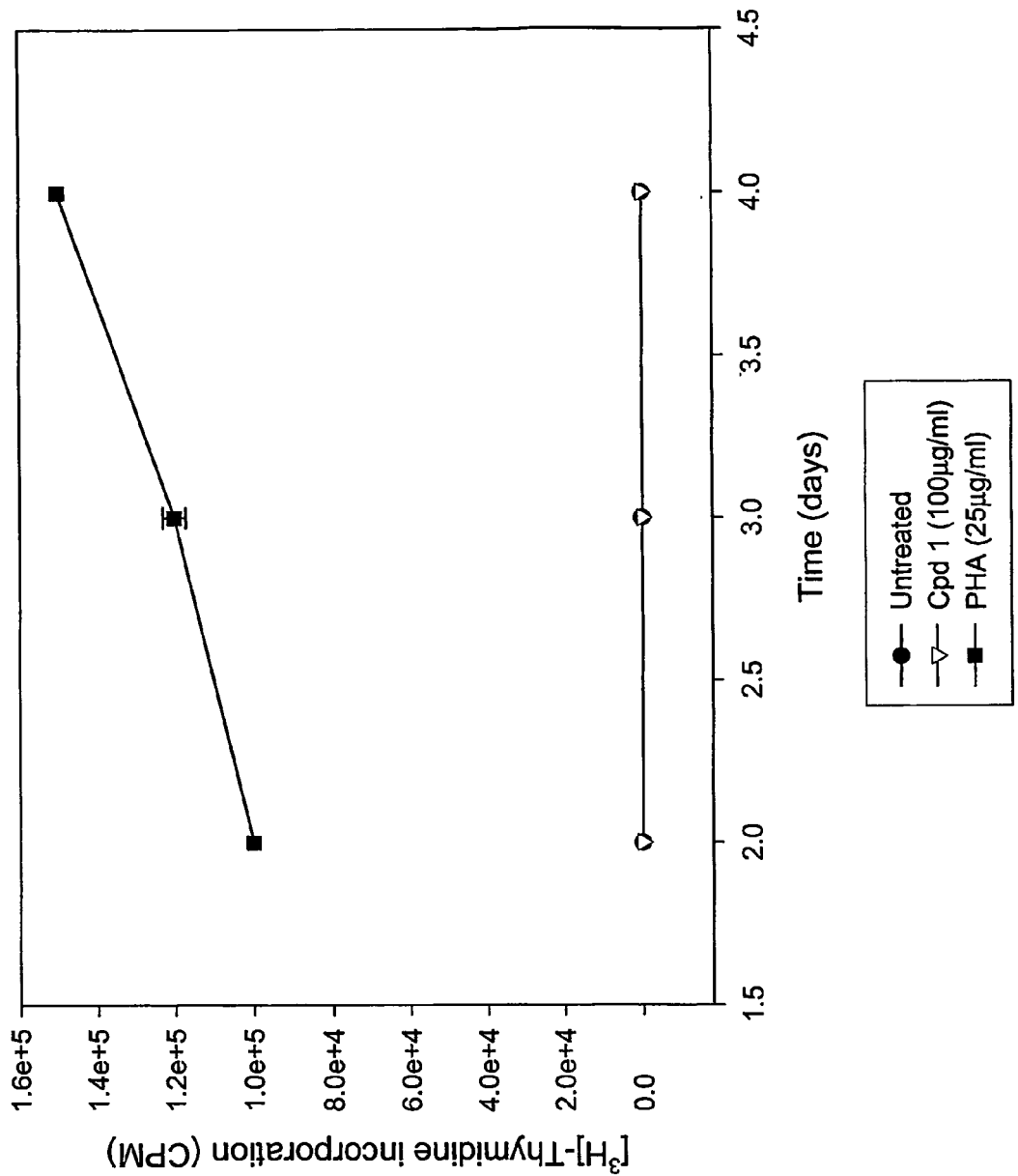
FIG. 6 shows that Compound 1 does not induce PBMCs to divide in culture. Isolated PBMCs are incubated with 100 μg/ml Compound 1 (▽), 25 μg/ml phytohaemagglutinin (PHA) (■), or left untreated (●) for the number of days indicated. Radioactive thymidine [$^3$H]-Thy is added to cultures 18 h prior to each time point and the amount of radiolabel incorporated by the cells is measured by scintillation counting. Radioactivity is measured as counts per minute.

FIG. 6 shows the typical proliferation response of human PBMCs to the polyclonal T cell activator PHA. The incorporation of [$^3$H]-thymidine into PHA-treated cells is close to 100,000 times that of untreated cells after two days exposure, and proliferation rates increase up to four days. In contrast, cells treated with Compound 1 do not respond by DNA proliferation and expansion (FIG. 6). Therefore, this compound, representative of molecules of Formula VI, does not appear to behave like a polyclonal mitogen in human PBMC cultures.

EXAMPLE 10

A Compound of Formula VI Suppresses the Anti-CD3 Antibody-Induced Proliferation of Lymphocytes in Human PBMCs When an antigen (Ag) is presented to a naïve T cell in the context of MHCII on the surface of an antigen presenting cell (APC), there is engagement of the MHC-Ag complex with the T cell receptor (TCR)/CD3 complex on the surface of the T cell (Weiss et al. (1986) *Annu. Rev. Immunol.* 4:593-619). This interaction, together with an amplification signal generated by CD28-B7 (CD80, CD86) interaction on these two cell types leads to T cell activation, cytokine stimulation, and cell division (Weiss et al. (1986) *Annu. Rev. Immunol.* 4:593-619). In the absence of Ag or APC, T lymphocytes can become activated and proliferate in vitro by incubation with plate-bound anti-CD antibodies (van Lier et al. (1989) *Immunol.* 68:45-50). Mimicking the activation by antigens, the binding of CD3 antibodies to T cells results in the activation of tyrosine kinase, a rise in the intracellular calcium concentration, generation of diacylglycerol, and activation of protein kinase C. Both calcium and protein kinase C serve as intracellular messengers for the induction of gene activation (van Lier et al. (1989) *Immunol* 68:45-50). Anti-CD3 antibody-mediated T cell proliferation can also measured by the incorporation of [$^3$H]-thymidine into the DNA of dividing cells as exemplified in FIG. 6.

Since proliferation of PBMCs is not observed following treatment with Compound 1 (FIG. 6), we hypothesized that molecules of this type may stimulate T regulatory cells. The present experiment is performed to investigate whether Compound 1 induces suppression of lymphocyte proliferation.

In this experiment, human PBMCs are isolated and cultured as described in Example 2 and plated at 10$^6$ cell/ml in T-25 tissue culture flasks (Corning Inc., Corning, N.Y.) for 24 h at 37° C. in a 5% CO$_2$ atmosphere. Cultures are exposed to Compound 1 at 100 μg/ml during this period. One day prior to the incubation of cells on antibody coated plates, anti-human CD3 antibody (Clone UCHT1, Pharmingen, Palo Alto, Calif.) or an isotype-matched control antibody (Pharmingen, Palo Alto, Calif.) is diluted in Dulbecco's phosphate buffered saline (DPBS) (Gibco, BRL, Carlsbad, Calif.), and the wells of a 96-well tissue culture plate are coated with 100 μl aliquots of diluted antibody. Plates are coated overnight at 4° C. and washed three times in DPBS before use. Human PBMCs exposed to Compound 1, or not exposed to this compound, are plated into antibody-coated wells at a density of 10$^5$ cells/well. Tissue culture plates are incubated at 37° C. in a 5% CO$_2$ atmosphere for 30 or 54 hours before 1 μCi/well of [$^3$H]-thymidine (Specific Activity 6.7 Ci/mmol; ICN Inc, Costa Mesa, Calif.) is added to each well. Cells are then returned to 37° C. incubation for an additional 18 h before the cells are harvested as described in Example 9. The liquid scintillation counting procedure is also as described Example 9. The data for this experiment are calculated as raw counts per minute (cpm) of radioactivity and as a stimulation index (SI) (not shown), which is the ratio of the cpm of cells in anti-CD3 antibody-coated wells to the cpm of cells in isotype (control) antibody-coated wells.

Figure 7:
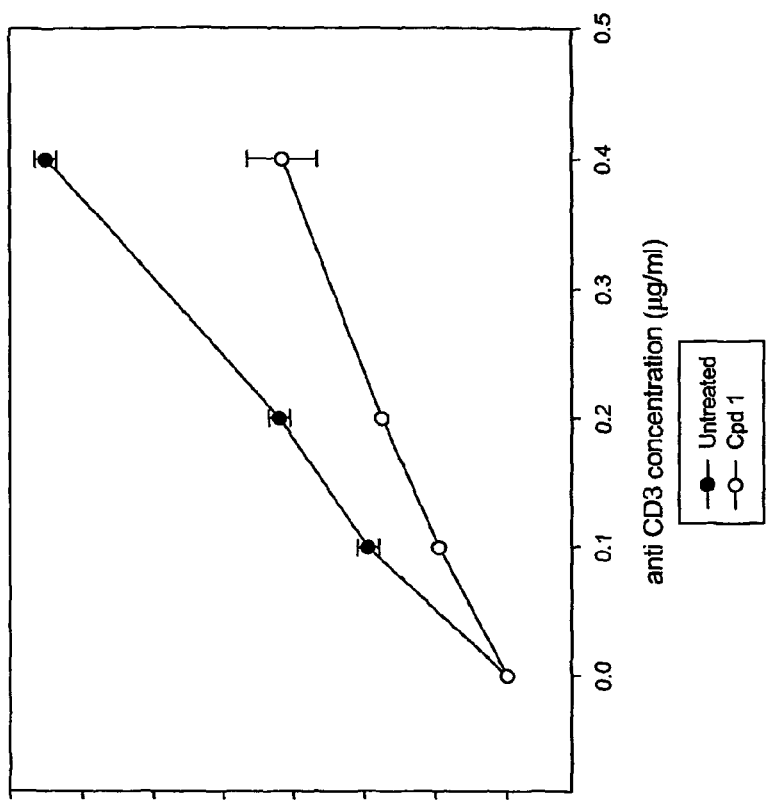
FIG. 7 shows that Compound 1 inhibits anti-CD3 antibody-mediated proliferation of human PBMCs. PBMCs are pre-incubated for 24 hours with 100 μg/ml of Compound 1 prior to incubation on tissue culture plates coated with varying concentrations of anti-CD3 antibody for 48 hours (Panel A) or 72 hours (Panel B). Cell proliferation is evaluated using a $^3$H-Thymidine incorporation assay followed by liquid scintillation counting.
Figure 7:
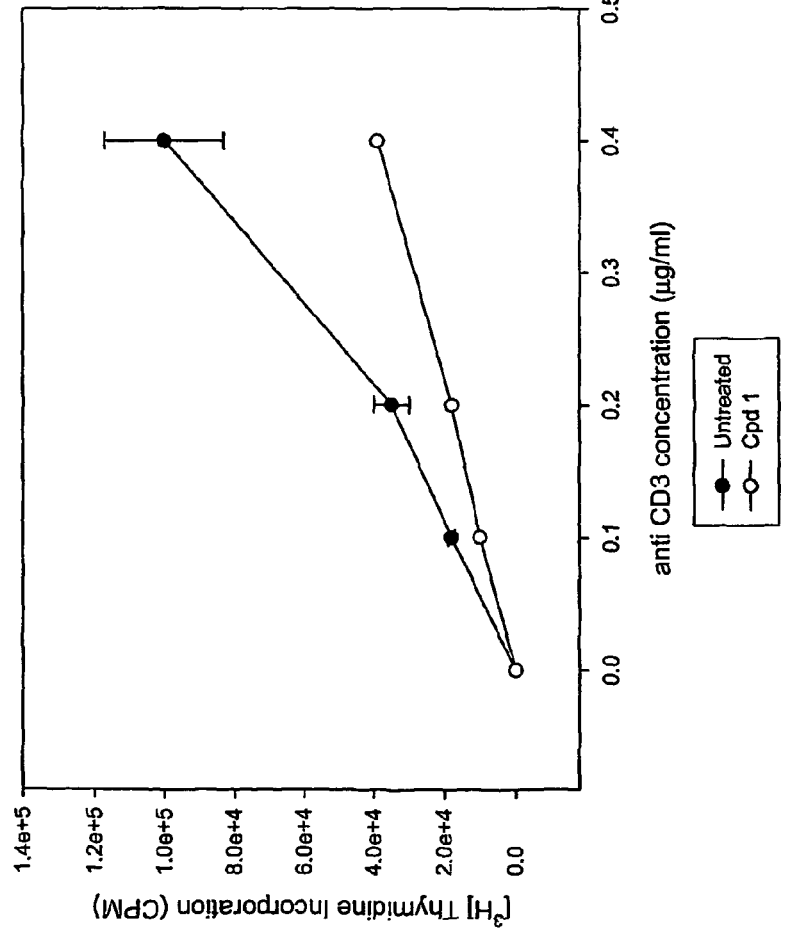

FIG. 7 shows that either 48 or 72 hour exposures to anti-CD3 antibody causes human PBMCs to proliferate as shown by the uptake of [$^3$H]-thymidine (FIG. 7, closed circles). Furthermore, the amount of proliferation is directly correlated to the amount of anti-CD3 antibody in the well, with the highest proliferation seen in cells exposed to 0.4 μg/ml anti-CD3 antibody. FIG. 7 also shows that pre-incubation of human PBMCs with 100 μg/ml Compound 1 for 24 h prior to incubation with anti-CD3 antibody causes a decrease in the amount subsequent proliferation (FIG. 7, open circles).

These results demonstrate that Compound 1, representative of compounds of Formula VI, inhibits anti-CD3 antibody-induced lymphocyte proliferation.

EXAMPLE 11

Micro-Array Analysis of Human CD3+ Cells Following Treatment with a Compound of Formula VI and Anti-CD3 Antibody The results demonstrating cytokine expression shown in FIG. 3 are corroborated and extended by measurement of cytokine modulation using microarray technology.

PBMCs are isolated as described in Example 2 and added to 6-well tissue culture plates in a medium containing RPMI with 10% fetal bovine serum (Gibco BRL, Carlsbad, Calif.), 50 μM β-mercaptoethanol, and 500 μg/ml penicillin/streptomycin (complete medium). T cell density is 2.5×10$^6$ cells per well. Either 100 μg/ml Compound 1 or complete medium is added to each well of the appropriate plate. Incubation is at 37° C. for 24 hours. Simultaneously, 6-well tissue culture plates are treated with either 0.2 μg/ml anti-CD3 antibody in sterile Phosphate-Buffered Saline (PBS, Gibco BRL, Carlsbad, Calif.), 5 ml/well, or an equal volume of sterile PBS. The uninoculated plates are incubated overnight at 4° C. Following incubation, cells treated with Compound 1, or untreated control cells, are gently resuspended and added to plates that have either been coated with anti-CD3 antibody or not, and incubation is continued at 37° C. for an additional 48 hours.

PBMCs are then processed with a Pan T Cell Isolation Kit (Miltenyi Biotec, cat. #130-053-001; Auburn, Calif.) in substantial accordance with the manufacturer's instructions. This kit is a magnetic labeling system designed to isolate non-activated T cells from peripheral blood. Non-T cells are removed by magnetic separation from unlabeled CD3$^+$ cells using an autoMACS (Miltenyi Biotec Inc, Auburn, Calif.). The isolated T cells are stored at −80° C.

Total RNA is isolated from the cells using Trizol (Gibco-BRL, Carlsbad, Calif.) followed by chloroform extraction and subsequent alcoholic precipitation following procedures specified by the manufacturer. The RNA is quantitated spectrophotometrically, and its integrity assessed by gel analysis. All RNA preparations are stored at −80° C. until needed.

Total RNA serves as the template for the synthesis of biotin-labeled cDNA. This labeled cDNA is subsequently used as a probe for commercially available directed microarrays. Specifically, a GEArray Q Series Human Common Cytokine Kit, cat. # HS-003N (SuperArray Bioscience Corporation, Frederick, Md.) is employed. Probe synthesis and microarray processing are performed as suggested by the manufacturer. A Typhoon 8600 Imager (Amersham Pharmacia Biotech, Piscataway, N.J.) is used in chemiluminescent mode to capture and store images that are then analyzed using ImageQuant software (Amersham Pharmacia Biotech, Piscataway, N.J.). Data are exported to Microsoft Excel, and image intensity is corrected for background and normalized between experiments using GEArray Analyzer software (SuperArray Bioscience Corporation, Frederick, Md.).

Analysis of the data reveals a cytokine modulation pattern that is consistent with that seen using the multiplex Enzyme Linked Immunosorbent Assay as shown in FIG. 3. Cells exposed to anti-CD3 antibody are activated and therefore show an up-regulation of IL17, TNF-β, and other cytokines known to participate in the inflammatory process. IL17 is thought to be expressed mainly by activated T cells, and functions to initiate and maintain an inflammatory response. Anti-CD3 antibody-treated cells also show decreases in both IL10 and IL19. When Compound 1 is added to cells that are subsequently exposed to anti-CD3 antibody, there is a dramatic increase in the level of IL10.

The up-regulation of IL10 expression in CD3+ T cells induced by Compound 1 in these microarray experiments corroborates the results observed in Example 2, and in animal models, and suggests that this cytokine can be used as a biological marker to monitor the biological/immunological activity of molecules of Formula VI as exemplified by Compound 1 in vitro and in vivo. The data also suggest that directed microarrays can be used to monitor not only the biological activity of the present compounds, but also the biological activity of derivative compounds to determine the effects of structural differences on immunodulatory potency.

EXAMPLE 12

Compounds of Formula VI Protect Against the Formation of Intra-Abdominal Abscesses Since Compound 1 induces T regulatory cells with suppressive function in vitro as well as the late production of IL10 from human PBMCs (Example 10 and Example 2, respectively), we were interested in assessing the ability of this synthetic polymer antigen to protect animals against the inflammatory formation of abscesses in vivo. A rat intra-abdominal abscess model is used to address this question.

The rat model of abscess formation employed in these studies is a modification of that described by Onderdonk et al. ((1977) *J. Infect. Dis.* 136:82-87) and Tzianabos et al. ((1993) *Science* 262:416-419). Male Lewis rats (Charles River Laboratories, Wilmington, Mass.), weighing between 135-175 grams, are used for all experiments. Rats are housed in microisolator cages and given chow (Ralston Purina, St. Louis, Mo.) and water ad libitum. Upon arrival, animals are allowed to acclimate for 24 hours. Intra-abdominal abscesses are induced by a single intraperitoneal injection of prepared inoculum containing *Bacteroides fragilis* (ATCC 23745; American Type Culture Collection, Manassas, Va.) ($10^8$ colony forming units per animal) mixed at a 1:6 dilution with an adjuvant solution containing sterile rat cecal contents. *B. fragilis* is maintained at −80° C. in brain heart infusion broth. Cultures are grown anaerobically in brain heart infusion broth to log phase and diluted for use with rat sterile cecal contents (rSCC). rSCC is prepared from rat cecal pellets that are solubilized in brain heart infusion broth, autoclaved, and then filtered. Animals are euthanized at six days post-inoculation and assessed for abscess formation. Animals with one or more fully formed abscesses are scored as positive. Animals with no abscesses yield a negative score. Individuals scoring the results are blinded to the identity of the experimental groups.

Animals (10 rats/group) are dosed subcutaneously with three doses of Compound 1 at twenty four hour intervals the day before, the day of, and the day after challenge with *B. fragilis*/rSCC (Tzianabos et al. *J. Clin. Invest.* 96:2727 (1995)). Challenge with the inoculum is carried out by the intraperitoneal route. Animals are administered log dilutions of Compound 1 at 100, 10, and 1 μg (×3)/animal. Results are expressed as the percent protection (number of animals with no abscesses/treatment group), and statistical significance is calculated using the Fishers Exact Probability Test.

As shown in Table 6, Compound 1 produces considerable protection against the formation of abscesses at both the 100 μg and 10 μg doses when compared to that of saline controls. Protection is assessed as the complete absence of abscesses as compared to control animals with one or more abscess. Protected animals show no deleterious effects of antigen administration, with few, if any, signs of fever or lethargy, which are common symptoms of inflammation. Nor do these animals display symptoms of sepsis.

TABLE 6

Activity of Compound 1 in the Rat Abscess Model

| Treatment Group | Animals with Abscesses/ group | % of Animals with Abscesses | % Protection |
| --- | --- | --- | --- |
| Cpd 1 100 μg × 3 SC | 1/8 | 12.5 | 87.5 |
| Cpd 1 10 μg × 3 SC | 1/8 | 12.5 | 87.5 |
| Cpd 1 1.0 μg × 3 SC | 2/8 | 25 | 75 |
| Saline 0.1 ml × 3 SC | 6/8 | 75 | 25 |

Taken together with the data shown in Examples 2-11, these data suggest that protection against the inflammatory processes required for the formation of abscesses in response to bacterial challenge in this model is inhibited by the presence of immature dendritic cells, which can directly inhibit T cell activation or induce the generation of a T regulatory population. Direct inhibition of inflammatory cells by T regulatory cell contact can further stimulate the expression of IL-10. In total, one or more of these events may orchestrate the inhibition of inflammation seen in the in vivo abscess model.

EXAMPLE 13

Compounds of Formula VI Reduce the Incidence and Severity of Post-Surgical Adhesions Exogenous IL10 has been shown to limit the formation of post-surgical adhesions (Holschneider et al. (1997) *J. Surg. Research* 70:138-143). Further, T regulatory cells have potent anti-inflammatory activity and have been shown to limit inflammation in in vivo models (Maloy et al. (2001) *Nat. Immunol.* 2:816-822; Shevach (2002) *Nat. Rev. Immunol.* 2389-400). T regulatory cells have also been shown to elicit the production of IL10 from their target inflammatory T cells (Diekman et al. (2002) *J. Exp. Med.* 196:247-253). As variously shown in Examples 2, 10, 11, and 12, above, Compound 1 stimulates the production of IL10 from PBMCs, an increase in T regulatory cell numbers and function in vitro, and affords protection from the formation of abscesses in vivo. Since the inflammatory responses that lead to fibrin deposition and the formation of abscesses is similar to the pathologies involved in adhesion formation, we hypothesized that treatment with Compound 1 in an adhesion model would likewise stimulate the activity of T regulatory cells and ultimately the endogenous production of IL10 that may result in reduction in the formation of post-surgical adhesions.

To test this hypothesis, male Lewis rats (Charles River Laboratories, Wilmington, Mass.) are dosed subcutaneously with three injections of Compound 1 at twenty four hour intervals the day before, the day of, and the day after surgical induction of adhesions (Tzianabos et al. (1995) *J. Clin. Invest.* 96:2727-2731). Rats are administered log dilutions of this compound at 100 µg, 10 µg, and 1 µg (×3) in 0.2 ml saline/animal. Control groups are administered saline in 0.2 ml volumes at the same dosing schedule. Peritoneal adhesions are induced following the methods of Kennedy et al. ((1996) *Surgery* 120:866-871) and Tzianabos et al. (PCT International Publication WO 00/59515) with minor modifications. Briefly, rats are anesthetized with 2-5% isoflurane in oxygen to a surgical plane of anesthesia. A one to two cm midline incision is made into the abdominal cavity to expose the cecum. The cecum is aseptically removed from the peritoneal cavity and abraded with surgical gauze to induce visible microhemorrhages. The cecum is then re-inserted into the peritoneal cavity. The left and right lateral abdominal walls are inverted aseptically and also abraded in the manner described above. Following this procedure, 0.2-0.3 ml of rat sterile cecal contents (rSCC), prepared as described in Example 12, are added to the peritoneal cavity as an inflammatory adjuvant (Onderdonk et al. (1982) *J. Clin. Invest.* 69:9-14). The peritoneum is closed with 3-0 silk followed by skin closure with tissue adhesive (3M Animal Care Products, St. Paul, Minn.). Animals are sacrificed one week following surgical manipulation and evaluated for the formation of adhesions. Adhesions are scored on a scale of 0-5 using the method described by Kennedy et al ((1996) *Surgery* 120:866-871): 0=no adhesions; 1=thin filmy adhesion; 2=more than one thin adhesion; 3=thick adhesion with focal point; 4=thick adhesion with planar attachment; and 5=very thick vascularized adhesions or more than one planar adhesion. This scoring system approximates the system used in human medicine, enumerates adhesions present, and indicates the severity of the adhesion pathology; higher scores indicate greater severity in inflammation and adhesion formation. The results are shown in Table 7.

TABLE 7

Activity of Compound 1 in the Rat Adhesion Model

| Treatment Group | Range of Adhesion Scores/Individual Scores | Mean Adhesion Score | Median |
|---|---|---|---|
| Cpd 1 100 µg × 3 SC | 0-4 (0, 0, 2, 2, 4) | 1.6 | 2 |
| Cpd 1 10 µg × 3 SC | 0-4 (0, 1, 3, 3, 4) | 2.2 | 3.0 |
| Cpd 1 1.0 µg × 3 SC | 0-4 (0, 1, 3, 3, 4) | 2.2 | 3 |
| Cpd 1 0.1 µg × 3 SC | 1-4 (1, 3, 3, 4, 4) | 3 | 3 |
| Saline 0.1 ml × 3 SC | 3-4 (3, 3, 4, 4, 4) | 3.6 | 4 |

The data shown in Table 7 demonstrate that adhesion formation in rats treated with 100 µg of Compound 1 is significantly limited (median score=2.0) when compared to that in saline controls (median score=4.0). These data demonstrate that this polysaccharide antigen effectively protects rats from the formation of severe surgically induced adhesions, and suggests that compounds of Formula VI induce an anti-inflammatory effect in vivo.

EXAMPLE 14

Effect of Compounds of Formula VI on Inhibition of Delayed Type Hypersensitivity Reactions in a Guinea Pig Model Clinical evaluation of the safety and efficacy of immune modulators such as compounds of Formula VI as exemplified by Compound 1 requires a convenient biomarker. This is necessary because safety and dose determination are usually determined in healthy volunteers, where a defined inflammatory process is not measured. Furthermore, such a biomarker would be useful in later stage trials as abscesses and/or adhesions cannot be readily observed and graded for therapeutic efficacy in a non-invasive manner following therapy with immune modulators. Consequently, we developed a delayed type hypersensitivity (DTH) animal model (Gray et al. (1994) *Curr. Opin. Immunol.* 6:425-437). This assay can also be used in humans as a biomarker for clinical efficacy studies using the present immune modulators. Clinically, DTH skin tests are of significant value in the overall assessment of immunocompetence in humans (Gray et al. (1994) *Curr. Opin. Immunol.* 6:425-437; Kuby et al. (2000) Immunology, W. H. Freeman and Co). Such tests including the administration of Candin as described below are commonly used to test immuno-competence in AIDS patients.

A Guinea pig model is used to demonstrate the utility of a DTH response as a biomarker. A localized DTH response in an animal model represents an important source of information with regard to T cell function. Direct measurements of the DTH response can be readily observed and measured in humans and animals. Flares, wheals, and/or indurations can be observed and readily measured quantitatively on the surface of the skin.

For this purpose, female Hartley Guinea pigs (Charles River Laboratories, Wilmington, Mass.) weighing 250-299 grams are used for all DTH experiments. Guinea pigs are housed in microisolator cages and given chow (Ralston Purina, St. Louis, Mo.) and water ad libitum. Upon arrival, the animals are allowed to acclimate for 24 hours. Hair is then clipped from the back of the animal in an area approximately 2×2 inches. The area is scrubbed with povidone-iodine (H&P Industries/Triad Medical Inc., Mukwonago, Wis.) followed by an alcohol scrub. Next, the animal is sensitized to *Candida albicans* antigens by injecting a 0.2 ml saline suspension of *Candida albicans* A26 (ATCC 90234) intradermally on the dorsal side of the neck region. Cultures of *Candida albicans* A26 are maintained at −80° C. in a glycerol and lactose freezing solution, and are grown aerobically on Sabourauds and dextrose agar slants (DIFCO, Detroit, Mich.) at 35° C. for 24 hours. Cultures are then suspended in sterile saline and adjusted spectrophotometrically to a predetermined optical density equivalent to approximately $2.0 \times 10^7$ cells/ml before use.

Three days following sensitization, the animals are treated with Compound 1 formulated in sterile water for injection (Abbott Laboratories, North Chicago, Ill.) at 100, 10 and 1.0 ng per 0.2 ml. The animals are injected subcutaneously on the dorsal side of the neck with 0.2 ml. A third group of animals dosed with the water vehicle serves as the positive control group.

Four days following sensitization, the animals are shaved and scrubbed as described above. Four equally spaced areas in the shaved region are injected intradermally with 0.1 ml of Candin (Allermed Laboratories, Inc., San Diego, Calif.), which serves as a recall antigen for T cells that have been previously sensitized to *C. albicans*. The animals are observed daily over three days for erythema, wheals, and indurations at these four sites. Two traverse (vertical and horizontal) diameters of the flares are, recorded for each site. These are averaged and a mean of the flare area ($mm^2$) is calculated. Treated animals are compared to untreated controls in order to assess therapeutic efficacy.

A reduction in the flare area in animals treated with Compound 1 as compared to that of control animals demonstrates that a DTH skin assay is an appropriate biomarker for clinical use and evaluation of polysaccharide immunomodulators such as compounds of Formula VI.

EXAMPLE 15

Differential Induction of TNF-α in Human PBMCs by Compounds of Formulae V and VI The ability of compounds of Formulae V and VI to induce the production of the pro-inflammatory cytokine TNF-α by human peripheral blood mononuclear cells (PBMCs) is determined as follows.

PBMCs from a human donor are isolated by density gradient centrifugation over Ficoll (Pharmacia, Uppsala, Sweden) plated at a density of $1.0 \times 10^6$ cells/ml in RPMI medium containing 10% FBS (both from Invitrogen Corporation, Carlsbad, Calif.), and separately incubated at 37° C. in a 5% $CO_2$ atmosphere for 18 h either in the presence or absence of Compound 1 and Compound 2. Separate control cells are incubated under the same conditions as above with 10 ng/ml *S. aureus* peptidoglycan (Sigma), which is a potent inflammatory peptidoglycan. After incubation, the tissue culture medium is removed from the various cells by pipetting, and the amount of TNF-α present therein is determined using a commercially available sandwich ELISA kit that utilizes a monoclonal antibody to TNF-α (BD OptEIA™ Set Human TNF, Catalog No. 555212, Pharmingen, Inc.). This ELISA assay has a limit of detection for TNF-α of 7.8 pg/ml.

Incubation with 500 μg/ml, 100 μg/ml and 1 μg/ml of Compound 2 for 18 h induces the production of 64.0 pg/ml, 17.6 pg/ml and 1.82 pg/ml TNF-α, respectively, whereas no detectable TNF-α is observed using the same concentrations of Compound 1 with these donor cells. Incubation with 10 ng/ml of *S. aureus* peptidoglycan induces 26 pg/ml TNF-α in these donor cells.

These results demonstrate that human PBMCs recognize Compound 2, which is representative of compounds of Formula V, with the production of the pro-inflammatory cytokine TNF-α at the concentrations used. In contrast, Compound 1, which is representative of compounds of Formula VI, does not induce TNF-α in these PBMCs. These observations are consistent with those described in Example 15.

The invention being thus described, it is obvious that the same can be varied in many ways. Such variations are not to be regarded as a departure from the spirit and scope of the present invention, and all such modifications as would be obvious to one skilled in the art are intended to be included within the scope of the following claims.

We claim:
1. A linear, non-crosslinked, immunomodulatory polymeric compound, wherein the compound is

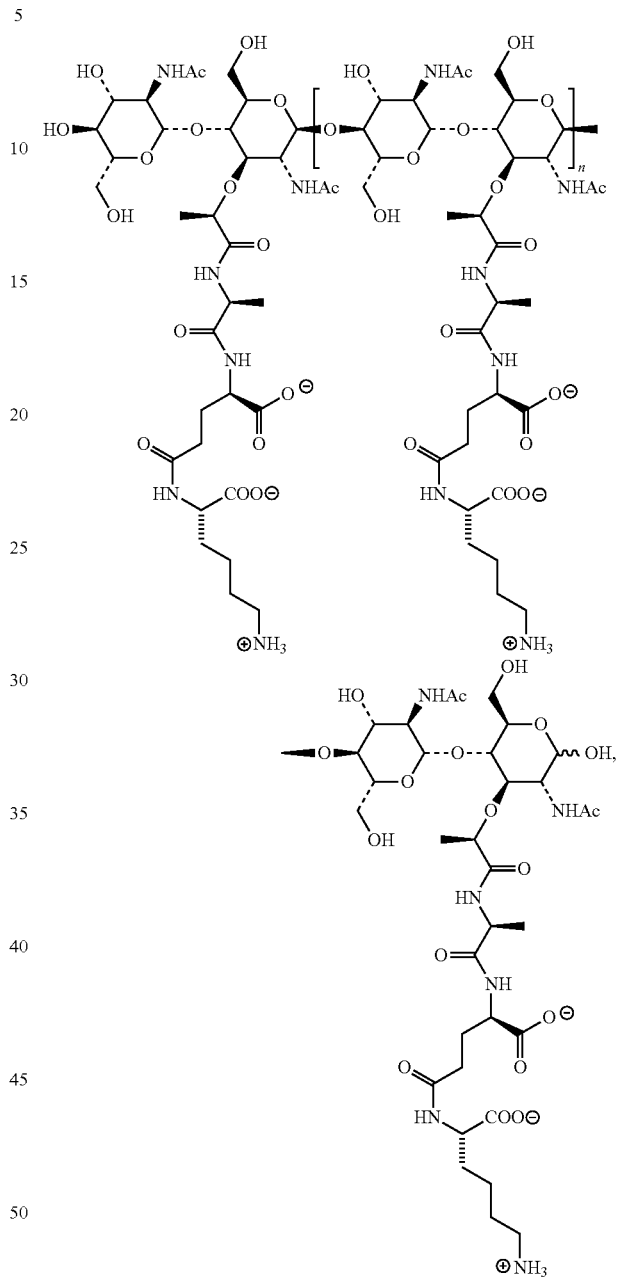

or a pharmaceutically acceptable salt thereof, wherein the compound has a molecular weight greater than about 10 kDa;

wherein said immunomodulatory polymeric compound stimulates TNF-alpha production of human peripheral blood mononuclear cells.

2. A pharmaceutical composition comprising the compound of claim 1, or a pharmaceutically acceptable salt thereof, together with a pharmaceutically acceptable diluent, excipient, or carrier.

3. A linear, non-crosslinked, immunomodulatory polymeric compound, wherein the compound is

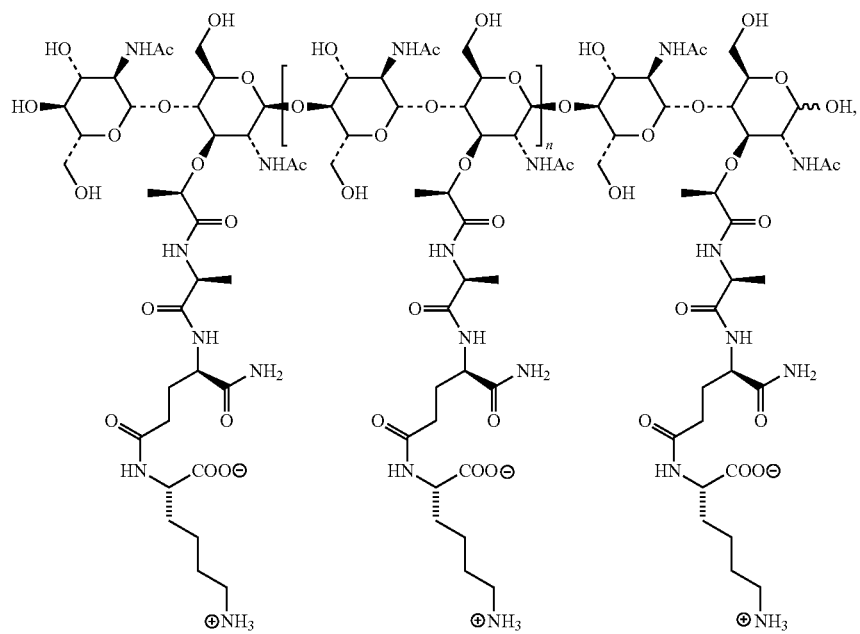

or a pharmaceutically acceptable salt thereof, wherein the compound has a molecular weight greater than about 10 kDa;

wherein said immunomodulatory polymeric compound stimulates TNF-alpha production of human peripheral blood mononuclear cells.

4. A pharmaceutical composition comprising the compound of claim 3, or a pharmaceutically acceptable salt thereof, together with a pharmaceutically acceptable diluent, excipient, or carrier.

* * * * *